(12) United States Patent
Brown et al.

(10) Patent No.: US 10,292,968 B2
(45) Date of Patent: May 21, 2019

(54) SUBSTITUTED HETEROCYCLES AS BROMODOMAIN INHIBITORS

(71) Applicant: Zenith Epigenetics Ltd., Calgary (CA)

(72) Inventors: Samuel David Brown, San Carlos, CA (US); Craig Alan Coburn, San Rafael, CA (US); Olesya Kharenko, Calgary (CA)

(73) Assignee: Zenith Epigenetics Ltd., Calgary, Alberta (CA)

( * ) Notice: Subject to any disclaimer, the term of this patent is extended or adjusted under 35 U.S.C. 154(b) by 0 days.

(21) Appl. No.: 15/534,105

(22) PCT Filed: Dec. 11, 2015

(86) PCT No.: PCT/IB2015/002479
§ 371 (c)(1),
(2) Date: Jun. 8, 2017

(87) PCT Pub. No.: WO2016/092375
PCT Pub. Date: Jun. 16, 2016

(65) Prior Publication Data
US 2017/0360756 A1    Dec. 21, 2017

Related U.S. Application Data

(60) Provisional application No. 62/090,853, filed on Dec. 11, 2014.

(51) Int. Cl.
| | |
|---|---|
| A61K 31/4178 | (2006.01) |
| A61K 31/4196 | (2006.01) |
| A61K 31/422 | (2006.01) |
| A61K 31/4245 | (2006.01) |
| C07D 403/04 | (2006.01) |
| C07D 413/04 | (2006.01) |
| A61K 31/4184 | (2006.01) |
| C07D 401/14 | (2006.01) |
| C07D 413/14 | (2006.01) |
| A61K 31/4439 | (2006.01) |
| A61K 31/4985 | (2006.01) |
| C07D 403/14 | (2006.01) |
| A61K 31/42 | (2006.01) |
| A61K 31/437 | (2006.01) |
| A61K 31/4545 | (2006.01) |
| A61K 31/496 | (2006.01) |
| A61K 31/498 | (2006.01) |
| A61K 31/517 | (2006.01) |
| A61K 31/52 | (2006.01) |

(Continued)

(52) U.S. Cl.
CPC ...... *A61K 31/4184* (2013.01); *A61K 31/4196* (2013.01); *A61K 31/42* (2013.01); *A61K 31/437* (2013.01); *A61K 31/4439* (2013.01); *A61K 31/4545* (2013.01); *A61K 31/496* (2013.01); *A61K 31/498* (2013.01); *A61K 31/4985* (2013.01); *A61K 31/517* (2013.01); *A61K 31/52* (2013.01); *A61K 31/5377* (2013.01); *A61P 35/00* (2018.01); *A61P 37/00* (2018.01); *C07D 401/14* (2013.01); *C07D 403/04* (2013.01); *C07D 403/14* (2013.01); *C07D 413/14* (2013.01); *A61K 45/06* (2013.01); *A61K 2300/00* (2013.01); *C07D 413/04* (2013.01); *C07D 471/04* (2013.01); *C07D 473/34* (2013.01); *Y02A 50/467* (2018.01)

(58) Field of Classification Search
CPC .............. C07D 403/04; C07D 413/04; A61K 31/4178; A61K 31/4196; A61K 31/422; A61K 31/4245
USPC ..... 548/263.2, 343.5, 314.7, 266.2; 514/397, 514/384
See application file for complete search history.

(56) References Cited

U.S. PATENT DOCUMENTS

| | | |
|---|---|---|
| 4,748,163 A | 5/1988 | Schmidt et al. |
| 5,385,925 A | 1/1995 | Narr et al. |

(Continued)

FOREIGN PATENT DOCUMENTS

| | | |
|---|---|---|
| CA | 2113361 A1 | 3/1993 |
| CA | 2087800 A1 | 7/1993 |

(Continued)

OTHER PUBLICATIONS

Aiello, R.J., et al., "Monocyte chemoattractant protein-1 accelerates atherosclerosis in apolipoprotein E-deficient mice" *Arterioscler Thromb. Vasc. Biol.* 19(6): 1518-25 (1999).

(Continued)

*Primary Examiner* — Matthew P Coughlin
*Assistant Examiner* — Sagar Patel
(74) *Attorney, Agent, or Firm* — Finnegan, Henderson, Farabow, Garrett & Dunner, LLP

(57) ABSTRACT

The present application relates to substituted heterocycles compound of Formula I and pharmaceutical compositions thereof useful for the inhibition of BET protein function by binding to bromodomains (Formula I).

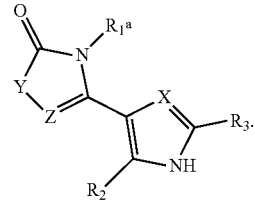

Formula I

30 Claims, No Drawings

(51) Int. Cl.
*A61K 31/5377* (2006.01)
*A61P 35/00* (2006.01)
*A61P 37/00* (2006.01)
A61K 45/06 (2006.01)
C07D 471/04 (2006.01)
C07D 473/34 (2006.01)

(56) References Cited

U.S. PATENT DOCUMENTS

| | | |
|---|---|---|
| 5,565,469 A | 10/1996 | Mihm et al. |
| 5,591,762 A | 1/1997 | Hauel et al. |
| 6,380,235 B1 | 4/2002 | Zhang et al. |
| 8,053,440 B2 | 11/2011 | Hansen |
| 8,093,273 B2 | 1/2012 | Wong et al. |
| 8,691,747 B2 | 4/2014 | Kruidenier et al. |
| 8,697,725 B2 | 4/2014 | Demont et al. |
| 8,735,586 B2 | 5/2014 | Alonso et al. |
| 8,993,554 B2 | 3/2015 | Amans et al. |
| 9,029,395 B2 | 5/2015 | Amans et al. |
| 9,067,936 B2 | 6/2015 | Demont et al. |
| 9,073,878 B2 | 7/2015 | Fairfax et al. |
| 9,102,677 B2 | 8/2015 | Bailey et al. |
| 9,125,915 B2 | 9/2015 | Miyoshi et al. |
| 9,271,978 B2 | 3/2016 | Liu et al. |
| 9,278,940 B2 | 3/2016 | Fairfax et al. |
| 9,315,487 B2 | 4/2016 | Amans et al. |
| 9,321,765 B2 | 4/2016 | Gong |
| 9,388,161 B2 | 7/2016 | Bair et al. |
| 9,393,232 B2 | 7/2016 | Ren et al. |
| 9,422,281 B2 | 8/2016 | Bair et al. |
| 9,458,145 B2 | 10/2016 | Aktoudianakis et al. |
| 9,458,156 B2 | 10/2016 | Norris et al. |
| 9,598,367 B2 | 3/2017 | Liu et al. |
| 9,636,328 B2 | 5/2017 | Liu et al. |
| 9,662,311 B2 | 5/2017 | Liu et al. |
| 9,663,520 B2 | 5/2017 | Quinn et al. |
| 9,718,847 B2 | 8/2017 | Zhang et al. |
| 9,765,039 B2 | 9/2017 | Fairfax et al. |
| 9,855,271 B2 | 1/2018 | Quinn et al. |
| 9,861,637 B2 | 1/2018 | Liu et al. |
| 2002/0019395 A1 | 2/2002 | Zhu et al. |
| 2003/0036545 A1 | 2/2003 | Castelhano et al. |
| 2004/0044203 A1 | 3/2004 | Wittman et al. |
| 2004/0166137 A1 | 8/2004 | Lackey |
| 2005/0014812 A1 | 1/2005 | Heyashida et al. |
| 2005/0176775 A1 | 8/2005 | Devadas et al. |
| 2005/0176858 A1 | 8/2005 | Nohara et al. |
| 2006/0178374 A1 | 8/2006 | Cui et al. |
| 2007/0134161 A1 | 6/2007 | Brown |
| 2007/0213323 A1 | 9/2007 | Imogai et al. |
| 2007/0275984 A1 | 11/2007 | Imogai et al. |
| 2008/0015196 A1 | 1/2008 | Doller et al. |
| 2008/0188467 A1 | 8/2008 | Wong et al. |
| 2008/0262207 A1 | 10/2008 | Duffin et al. |
| 2010/0063104 A1 | 3/2010 | Nakai et al. |
| 2010/0069367 A1* | 3/2010 | Boren ............... C07D 231/10 514/218 |
| 2010/0234354 A1 | 9/2010 | Dorsch et al. |
| 2010/0287714 A1 | 10/2010 | Jorgensen et al. |
| 2011/0070297 A1 | 3/2011 | Cao et al. |
| 2011/0136819 A1 | 6/2011 | Dorsch et al. |
| 2011/0136834 A1 | 6/2011 | Critchley et al. |
| 2011/0257181 A1 | 10/2011 | Stieber et al. |
| 2012/0004261 A1 | 1/2012 | Jorgensen et al. |
| 2012/0028912 A1 | 2/2012 | Zhou et al. |
| 2012/0157428 A1 | 6/2012 | Albrecht et al. |
| 2012/0208798 A1 | 8/2012 | Demont et al. |
| 2012/0208800 A1 | 8/2012 | Chung et al. |
| 2012/0208814 A1 | 8/2012 | Demont et al. |
| 2012/0220573 A1 | 8/2012 | Gosmini et al. |
| 2013/0085133 A1 | 4/2013 | Severson et al. |
| 2013/0143880 A1 | 6/2013 | Dudkin et al. |
| 2013/0261109 A1 | 10/2013 | Miyoshi et al. |
| 2013/0281396 A1 | 10/2013 | McLure et al. |
| 2013/0281397 A1 | 10/2013 | McLure et al. |
| 2013/0281398 A1 | 10/2013 | McLure et al. |
| 2013/0281399 A1 | 10/2013 | McLure et al. |
| 2014/0031336 A1 | 1/2014 | Amans et al. |
| 2014/0045834 A1 | 2/2014 | Demont et al. |
| 2014/0162971 A1 | 6/2014 | Wang et al. |
| 2014/0171462 A1 | 6/2014 | Demont et al. |
| 2014/0256700 A1 | 9/2014 | Poss et al. |
| 2014/0256705 A1 | 9/2014 | Hasvold et al. |
| 2014/0256706 A1 | 9/2014 | Wang et al. |
| 2014/0256710 A1 | 9/2014 | Liu et al. |
| 2014/0275030 A1 | 9/2014 | Combs et al. |
| 2014/0275079 A1 | 9/2014 | Hasvold et al. |
| 2014/0296229 A1 | 10/2014 | Engelhardt et al. |
| 2014/0296246 A1 | 10/2014 | Aktoudianakis et al. |
| 2014/0303121 A1 | 10/2014 | Zhang et al. |
| 2014/0336190 A1 | 11/2014 | Aktoudianakis et al. |
| 2014/0349990 A1 | 11/2014 | Blank et al. |
| 2015/0011540 A1 | 1/2015 | Combs et al. |
| 2015/0216168 A1 | 8/2015 | Frackenpohl et al. |
| 2015/0246919 A1 | 9/2015 | Engelhardt et al. |
| 2016/0137613 A1 | 5/2016 | Hansen |
| 2016/0193218 A1 | 7/2016 | Quinn et al. |
| 2017/0143731 A1 | 5/2017 | Liu et al. |
| 2017/0182029 A1 | 6/2017 | Liu et al. |
| 2017/0216257 A1 | 8/2017 | Liu et al. |
| 2017/0216301 A1 | 8/2017 | Quinn et al. |
| 2017/0320866 A1 | 11/2017 | Jiang et al. |
| 2017/0360760 A1 | 12/2017 | Kharenko et al. |
| 2017/0360765 A1 | 12/2017 | Jiang et al. |
| 2018/0092924 A1 | 4/2018 | Quinn et al. |
| 2018/0161337 A1 | 6/2018 | Quinn et al. |

FOREIGN PATENT DOCUMENTS

| | | |
|---|---|---|
| CA | 2093785 A1 | 10/1993 |
| CA | 2195107 A1 | 2/1996 |
| CA | 2440211 A1 | 9/2002 |
| CA | 2818187 A1 | 6/2012 |
| CA | 2895905 A1 | 6/2014 |
| CA | 2911408 A1 | 11/2014 |
| CA | 2915661 A1 | 1/2015 |
| CA | 2915838 A1 | 1/2015 |
| CA | 2915622 A1 | 1/2016 |
| CN | 1113235 A | 12/1995 |
| CN | 1636977 A | 7/2005 |
| CN | 1263757 C | 7/2006 |
| CN | 1934092 A | 3/2007 |
| CN | 101061098 A | 10/2007 |
| CN | 101220077 A | 7/2008 |
| CN | 101384593 A | 3/2009 |
| CN | 101636386 A | 1/2010 |
| CN | 101641339 A | 2/2010 |
| CN | 101983198 A | 3/2011 |
| CN | 102186833 A | 9/2011 |
| CN | 102731409 A | 10/2012 |
| CN | 105102453 A | 11/2015 |
| EP | 0 385 850 A2 | 9/1990 |
| EP | 0 556 789 A2 | 8/1993 |
| EP | 0 566 020 A1 | 10/1993 |
| EP | 1 375 486 A1 | 1/2004 |
| EP | 1 944 311 A1 | 7/2008 |
| EP | 0 195 947 B1 | 1/2010 |
| EP | 2 196 465 A1 | 6/2010 |
| EP | 2 390 270 A2 | 11/2011 |
| EP | 2 792 355 A1 | 10/2014 |
| JP | S61-207388 A | 9/1986 |
| JP | H04-253966 A | 9/1992 |
| JP | H04-346978 A | 12/1992 |
| JP | H05-279341 A | 10/1993 |
| JP | 2000-072675 A | 3/2000 |
| JP | 2003-523353 A | 8/2003 |
| JP | 2004-519512 A | 7/2004 |
| JP | 2004-524350 A | 8/2004 |
| JP | 2004-526727 A | 9/2004 |
| JP | 2004-534010 A | 11/2004 |
| JP | 2006-511600 A | 4/2006 |
| JP | 2006-522119 A | 9/2006 |
| JP | 2006-528677 A | 12/2006 |
| JP | 2007-530477 A | 11/2007 |

(56) References Cited

FOREIGN PATENT DOCUMENTS

| | | |
|---|---|---|
| JP | 2008-513414 A | 5/2008 |
| JP | 2008-169212 A | 7/2008 |
| JP | 2008-533151 A | 8/2008 |
| JP | 2009-517438 A | 4/2009 |
| JP | 2009-528989 A | 8/2009 |
| JP | 2009-532424 A | 9/2009 |
| JP | 2010-513224 A | 4/2010 |
| JP | 2010-532768 A | 10/2010 |
| JP | 2010-540590 A | 12/2010 |
| JP | 2012-500260 A | 1/2012 |
| JP | 2012-513418 A | 6/2012 |
| JP | 2012-520867 A | 9/2012 |
| JP | 2012-520884 A | 9/2012 |
| JP | 2015-532650 A | 11/2015 |
| JP | 2016-515584 A | 5/2016 |
| JP | 2016-520062 A | 7/2016 |
| JP | 2016-522246 A | 7/2016 |
| JP | 2016-523259 A | 8/2016 |
| JP | 2016-525078 A | 8/2016 |
| KR | 10-1165996 B1 | 10/2011 |
| KR | 10-1242572 B1 | 4/2012 |
| WO | WO 96/33194 A1 | 10/1996 |
| WO | WO 00/34248 A1 | 6/2000 |
| WO | WO 00/66564 A1 | 11/2000 |
| WO | WO 01/55132 A1 | 8/2001 |
| WO | WO 02/057267 A1 | 7/2002 |
| WO | WO 02/067675 A2 | 9/2002 |
| WO | WO 02/070486 A1 | 9/2002 |
| WO | WO 02/072576 A1 | 9/2002 |
| WO | WO 02/076976 A2 | 10/2002 |
| WO | WO 02/078708 A1 | 10/2002 |
| WO | WO 02/079192 A1 | 10/2002 |
| WO | WO 2004/024897 A2 | 3/2004 |
| WO | WO 2004/054984 A1 | 7/2004 |
| WO | WO 2004/078733 A1 | 9/2004 |
| WO | WO 2004/098494 A2 | 11/2004 |
| WO | WO 2004/108686 A2 | 12/2004 |
| WO | WO 2005/012292 | 2/2005 |
| WO | WO 2005/013950 A2 | 2/2005 |
| WO | WO 2005/075432 A1 | 8/2005 |
| WO | WO 2005/080380 A1 | 9/2005 |
| WO | WO 2005/090317 A1 | 9/2005 |
| WO | WO 2005/117876 A1 | 12/2005 |
| WO | WO 2005/121132 A1 | 12/2005 |
| WO | WO 2006/021886 A1 | 3/2006 |
| WO | WO 2006/030032 A1 | 3/2006 |
| WO | WO 2006/038734 A1 | 4/2006 |
| WO | WO 2006/099379 A2 | 9/2006 |
| WO | WO 2006/119400 A2 | 11/2006 |
| WO | WO 2007/016525 A2 | 2/2007 |
| WO | WO 2007/040208 A1 | 4/2007 |
| WO | WO 2007/063012 A1 | 6/2007 |
| WO | WO 2007/093901 A1 | 8/2007 |
| WO | WO 2007/113232 A1 | 10/2007 |
| WO | WO 2008/054599 A2 | 5/2008 |
| WO | WO 2008/072784 A1 | 6/2008 |
| WO | WO 2008/092231 A1 | 8/2008 |
| WO | WO 2008/153701 A1 | 12/2008 |
| WO | WO 2009/006959 A1 | 1/2009 |
| WO | WO 2009/024221 A1 | 2/2009 |
| WO | WO 2009/043883 A1 | 4/2009 |
| WO | WO 2009/054790 A1 | 4/2009 |
| WO | WO 2009/079001 A1 | 6/2009 |
| WO | WO 2009/099801 A1 | 8/2009 |
| WO | WO 2009/158258 A1 | 12/2009 |
| WO | WO 2010/021693 A2 | 2/2010 |
| WO | WO 2010/068483 A2 | 6/2010 |
| WO | WO 2010/072096 A1 | 7/2010 |
| WO | WO 2010/077275 A1 | 7/2010 |
| WO | WO 2010/097368 A1 | 9/2010 |
| WO | WO 2010/104851 A1 | 9/2010 |
| WO | WO 2010/106436 A2 | 9/2010 |
| WO | WO 2010/107739 A2 | 9/2010 |
| WO | WO 2010/123975 a1 | 10/2010 |
| WO | WO 2010/127976 A1 | 11/2010 |
| WO | WO 2011/054843 A1 | 5/2011 |
| WO | WO 2011/054846 A1 | 5/2011 |
| WO | WO 2011/143669 A2 | 11/2011 |
| WO | WO 2011/156626 A1 | 12/2011 |
| WO | WO 2011/159926 A1 | 12/2011 |
| WO | WO 2010/009258 A2 | 1/2012 |
| WO | WO 2012/003576 A1 | 1/2012 |
| WO | WO 2012/021382 A1 | 2/2012 |
| WO | WO 2012/040499 A2 | 3/2012 |
| WO | WO 2012/075456 A1 | 6/2012 |
| WO | WO 2012/143413 A1 | 10/2012 |
| WO | WO 2012/143416 A2 | 10/2012 |
| WO | WO 2012/174487 A2 | 12/2012 |
| WO | WO 2013/024104 A1 | 2/2013 |
| WO | WO 2013/027168 A1 | 2/2013 |
| WO | WO 2013/064900 A1 | 5/2013 |
| WO | WO 2013/082429 A1 | 6/2013 |
| WO | WO 2013/156869 A1 | 10/2013 |
| WO | WO 2013/158952 A1 | 10/2013 |
| WO | WO 2013/184878 A1 | 12/2013 |
| WO | WO 2013/186229 A1 | 12/2013 |
| WO | WO 2014/031928 A2 | 2/2014 |
| WO | WO 2014/037340 A1 | 3/2014 |
| WO | WO 2014/043246 A1 | 3/2014 |
| WO | WO 2014/078257 A1 | 5/2014 |
| WO | WO 2014/095775 A1 | 6/2014 |
| WO | WO 2014/096965 A2 | 6/2014 |
| WO | WO 2014/128070 A1 | 8/2014 |
| WO | WO 2014/128111 A1 | 8/2014 |
| WO | WO 2014/128655 A1 | 8/2014 |
| WO | WO 2014/134267 A1 | 9/2014 |
| WO | WO 2014/140076 A1 | 9/2014 |
| WO | WO 2014/140077 A1 | 9/2014 |
| WO | WO 2014/152029 A2 | 9/2014 |
| WO | WO 2014/154760 A1 | 10/2014 |
| WO | WO 2014/154762 A1 | 10/2014 |
| WO | WO 2014/159837 A1 | 10/2014 |
| WO | WO 2014/160873 A1 | 10/2014 |
| WO | WO 2014/165143 A1 | 10/2014 |
| WO | WO 2014/170350 A1 | 10/2014 |
| WO | WO 2014/173241 A1 | 10/2014 |
| WO | WO 2014/182929 A1 | 11/2014 |
| WO | WO 2014/191894 A1 | 12/2014 |
| WO | WO 2014/202578 A1 | 12/2014 |
| WO | WO 2015/002754 A2 | 1/2015 |
| WO | WO 2015/004533 A2 | 1/2015 |
| WO | WO 2015/004534 A2 | 1/2015 |
| WO | WO 2015/011084 A1 | 1/2015 |
| WO | WO 2015/013635 A2 | 1/2015 |
| WO | WO 2015/015318 A2 | 2/2015 |
| WO | WO 2015/086507 A1 | 2/2015 |
| WO | WO 2016/087936 A1 | 6/2016 |
| WO | WO 2016/087942 A1 | 6/2016 |
| WO | WO 2016/092375 A1 | 6/2016 |
| WO | WO 2016/097863 A1 | 6/2016 |
| WO | WO 2016/097870 A1 | 6/2016 |

OTHER PUBLICATIONS

Alexandraki, K. et al., "Inflammatory process in type 2 diabetes: The role of cytokines" *Ann N Y Acad Sci*, 2006. 1084:89-117.

Ambinter, "2(1H)-Pyridone, 1-[(4-chlorophenyl)methyl]-5-(1,3,4-oxadlazol-2-yl)—" Chemical Abstracts Record No. 1209999-95-0 [online], entered into STN Registry File Mar. 15, 2010.

Antonelli, A. et al., "Serum levels of proinflammatory cytokines interleukin-1beta, interleukin-6, and tumor necrosis factor alpha in mixed cryoglobulinemia" *Arthritis Rheum*, 2009. 60(12):3841-7.

Aricha, R. et al., "Blocking of IL-6 suppresses experimental autoimmune myasthenia gravis" *J Autoimmun*, 2011. 36(2):135-41.

Arif, M. et al., "Protein lysine acetylation in cellular function and its role in canver manifestation" *Biochim Biophys Acta*, 2010. 1799(10-12):702-16.

Ash, Z. and P. emery, "The role of tocilizumab in the management of rheumatoid arthritis" *Expert Opin Biol Ther*, 2012. 12(9): 1277-89.

Bandukwala, H.S. et al., "Selective inhibition of CD4+ T-cell cytokine production and autoimmunity by BET protein and c-Myc inhibitors" *Proc Natl Acad Sci USA*, 2012. 109(36):14532-7.

(56) References Cited

OTHER PUBLICATIONS

Bandyopaphyay, K. et al., "Spermidinyl-CoA-based HAT inhibitors block DNA repair and provide cancer-specific chemo- and radiosensitization" *Cell Cycle*, 2009. 8(17):2779-88. (Author's manuscript. 19 pages).

Banerjee, C. et al., "BET bromodomain inhibition as a novel strategy for reactivation of HIV-1" *J Leukoc Biol*, 2012. 92(6):1147-54.

Baron, P. et al., "Production of Il-6 by human myoblasts stimulated with Abeta: relevance in the pathogenesis of IBM" *Neurology*, 2001. 57(9):1561-5.

Bartholomeeusen, K. et al., "BET bromodomain inhibition activates transcription via a transient release of P-TEFb from 7SK snRNP" JBC In Press, 2012. M112.410746, 16 pages. Final publication in: *J Biol Chem*, 287:36609-16.

Bassiouny, D.A. and O. Shaker, "Role of interleukin-17 in the pathogenesis of vitiligo" *Clin Exp Dermatol*, 2011. 36(3):292-7.

Bayraktaroğlu, T. et al., "Serum levels of tumor necrosis factor-alpha, interleukin-6 and interleukin-8 are not increased in dyspeptic patients with Hellcobacter pylori-associated gastritis" *Mediators Inflamm*, 2004. 13(1):25-8.

Belanger, D.B. et al., "Discovery of imidazol[1,2-a]pyrazine-based Aurora kinase inhibitors" *Bioorg. Med. Chem. Lett.*, 20:5170-5174 (2010).

Belkina, A.C. and G.V. Denis, "BET domain co-regulators in obesity, inflammation and cancer" *Nat Rev Cancer*, 2012. 12(7):465-77.

Bellan, C. et al., "CDK9/CYCLIN T1 expression during normal lymphoid differentiation and malignant transformation" *J. Pathol.*, 2004. 203(4):946-52.

Belli, F. et al., "Cytokines assay in peripheral blood and bronchoalveolar lavage in the diagnosis and staging of pulmonary granulomatous diseases" *Int J Immunopathol Pharmacol*, 2000. 13(2):61-67.

Berkovits, B.D. et al., "The testis-specific double bromodomain-containing protein BRDT forms a complex with multiple spliceosome components and is required for mRNA splicing and 3'-UTR truncation in round spermatids" *Nucleic Acids Res*, 2012. 40(15):7162-75.

Besnard, A.G. et al., "Inflammasome-IL-1-Th17 response in allergic lung inflammation" *J Mol Cell Biol*, 2012 4(1):3-10.

Boring, L. et al., "Decreased lesion formation in CCR2-l-mice reveals a role for chemokines in the initiation of atherosclerosis" *Nature*, 1998. 394(6696):894-7.

Bradley, D.T. and S.E. Kountakis, "Role of interleukins and transforming growth factor-beta in chronic rhinosinusitis and nasal polyposis" *Laryngoscope*, 2005. 115(4):684-6.

Brennan, P., "Isoxazole Inhibitors of Bromodomains" presented at the *RSC Advances in Synthesis and Medicinal Chemistry Conference*, BioPark, Welwyn Garden City, UK, May 1, 2012 (46 pages).

Brodmerkel, C.M. et al., "Discovery and pharmacological characterization of a novel rodent-active CCR2 antagonist, INCB3344" *J Immunol*, 2005. 175(8):5370-8.

Brühl, H. et al., "Dual role of CCR2 during initiation and progression of collagen-induced arthritis: evidence for regulatory activity of CCR2+ T cells" *J Immunol*, 2004. 172(2):890-8.

Cannon, J.G., "Analog Design" in *Burger's Medicinal Chemistry and Drug Discovery*. 5th Ed., vol. 1: *Principles and Practice*. Manfred E. Wolff (ed.), John Wiley & Sons, Inc., New York, NY. 1995; Chapter 19, pp. 783-802.

Chaidos, A. et al., "Inhibition of bromodomain and extraterminal proteins (BET) as a potential therapeutic approach in haematological malignancies: emerging preclinical and clinical evidence" *Ther Adv Hematol*, 6(3):128-141 (2015 ).

ChemDiv, Inc. in Chemical Abstracts Record No. 1340694-11-8, Entered into the Registry File Nov. 4, 2011.

Chemical Abstracts Service, 'Registry' File, RN 1348682-08-5; STN Database [online], Entry Date: Dec. 4. 2011 (1 page).

Chemical Abstracts Service, 'Registry' File, RN 1349367-93-4; STN Database [online]. Entry Date: Dec. 6, 2011 (1 page).

Chen, L. et al., "IL-17RA aptamer-mediated repression of IL-6 inhibits synovium inflammation in a murine model of osteoarthritis" *Osteoarthritis Cartilage*, 2011. 19(6):711-8.

Chevrel, G. et al., "Interleukin-17 increases the effects of IL-1 beta on muscle cells: arguments for the role of T cells in the pathogenesis of myositis" *J Neuroimmunol*, 2003. 137(1-2):125:33.

Chung, C.W. et al., "Bromodomains: a new target class for small molecule drug discovery" *Drug Discovery Today: Therapeutic Strategies* 9(2-3):e111-e120 (2012).

Chung, C.W. et al., "Discovery and characterization of small molecule inhibitors of the BET family bromodomains" *J Med Chem*, 2011. 54(11):3827-38.

Chung, C.W., "Small Molecule Bromodomain Inhibitors: Extending the Druggable Genome" *Progr. Med. Chem.*, 51:1-55 (2012).

Cid, J.M. et al., "Discovery of 1,5-Disubstituted Pyridones: A New Class of Positive Allosteric Modulators of the Metabotropic Glutamate 2 Receptor" *ACS Chem. Neurosci.* 1:788-795 (2010).

clinical trials.gov, "A Study to Investigate the Safety, Pharmacokinetics, Pharmacodynamics, and Clinical Activity of GSK525762 in Subjects With NUT Midline Carcinoma (NMC) and Other Cancers" GlaxoSmithKline, Identifier NCT01587703, verified Dec. 2016 [online]. Retrieved from: https://clinicaltriais.gov/ct2/showNCT01587703, on Dec. 28. 2016 (6 pages).

Costello, J.F. et al., "Cyclin-dependent kinase 6 (CDK6) amplification in human gliomas identified using two-dimensional separation of genomic DNA" *Cancer Res*, 1997. 57(7):1250-4.

D'Auria, L. et al., "Cytokines and bullous pemphigoid" *Eur Cytokine Netw*, 1999. 10(2):123-34.

Dawson, J. et al., "Targeting monocyte chemoattractant protein-1 signalling in disease" *Expert Opin Ther Targets*, 2003. 7(1):35-48.

Dawson, M.A. et al., "Inhibition of BET Recruitment to Chromatin as an Effective Treatment for MLL-fusion Leukaemia" *Nature*, 2011, 478:529-533.

De Falco, G. et al., "Cdk9 regulates neural differentiation and its expression correlates with the differentiation grade of neuroblastoma and PNET tumors" *Cancer Biol Ther*, 2005. 4(3):277-81.

De Lemos, J.A. et al., "Association between plasma levels of monocyte chemoattractant protein-1 and long-term clinical outcomes in patients with acute coronary syndromes" *Circulation*, 2003. 107(5):690-5.

De Paiva, C.S, et al., "IL-17 disrupts corneal barrier following desiccating stress" *Mucosal Immunol*, 2009. 2(3):243-53.

Degoma, E.M. and D.J. Rader, "Novel HDL-directed pharmacotherapeutic strategies" *Nat Rev Cardiol*, 2011, 8(5):266-77.

Delmore, J.E. et al., "BET bromodomain inhibition as a therapeutic strategy to target c-Myc" *Cell*, 2011 146(6):904-17.

Deng, J. et al., "Th17 and Th1 T-cell responses in giant cell arteritis" *Circulation*, 2010. 121(7):906-15.

Denis, G.V. et al., "An emerging role for bromodomain-containing proteins in chromatin regulation and transcriptional control of adipogenesis" *FEBS Lett*, 2010. 584(15):3260-8. (Author manuscript, 21 pages).

Denis. G.V., "Bromodomain coactivators in cancer, obesity, type 2 diabetes, and inflammation" *Discov Med*, 2010. 10(55):489-99.

Deo, R. et al., "Association among plasma levels of monocyte chemoattractant protein-1, traditional cardiovascular risk factors, and subclinical atherosclerosis" *J Am Coll Cardiol*, 2004. 44(9): p. 1812-8.

Dias, P.M. and G. Banerjee, "The Role of Th17/IL-17 on Eosinophilic Inflammation" *J Autoimmun*, 2012. Article in Press: http://dx.doi.org/10.1016/j.jaut.2012.07.004. 12 pages.

Elliott, D.A. et al., "Apolipoproteins in the brain: implications for neurological and psychiatric disorders" *Clin Lipidol*, 2010. 51(4):555-573. (Author manuscript, 28 pages.).

El-Osta, H.E. and R. Kurzrock, "Castleman's disease: from basic mechanisms to molecular therapeutics" *Oncologist*, 2011. 16(4):497-511.

European Patent Application No. 13864406.7, by Zenith Epigenetics Corp.: Extended European Search Report, including Search Opinion, dated Mar. 30, 2016 (6 pages).

(56) References Cited

OTHER PUBLICATIONS

European Patent Application No. 14820520.6, by Zenith Epigenetics Corp.: Extended European Search Report, including Search Opinion, dated Feb. 8, 2017 (9 pages).
European Patent Application No. 14822480.1, by Zenith Epigenetics Corp.: Extended European Search Report, including Search Opinion, dated Jan. 4, 2017 (10 pages).
European Patent Application No. 14822511.3, by Zenith Epigenetics Corp.: Extended European Search Report, including Search Opinion, dated Jan. 2, 2017 (7 pages).
European Patent Application No. 14832298.5, by Zenith Epigenetics Corp.: Extended European Search Report, including Search Opinion, dated Nov. 11, 2016 (6 pages).
European Patent No. EP 0 385 850 A2: Machine English translation; retrieved from ProQuest Dialog, dated Aug. 15, 2016: 68 pages.
European Patent No. EP 0 556 789 A2. Machine English translation; retrieved from ProQuest Dialog, dated Aug. 15, 2016; 59 pages.
Feng, Q. et al., "An epigenomic approach to therapy for tamoxifen-resistant breast cancer" *Cell Research*, 24:809-819 (2014).
Fife, B.T. et al., "CC chemokine receptor 2 is critical for induction of experimental autoimmune encephalomyelitis" *J Exp Med*, 192(6):899-905 (2000).
Figueroa-Vega, N. et al., "Increased circulating pro-inflammatory cytokines and Th17 lymphocytes in Hashimoto's thyroiditis" *J Clin Endocrinol Metab*, 95(2):953-62 (2010).
Filippakopoulos, P. and S. Knapp, "Targeting bromodomains epigenetic readers of lysine acetylation" *Nature Reviews*, 13:337-356 (2014).
Filippakopoulos, P. et al., "Selective Inhibition of BET Bromodomains" *Nature*, 68:1067-1073 (2010).
Fish, P.V. et al., "Identification of a chemical probe for bromo and extra C-terminal bromodomain inhibition through optimization of a fragment-derived hit" *J. Med. Chem.* 55:9831-9837 (2012)
Freireich, E.J. et al., "Quantitative comparison of toxicity of anticancer agents in mouse, rat, hamster, dog, monkey, and man" *Cancer Chemother Rep*, 50(4):219-244 (1966).
French, C.A., "NUT midline carcinoma" *Cancer Genet Cytogenet*, 2010. 203(1):16-20. (Author manuscript, 9 pages.).
Fujioka, A. et al., "The analysis of mRNA expression of cytokines from skin lesions in Churg-Strauss syndrome" *J Dermatol*, 1998. 25(3):171-7.
Fujishima, S. et al., "Involvement of IL-17F via the induction of IL-6 in psoriasis" *Arch Dermatol Res*, 2010. 302(7):499-505.
Gagnon, D. et al., "Proteasomal degradation of the papillomavirus E2 protein is inhibited by overexpression of bromodomain-containing protein 4" *J Virol*, 2009. 83(9):4127-39.
Gaucher, J. et al., "Bromodomain-dependent stage-specific male genome programming by Brdt" *EMBO J*, 2012. 31(19):3809-20.
Gharbi et al., "Exploring the specificity of the PI3k family inhibitor LY294002" *Biochem. J.* 404:15-21 (2007).
Gloddek, B. et al., "Pharmacological influence on inner ear endothelial cells in relation to the pathogenesis of sensorineural hearing loss" *Adv Otorhinolaryngol*, 2002. 59:75-83.
Gong, J-H. et al., "An antagonist of monocyte chemoattractant protein 1 (MCP-1) inhibits arthritis in the MRL—lpr mouse model" *J Exp Med*, 1997. 186(1):131-7.
Gong, J-H. et al., "Post-onset inhibition of murine arthritis using combined chemokine antagonist therapy" *Rheumatology*, 2004. 43(1):39-42.
González-Serrano, M.E. et al., "Increased Pro-inflammatory Cytokine Production Lipopolysaccharide Stimulation in Patients with X-linked Agammaglobulinemia" *J Clin Immunol*, 2012. 32(5):967-74.
Gosling, J. et al., "MCP-1 deficiency reduces susceptibility to atherosclerosis in mice that overexpress human apolipoprotein B" *J Clin Invest*, 1999. 103(6):773-8.
Graber, J.J. et al., "Interleukin-17 in transverse myelitis and multiple sclerosis" *J Neuroimmunol*, 2008. 196(1-2):124-32.
Greenwald, R.J. et al., "E mµ-BRD2 transgenic mice develop B-cell lymphoma and leukemia" *Blood*, 2004. 103(4):1475-84.
Grunwald, C. et al., "Expression of multiple epigenetically regulated cancer/germline genes in nonsmall cell lung cancer" *Int J Cancer*, 2006. 118(10):2522-8.
Gu, L. et al., "Absence of monocyte chemoattractant protein-1 reduces atherosclerosis in low density lipoprotein receptor-deficient mice" *Mol Cell*, 1998. 2(2):275-81.
Gu, Y. et al., "Interleukin (IL)-17 promotes macrophages to produce IL-8, IL-6 and tumor necrosis factor-alpha in aplastic anaemia" *Br J Haematol*, 2008. 142(1):109-14.
Hankovszky, H.O. et al., "Synthesis and reaction of ortho-fluoronitroaryl nitroxides. Novel versatile synthons and reagents for spin labelling studies" *Can J Chem*, 67:1392-1400 (1989).
Harada, K. et al., "Periductal interleukin-17 production in association with biliary innate immunity contributes to the pathogenesis of cholangiopathy in primary biliary cirrhosis" *Clin Exp Immunol*, 2009. 157(2):261-70.
Haruta, H. et al., "Blockade of interleukin-6 signaling suppresses not only TH17 but also interphotoreceptor retinoid binding protein-specific Th1 by promoting regulatory T cells in experimental autoimmune uveoretinitis" *Invest Ophthalmol Vis Sci*, 2011. 52(6):3264-71.
Hay et al., "The design and synthesis of 5- and 6-isoxazolylbenzimidazoles as selective inhibitors of the BET bromodomains" *Med. Chem. Commun.* 4:140-144 (2013).
Hay, D.A. et al., "Discovery and Optimization of Small-Molecule Ligands for the CBP/p300 Bromodomains" *J. Am. Chem. Soc.* 136:9308-9319 (2014).
Hewings et al., "3,5-Dimethylisoxazoles Act as Acetyl-lysine-mimetic Bromodomain Ligands" *J. Med. Chem.* 54:6761-6770 (2011).
Hewings et al., "3,5-Dimethylisoxazoles inhibit the bromodomain-histone protein-protein interaction" *243rd National Spring Meeting of the American-Chemical-Society (Symposium on Ionic Liquids—Science and Applications)*, San Diego, CA. General Poster Session, Mar. 28, 2012. Poster 326 Abstract [online]. Retrieved from: http://acselb-529643017.us-west-2.elb.amazonaws.com/chem/243nm/program/view/php?pub_num=326&par=MEDI.
Hewings et al., "Optimization of 3,5-Dimethylisoxazole Derivatives as Potent Bromodomain Ligands" *J. Med. Chem.* 56:3217-3227 (2013).
Hewings et al., "Progress in the development and application of small molecule inhibitors of bromodomain-acetyl-lysine interactions" *J. Med. Chem.* 55:9393-9413 (2012).
Hintermann, S. et al., "Identification of a series of highly potent activators of the Nurr 2 signaling pathway" *Bioorg Med Chem Lett*, 17:193-196 (2007).
Hohki, S. et al., "Blockade of interleukin-6 signaling suppresses experimental autoimmune uveoretinitis by the inhibition of inflammatory Th17 responses" *Exp Eye Res*, 2010. 91(2):162-70.
Hölttä, V. et al., "IL-23/IL-17 immunity as a hallmark of Crohn's disease" *Inflamm Bowel Dis*, 2008. 14(9):1175-84.
Hoshino, I. and H. Matsubara, "Recent advances in histone deacetylase targeted cancer therapy" *Surg Today*, 2010. 40(9):809-15.
Huang, D. et al., "Absence of monocyte chemoattractant protein 1 in mice leads to decreased local macrophage recruitment and antigen-specific T helper cell type 1 immune response in experimental autoimmune encephalomyelitis" *J Exp Med*, 2001. 193(6):713-26.
Içöz, S. et al., "Enhanced IL-6 production in aquaporin-4 antibody positive neuromyelitis optica patients" *Int J Neurosci*, 2010. 120(1):71-5.
International Search Report and Written Opinion issued in International Application No. PCT/IB2013/000968; dated Sep. 13, 2013.
International Search Report and Written Opinion issued in International Application No. PCT/IB2013/001026; dated Sep. 30, 2013.
International Search Report and Written Opinion issued in International Application No. PCT/IB2013/001232; dated Sep. 6, 2013.
International Search Report and Written Opinion issued in International Application No. PCT/IB2013/003122; dated Jul. 9, 2014.
International Search Report and Written Opinion issued in International Application No. PCT/IB2013/003126; dated Jun. 26, 2014.
International Search Report and Written Opinion issued in International Application No. PCT/IB2013/003202: dated Jul. 17, 2014.

(56) References Cited

OTHER PUBLICATIONS

International Search Report and Written Opinion issued in International Application No. PCT/IB2014/002238; dated Apr. 23, 2015.
International Search Report and Written Opinion issued in International Application No. PCT/IB2014/002240; dated Mar. 10, 2015.
International Search Report and Written Opinion issued in International Application No. PCT/IB2014/002510; dated Apr. 15, 2015.
International Search Report and Written Opinion issued in International Application No. PCT/IB2015/002429; dated Apr. 13, 2016.
International Search Report and Written Opinion issued in International Application No. PCT/IB2015/002462; dated Apr. 13, 2016.
International Search Report and Written Opinion issued in International Application No. PCT/IB2015/002479; dated Apr. 21, 2016.
International Search Report and Written Opinion issued in International Application No. PCT/IB2015/002490; dated Apr. 1, 2016.
International Search Report and Written Opinion issued in International Application No. PCT/IB2015/002522; dated Apr. 13, 2016.
International Search Report and Written Opinion issued in International Application No. PCT/IB2016/001874; dated Apr. 25, 2016.
International Search Report and Written Opinion issued in International Application No. PCT/US2014/043423; dated Jan. 12, 2005.
Ishizu, T. et al., "CSF cytokine and chemokine profiles in acute disseminated encephalomyelitis" *J Neuroimmunol*, 2006. 175(1-2):52-58.
Ito, Y. et al., "Pathogenic significance of interleukin-6 in a patient with antiglomerular basement membrane antibody-induced glomerulonephritis with multinucleated giant cells" *Am J Kidney Dis*, 1995 26(1):72-9.
Jadidi-Niaragh, F. and A. Mirshafiey, "Th17 cell, the new player of neuroinflammatory process in multiple sclerosis" *Scand J Immunol*, 2011. 74(1): 1-13.
Jahagirdar, R. et al., "An Orally Bioavailable Small Molecule RVX-297 Significantly Decreases Disease in a Mouse Model of Multiple Sclerosis" (Poster Presentation). Word Congress of Inflammation, Paris, France, 2011, 1 page.
Jen, H-Y. et al., "Increased serum interleukin-17 and peripheral Th17 cells in children with acute Henoch-Schonlein purpura" *Pediatr Allergy Immunol*, 2011. 22(8):862-8.
Jia, S., et al., "The T helper type 17/regulatory T cell imbalance in patients with acute Kawasaki disease" *Clin Exp Immunol*, 2010. 162(1):131-7.
Johnston, R.B. et al., "Interleukin-11 and IL-17 and the pathogenesis of periodontal disease" *J Periodontol*, 2004. 75(1):37-43.
Kahawita, I.P. and D.N. Lockwood, "Towards understanding the pathology of erythema nodosum leprosum" *Trans R Soc Trop Med Hyg*, 2008. 102(4):329-37.
Kallen, K.J. et al., "New developments in IL-6 dependent biology and therapy: where do we stand and what are the options?" *Expert Opin Investig Drugs*, 1999. 8(9):1327-49.
Kaplanski, G. et al., "Jarisch-Herxheimer reaction complicating the treatment of chronic Q fever endocarditis: elevated TNF alpha and IL-6 serum levels" *J Infect*. 1998. 37(1):83-4.
Kappel, L.W. et al., "IL-17 contributes to CD4-mediated graft-versus-host disease" *Blood*, 2009. 113(4):945-52.
Katsifis, G.E. et al., "Systemic and local interleukin-17 and linked cytokines associated with Sjogren's syndrome immunopathogenesis" *Am J Pathol*, 2009. 175(3):1167-77.
Kawai, M. et al., "Sustained response to tocilizumab, anti-interleukin-6 receptor antibody, in two patients with refractory relapsing polychondritis" *Rheumatology*, 2009. 48(3):318-9.
Kawakami, T. et al., "Reduction of interleukin-6, interleukin-8, and anti-phosphatidylserine-prothrombin complex antibody by granulocyte and monocyte adsorption apheresis in a patient with pyoderma gangrenosum and ulcerative colitis" *Am J Gastroenterol*, 2009. 104(9):2363-4.
Kawakamim T. et al., "Serum levels of interleukin-6 in patients with cutaneous polyarteritis nodosa" *Acta Derm Venereol*, 2012. 92(3):322-3.
Kelly, P.N. and A. Strasser, "The role of Bcl-2 and its pro-survival relatives in tumourigenesis and cancer therapy" *Cell Death Differ*, 2011. 18(9):1414-24.
Kim, S.E. et al., "Increased serum interleukin-17 in Graves' ophthalmopathy" *Graefes Arch Clin Exp Ophthalmol*, 2012. 250(10):1521-6.
Kimura, A. and T. Kishimoto, "IL-6: regulator of Treg/Th17 balance" *Eur J Immunol*, 2010. 40(7):1830-5.
Koch, A.E. et al., "Enhanced production of monocyte chemoattractant protein-1 in rheumatoid arthritis" *J Clin Invest*, 1992. 90(3):772-9.
Kyburz, D. and M. Corr, "Th17 cells generated in the absence of TGF-beta induce experimental allergic encephalitis upon adoptive transfer" *Expert Rev Clin Immunol*, 2011. 7(3):283-5.
Lahdenperä, A.I. et al., "Up-regulation of small interleukin-17 immunity in untreated coeliac disease but not in potential coeliac disease or in type 1 diabetes" *Clin Exp Immunol*, 2012. 167(2):226-34.
Lamale, L.M. et al., "Interleukin-6, histamine, and methylhistamine as diagnostic markers for interstitial cystitis" *Urology*, 2006. 68(4):702-6.
Lamotte, Y. et al., "Identification of a novel series of BET family Bromodomain inhibitors: binding mode and profile of I-BET151 (GSK1210151A)" Bioorganic & Medicinal Chemistry Letters, 2012. Accepted manuscript, doi:10.1016/j.bmcl.2012.02.041. Final publication as: Seal, J. et al., "Identification of a novel series of BET family bromodomain inhibitors: binding mode and profile of I-BET151 (GSK1210151A)" *Bioorg Med Chem Lett*, 2012. 22(8):2968-72.
Latifi, S.Q. et al., "Persistent elevation of serum interleukin-6 in intraabdominal sepsis identifies those prolonged length of stay" *J Pediatr Surg*, 2004. 39(10):1548-52.
Lee, D.K. et al., "Androgen receptor interacts with the positive elongation factor P-TEFb and enhances the efficiency of transcriptional elongation" *J Biol Chem*, 2001. 276(13):9976-84.
Li, Z., et al., "The BET bromodomain inhibitor JQ1 activates HIV latency through antagonizing Brd4 inhibition of Tat-transactivation" *Nucleic Acids Res Advance Access*, 2012. DOI:10.1093/nar/gks976, 11 pages.
Lin, F.J. et al., "Imbalance of regulatory T cells to Th12 cells in IgA nephropathy" *Scand J Clin Lab Invest*, 2012. 72(3):221-9.
Linhares, U.C. et al., "The Ex Vivo Production of IL-6 and IL-21 by CD4(+) T Cells in Directly Associated with Neurological Disability in Neuromyelitis Optica Patients" *J Clin Immunol*, 2012, DOI 10.1007/s10875-012-9780-2, 11 pages.
Lopez-Robles, E. et al., "TNFalpha and IL-6 are mediators in the blistering process of pemphigus" *Int J Dermatol*, 2001. 40(3):185-8.
Lu, M.O. and J. Zhu, "The role of cytokines in Guiliain-Barre syndrome" *J Neurol*, 2011. 258(4):533-46.
Ma, D. et al., "Profile of Th17 cytokines (IL-17, TGF-beta, IL-6) and Th1 cytokine (IFN-gamma) in patients with immune thrombocytopenic purpura" *Ann Hematol*, 2008. 87(11):899-904.
Mahad, D.J. and R.M. Ransonhoff, "The role of MCP-1 (CCL2) and CCR2 in multiple sclerosis and experimental autoimmune encephalomyelitis (EAE)" *Semin Immunol*, 2003. 15(1):23-32.
Matzuk, M.M. et al., "Small-Molecule Inhibition of BRDT for Male Contraception" *Cell*, 2012. 150(4):673-684, with supplemental pages S1-S8.
McKeown, M. et al., "Biased Multicomponent Reactions to Develop Novel Bromodomain Inhibitors" *J Med Chem*, 57:9019-9027 (2014).
McKinley, L. et al., "TH17 cells mediate steroid-resistant airway inflammation and airway hyperresponsiveness in mice" *J Immunol*, 2008. 181(6):4089-97.
McMahon, G. "VEGF Receptor Signaling in Tumor Angiogenesis" *The Oncologist*, 5(Suppl 1):3-10 (2000).
Medina-Franco, J.L. et al., "Pyridin-2(1H)-ones: A Promising Class of HIV-f1 Non-nucleoside Reverse Transcriptase Inhibitors" *ChemMedChem*, 2:1141-1147 (2007).
Mendrzyk, F. et al., "Genomic and protein expression profiling identifies CDK6 as novel independent prognostic marker in medulloblastoma" *J Clin Oncol*, 2005. 23(34):8853-62.
Mertz, J.A., "Targeting MYC Dependence in Cancer By Inhibiting BET Bromodomains", *PNAS*, 108(40):16669-16674 (2011).

(56) References Cited

OTHER PUBLICATIONS

Min, C.K. et al., "Cutaneous leucoclastic vasculitis (LV) following bortezomib therapy in a myeloma patient; association with proinflammatory cytokines" *Eur J Haematol*, 2006. 76(3):265-8.

Mirguet, O. et al., "From ApoA1 upregulation to BET family bromodomain inhibition: discovery of I-BET151" *Bioorg Med Chem Lett*, Article in Press, 2012. doi: 10.1016/j.bmcl.2012.01.125, 5 pages. Final publication in vol. 22, No. 8, pp. 2963-2967.

Mitsuyama, K. et al., "STAT3 activation via interleukin 6 trans-signalling contributes to ileitis in SAMP1/Yit mice" *Gut*, 2006. 55(9):1263-9.

Miyazaki, et al., "Intravenous Injection of Rabbit Apolipoprotein A-I Inhibits the Progression of Atherosclerosis in Cholesterol-Fed Rabbits" *Arterioscler. Thromb. Vasc. Biol.* 15: 1882-1888 (1995).

Mok, M.Y. et al., "The relation of interleukin 17 (IL-17) and IL-23 to Th1/Th2 cytokines and disease activity in systemic lupus arythematosus" *J Rheumatol*, 2010. 37(10):2046-52.

Morin, R.D. et al., "Frequent mutation of histone-modifying genes in non-Hodgkin lymphoma" *Nature*, 2011. 476(7360):298-303. (Author manuscript, 17 pages).

Mudter, J. and M.F. Neurath, "IL-6 signaling in inflammatory bowel disease: pathophysiological role and clinical relevance" *Inflamm Bowel Dis*, 2007. 13(8):1016-23.

Muller Kobold, A.C. et al., "In vitro up-regulation of E-selectin and induction of interleukin-6 in endothelial cells by autoantibodies in Wegener's granulomatosis and microscopic polyanglitis" *Clin Exp Rheumatol*, 1999. 1794):433-40.

Muller, S. et al., "Bromodomains as therapeutic targets" *Expert Rev Mol Med*, 2011. 13: e29, 21 pages.

Nakahama, H. et al., "Distinct responses of interleukin-6 and other laboratory parameters to treatment in a patient with Wegener's granulomatosis" *Intern Med*, 1993. 32(2):189-92.

Narayana, B.L. et al., "Syntheiss of New 2-Substituted Pyrido[2,3-d]pyrimidine-4(1H)—ones and Their Antibacterial Activity" *Eur. J. Med. Chem.* 44(3):1369-1376 (2009).

Nelken, N.A. et al., "Monocyte chemoattractant protein-1 in human atheromatous plaques" *J Clin Invest*, 1991. 88(4):1121-7.

Ni, J. et al., "Involvement of Interleukin-17A in Pancreatic Damage in Rat Experimental Acute Necrotizing Pancreatitis" *Inflammation*, 2012. [online] DOI: 10.1007/s10753-012-9519-5, published Sep. 19, 2012 (13 pages).

Nicodeme et al., "Suppression of inflammation by a synthetic histone mimic" *Nature* 468:1119-1123 (2010).

Niu, J. and P.E. Kolattukudy, "Role of MCP-1 in cardiovascular disease: molecular mechanisms and clinical implications" *Clin Sci*, 117(3):95-109.

Ooi, J.D. et al, "Review: T helper 17 cells: their role in glomerulonephritis" *Nephrology*, 2010. 15(5):513-21.

Ortiz-Lucas, M. et al., "Irritable bowel syndrome immune hypothesis. Part two: the role of cytokines" *Rev Esp Enferm Dig*, 2010. 102(12):711-7.

Ott, C.J. et al., "BET bromodomain inhibition targets both c-Myc and IL7R in high-risk acute lymphoblastic leukemia" *Blood*, 2012. 120(14):2843-52.

Pakrashi, S.C. "4-Quinazolinones. II. Self-condensation of anthranilamide" *J Org Chem*, 36(5):642-645.

Palermo, R.D. et al., RNA polymerase II stalling promotes nucleosome occlusion and pTEFb recruitment to drive immortalization by Epstein-Barr virus. *PLoS Pathog*, 2011. 7(10):e1002334, 15 pages.

Paquet, P. and G.E. Pierard, "Interleukin-6 and the skin" *Int Arch Allergy Immunol*, 1996. 109(4):308-17.

Peserico, A. and C. Simone, "Physical and functional HAT/HDAC interplay regulates protein acetylation balance" *J Biomed Biotechnol*, 2011. 371832, 10 pages.

Pinedo, H.M. and D.J. Slamon, "Translationai Research: The Role of VEGF in Tumor Angiogenesis" *The Oncologist*, 5(Suppl. 1):1-2 (2000).

Poreba, E. et al., "Epigenetic mechanisms in virus-induced tumorigenesis" *Clin Epigenetic*, 2011. 2(2):233-47.

Prabakaran, K. et al., "Iridium bromide catalysed, ultrasound-assisted, region-selective synthesis of ethyl-5-(trifluoroinethyl)-1-(3-substituted-isoquinolin-l-yl)-1H-pyrazole-4-carboxylates", *Res. Chem. Intermed.*, 38:429-441 (2012).

Prinjha, R.K. et al., "Place your BETs: the therapeutic potential of bromodomains" *Trends Pharmacol Sci*, 2012. 33(3):146-53.

Radstake, T.R. et al., "The pronounced Th17 profile in systemic sclerosis (SSc) together with intracellular expression of TGFbeta and IFNgamma distinguishes SSc phenotypes" *PLoS One*, 2009. 4(6):e5903. 9 pages.

Ramsay, R.G. and T.J. Gonda, "MYB function in normal and cancer cells" *Nat Rev Cancer*, 2008. 8(7):523-34.

Raychaudhuri, S.P. et al., "IL-17 receptor and its functional significance in psoriatic arthritis" *Mol Cell Biochem*, 2012. 359(1-2):419-29.

Rhodus, N.L. et al., "Proinflammatory cytokine levels in saliva before and after treatment of (erosive) oral lichen planus with dexamethasone" *Oral Dis*. 2006. 12(2):112-6.

Rodriguez, R.M. et al., "Aberrant epigenetic regulation of bromodomain BRD4 in human colon cancer" *J Mol Med*, 2012. 90(5):587-95.

Roger, V.L. et al., "Heart disease and stroke statistics—2012 update: a report from the American Heart Association" *Circulation*, 2012. 125(1):3-e220.

Ruden, M. and N. Puri, "Novel anticancer therapeutics targeting telomerase" *Cancer Treat Rev*, 2012. Article in Press: http://dx.doi.org/10.1016/1.ctrv.2012.06.007, 13 pages.

Rudloff, U. and Y. Samuels, "TYRO3-mediated regulation of MITF: a novel target in melanoma?" *Pigment Cell Melanoma Res*, 2010. 23(1):9-11.

Sanchez. R. and M.M. Zhou, "The role of human bromodomains in chromatin biology and gene transcription" *Curr Opin Drug Discov Devel*, 2009. 12(5):659-65. (Author manuscript, 12 pages)

Scanlan, M.J. et al., "Expression of cancer-testis antigens in lung cancer: definition of bromodomain testis-specific gene (BRDT) as a new CT gene, CT9" *Cancer Lett*, 2000. 150(2):155-64.

Seal., J. et al., "Identification of a novel series of BET family bromodomain inhibitors: Binding mode and profile of I-BET15I(GSK121051A)" *Bioorg. Med. Chem. Lett.*, 22:2968-2972 (2012).

Segura, M.F. et al., "BRD4 is a novel therapeutic target in melanoma" Poster Presentation, AACR 103rd Annual Meeting, Mar. 31-Apr. 4, 2012 in Chicago, IL. *Cancer Research*, 2012. 72(8), Supplement 1, Abstract 2185.

Shang, E. et al., "The first bromodomain of Brdt, a testis-specific member of the BET sub-family of double-bromodomain-containing proteins, is essential for male germ cell differentiation" *Development*, 2007. 134(19):3507-15.

Shibuya, M. et al., "Successful treatment with tocilizumab in a case of Cogan's syndrome complicated with aortitis" *Mod Rheumatol*, 2012. online: DOI 10.1007/s10165-012-0691-0. 5 pages.

Simmons, E.M. et al., "Plasma cytokine levels predict mortality in patients with acute renal failure" *Kidney Int*, 2004. 65(4):1357-65.

Simone, C. and A. Giordano, "Abrogation of signal-dependent activation of the cdk9/cyciin T2a complex in human RD rhabdomyosarcoma cells" *Cell Death Differ*, 2007. 14(1):192-5.

Soltesz. P. et al., "Immunological features of primary anti-phospholipid syndrome in connection with endothelial dysfunction" *Rheumatology*, 2008. 47(11):1628-34.

Stenman, G. et al., "New tricks from an old oncogene: gene fusion and copy number alterations of MYB in human cancer" *Cell Cycle*, 2010. 9(15):2966-95.

Sun, Y. et al., "MMP-9 and IL-6 are potential biomarkers for disease activity in Takayasu's arteritis" *Int J Cardiol*, 2012. 156(2):236-8.

Tang, X. et al., "Assessment of Brd4 inhibition in idiopathic pulmonary fibrosis lung fibroblasts and in vivo models of lung fibrosis" *Am. J. Pathol.*, 163(2):470-479 (2013).

Taylan, A. et al., "Evaluation or the T helper 17 axis in ankylosing spondylitis" *Rheumatol Int*, 2012. 32(8):2511-5.

Tong, W.G. et al., "Phase I and pharmacologic study of SNS-032, a potent and selective Cdk2, 7, and 9 inhibitor, in patients with advanced chronic lymphocytic leukemia and multiple myeloma" *J Clin Oncol*, 2010. 28(18):3015-22.

(56) References Cited

OTHER PUBLICATIONS

Traves, S.L. and L.E. Donnelly, "Th17 cells in airway diseases" *Curr. Mol. Med.*, 2008. 8(5):416-26.
Uchida, T. et al., "Antitumor effect of bcl-2 antisense phosphorothioate oligodeoxynucleotides on human renal-cell carcinoma cells in vitro and in mice" *Mol Urol*, 2001. 5(2):71-8.
Urano, W. et al., "The inflammatory process in the mechanism of decreased serum uric acid concentrations during acute gouty arthritis" *J Rheumatol*, 2002. 29(9):1950-3.
Utsunomiya, I. et al., "Preparation of Alkyl-Substituted Indoles in the Benzene Portion. Part 13. Enantiospecific Synthesis of Mitosene Analogues Related to FFR 900482 and FR 66979" *Chem Pharm Bull*, 43(1):37-48.
Velisek, L. et al., "GABAergic neuron deficit as an idiopathic generalized epilepsy mechanism: the role of BRD2 haploinsufficiency in juvenile myoclonic epilepsy" *PLoS One*, 2011. 6(8): e23656, 8 pages.
Vernarecci, S. et al., "Tuning acetylated chromatin with HAT inhibitors: a novel tool for therapy" *Epigenetics*, 2010. 5(2): p. 105-11.
Vidal, B. et al., "Discovery and Characterization of 4'-(2-Furyl)-N-pyridin-3-yl-4,5'-bipyrimidin-2'-amine (LAS38096), a Potent, Selective, and Efficacious $A_{2B}$ Adenosine Receptor Antagonist" *J. Med. Chem.* 50:2732-2736 (2007).
Vidler, L.R. et al., "Discovery of Novel Small-Molecule Inhibitors of BRD4 Using Structure-Based Virtual Screening" *J Med Chem*, 56:8073-8088 (2013).
Vippagunta, S.R. et al., "Crystalline solids" *Adv Drug Del Rev*, 2001. 48:3-26.
Vita, M. and M. Henriksson, "The Myc oncoprotein as a therapeutic target for human cancer" *Semin Cancer Biol*, 2006. 16(4):318-30.
Voitenko et al., "Esters of o-(4-oxo-3,4-dihydro-2-quinazolinyl)benzoic acid and 5,11-dihydroisoindolo[2,1-a]quinazolinone-5 derivatives as β-cyclodextrin modifiers" *Dopovidi Natsional'noi Akademii Nauk Uraini* (Reports of the National Academy of Sciences of Ukraine), 8:132-138 (2005) English abstract on p. 132.
Wang, F. et al., "Brd2 disruption in mice causes severe obesity without Type 2 diabetes" *Biochem J*, 2010. 425(1): p. 71-83, with supplemental online material, 2 pages.
Wang, G. et al., "Increased cyclin-dependent kinase 6 expression in bladder cancer" *Oncol Lett*, 2012. 4(1): p. 43-46.
Wang, S. and P.M. Fischer, "Cyclin-dependent kinase 9: a key transcriptional regulator and potential drug target in oncology, virology and cardiology" *Trends Pharmacol Sci*, 2008. 29(6):302-13.
Watson, J.D., "Curing 'incurable' cancer" *Cancer Discov*, 2011 1(6):477-80.
Wu, S.Y. ans C.M. Chiang, "The double bromodomain-containing chromatin adaptor Brd4 and transcriptional regulation" *J Biol Chem*, 2007. 282(18):13141-5.
Xing, W. et al., "Discovery of novel 2,6-disubstituted pyridazinone derivatives as acetylcholinesterase inhibitors" *Eur. J. Med. Chem.* 63:95-103 (2013).
Xu, L. et al., "Critical role of Th17 cells in development of autoimmune hemolytic anemia" *Exp Hemetol*, 2012. Article in Press: http://dx.doi.org/10.1016/j.exphem.2012.08.008, 15 pages.
Yamaguchi, M. et al., "Novel Antiasthmatic Agents with Dual Activities of Thromboxane $A_2$ Synthetase Inhibition and Bronchodilation. 2. 4(3-Pyridyl)-1(2H)-phthalazinones" *J. Med. Chem.*, 36:4061-4068 (1993)
Yamashita, T. et al., "IL-6-mediated Th17 differentiation through RORγt is essential for the initiation of experimental autoimmune myocarditis" *Cardiovasc Res*, 2011. 91(4):640-6.
Yoshii, T. et al., "Local levels of interleukin-1beta,—4,—6 and tumor necrosis factor alpha in an experimental model of murine osteomyelitis due to *Staphylococcus aureus*" *Cytokine*, 2002. 19(2):59-65.
Yoshimura, T. et al., "Involvement of Th17 cells and the effect of anti-IL-6 therapy in autoimmune uveitis" *Rheumatology*, 48(4):347-354 (2009).
You, J. et al., "Kaposi's sarcoma-associated herpesvirus latency-associated nuclear antigen interacts with bromodomain protein Brd4 on host mitotic chromosomes" *J Virol*, 2006, 80(18):8909-19.

Yu et al., "Discovery of Highly Potent and Selective α4β2-Nicotinic Acetylcholine Receptor (nAChR) Partial Agonists Containing an Isoxazolylpyridine Ether Scaffold that Demonstrate Antidepressant-like Activity" *J Med Chem*, 55:9998-10009 (2012).
Yu et al., "Toll-Like Receptor 7 Agonists: Chemical Feature Based Pharmacophore Identification and Molecular Docking Studies" *PLoS ONE* 8(3):e56514, doi:10.1371/journal.pone.0056514 (2013).
Zhang, G. et al., "Down-regulation of NF-kappaB Transcriptional Activity in HIVassociated Kidney Disease by BRD4 inhibition" *JBC Papers In Press*, 2012. M112.359505 with supplement, 38 pages. Final publication in: *J Biol Chem*, 287(34):28840-51.
Zhang, W.S. et al., "Bromodomain-Containing-Protein 4 (BRD4) Regulates RNA Polymerase II Serine 2 Phosphorylation in Human CD4+ T Cells" JBC Papers in Press, 2012. M112.413047, 30 pages. Final publication in: *J Biol Chem*, 287:43137-55.
Zhao, L. et al., "Interleukin-17 contributes to the pathogenesis of autoimmune hepatitis through inducing hepatic interleukin-6 expression" *PLoS One*, 2011. 6(4):e18909, 8 pages.
Zhou, M. et al., "Bromodomain protein Brd4 regulates human immunodeficiency virus transcription through phosphorylation of CDK9 at threonine 29" *J Virol*. 2009. 83(2):1036-44.
Zhu, J. et al., "Reactivation of Latent HIV-1 by Inhibition of BRD4" *Cell Rep*, 2012. 2:1-10, with supplemental pp. S1-S7.
Zuber, J. et al., "RNAi screen identifies Brd4 as a therapeutic target in acute myeloid leukaemia" *Nature*, 2011. 478(7370):524-8.
Bernstein, J. (2002) *Polymorphism in Molecular Crystals*. Oxford: Clarendon Press; pp. 115-118,272.
Braga, D. et al. (2005) "Making crystals from crystals: a green route to crystal engineering and polymorphism" *J Royal Soc Chem Commun*, 2005:3635-3645.
Chemical Abstracts Service, 'Registry' File, RN 1209999-95-0; STN Database [online]. Entry Date: Mar. 15, 2010 (1 page).
Davidovich, M. et al. (2004) "Detection of Polymorphism by Powder X-Ray Diffraction: Interference by Preferred Orientation" *Am Pharm Rev*, 7(1):10,12,14,16,100.
Dean, J.A. (1995) *Analytical Chemistry Handbook*. McGraw-Hill, Inc.; pp. 10.24-10.26.
Dikov, A. et al. (1996) "New fluorogenic substrates in histochemistry of peptidases. II. Histochemical demonstration of dipeptidyl peptidase IV" *Comptes rendus de l'Acacémie bulgare des Sciences*, 49(6):99-102.
Gottschalk, S. et al., "An Epstein-Barr virus deletion mutant associated with fatal lymphoproliferative disease unresponsive to therapy with virus-specific CTLs" *Blood*, 2001. 97:835-843.
Grant, D.J.W., "Theory and Origin of Polymorphism" in *Polymorphism in Pharmaceutical Solids*. Brittain, Harry G. (Ed.) New York, NY: Marcel Dekker, Inc., 1999; pp. 1-2.
Guillory, J.K. "Generation of Polymorphs, Hydrates, Solvates, and Amorphous Solids" in *Polymorphism in Pharmaceutical Solids*. Brittain, Harry G. (Ed.) New York, NY: Marcel Dekker, Inc., 1999; pp. 183-226.
He, A. and J.J.L. Miranda, "JQ1 reduces Epstein-Barr virus-associated lymphoproliferative disease in mice without sustained oncogene repression" *Leukemia & Lymphoma*, 2017. DOI: 10.1080/10428194.2017.1372578 [online]. Retrieved Oct. 31, 2017 (5 pages).
Hörig, H. and W. Pullman (2004) "From bench to clinic and back: Perspective on the 1st IQPC Translational Research conference" *J Transl Med*, 2:44 (8 pages).
Ivanisevic, I. et al. (2010) "Uses of X-Ray Powder Diffraction in the Pharmaceutical Industry" in *Pharmaceutical Sciences Encyclopedia: Drug Discovery, Development, and Manufacturing*. Gad, Shayne C. (Ed.) John Wiley & Sons, Inc.; pp. 1-42.
Jain, N.K. et al. (1986) "Polymorphism in Pharmacy" *Indian Drugs*, 23(6):315-329.
Jordan, V.C. (2003) "Tamoxifen: a most unlikely pioneering medicine" *Nat Rev Drug Disc*, 2:205-213.
Kirk-Othmer Encyclopedia of Chemical Technology, 8, 2002, pp. 95-147.
Liu et al. (2014) HCAPLUS database, Accession No. 2014:1037890. Columbus, Ohio: STN International. Retrieved Mar. 5, 2018 (2 pages).
McLaughlin-Drubin, M.E. and K. Munger, "Viruses Associated with Human Cancer" *Biochim Biophys Acta*, 2008. 1782(3):127-150. NIH Public Access Author Manuscript; available in PMC Mar. 1, 2009 (50 pages).
Morris, K.R. "Structural Aspects of Hydrates and Solvates" in *Polymorphism in Pharmaceutical Solids*. Brittain, Harry G. (Ed.) New York, NY: Marcel Dekker, Inc., 1999; pp. 125-181.

(56) References Cited

OTHER PUBLICATIONS

Patton, J.T. et al., "Silvestrol Modulates Direct Anti-Tumor Activity Against Epstein-Barr Virus (EBV)—Associated Lymphomas While Sparing Innate and Antigen Specific Adaptive Immunity" *Blood*, 2011. 118:Abstract 104 (2 pages).

Schäfer, S. and P. Kolkhof (2008) "Failure is an option: learning from unsuccessful proof-of-concept trials" *Drug Disc Today*, 13(21/22):913-916.

Seddon, K.R. (2004) "Pseudopolymorph: A Polemic" *Crystal Growth & Design*, 4(6):1087; doi: 10.1021/cg030084yS1528-7483(03)00084-6 [online]. Retrieved from: http://pubs.acs.org, on Nov. 6, 2006 (2 pages).

Ulrich, J. "Crystallization" in *Kirk-Othmer Encyclopedia of Chemical Technology*. John Wiley & Sons, Inc., vol. 8, pp. 95-147 (2002).

Whelligan, D.K. et al. "Aminopyrazine inhibitors binding to an unusual inactive conformation of the mitotic kinase Nek2: SAR and structural characterization" *J Med Chem*, 53(21):7682-7698 (2010).

Yamaguchi, M. et al., "Novel Antiasthmatic Agents with Dual Activities of Thromboxane $A_2$ Synthetase Inhibition and Bronchodilation. 1. 2-[2-(1-Imidazolyl)alkyl]-1(2H)-phthalazinones" *J. Med. Chem.*, 36:4052-4060 (1993).

Yu, L. et al. (1998) "Physical characterization of polymorphic drugs: an integrated characterization strategy" *PSTT*, 1(3):118-127.

\* cited by examiner

SUBSTITUTED HETEROCYCLES AS BROMODOMAIN INHIBITORS

This application is a U.S. national stage entry under 35 U.S.C. § 371 of International Application No. PCT/IB2015/002479, filed Dec. 11, 2015, which claims priority to U.S. Provisional Patent Application No. 62/090,853, filed Dec. 11, 2014, all of which are hereby incorporated by reference in their entirety.

The invention provides novel compounds, pharmaceutical compositions containing such compounds, and their use in prevention and treatment of diseases and conditions associated with bromodomain and extra terminal domain (BET) proteins.

Post-translational modifications (PTMs) of histones are involved in regulation of gene expression and chromatin organization in eukaryotic cells. Histone acetylation at specific lysine residues is a PTM that is regulated by histone acetylases (HATs) and deacetylases (HDACs). Peserico, A. and C. Simone, "Physical and functional HAT/HDAC interplay regulates protein acetylation balance," *J Biomed Biotechnol*, 2011:371832 (2011). Small molecule inhibitors of HDACs and HATs are being investigated as cancer therapy. Hoshino, I. and H. Matsubara, "Recent advances in histone deacetylase targeted cancer therapy" *Surg Today* 40(9):809-15 (2010); Vernarecci, S., F. Tosi, and P. Filetici, "Tuning acetylated chromatin with HAT inhibitors: a novel tool for therapy" *Epigenetics* 5(2):105-11 (2010); Bandyopadhyay, K., et al., "Spermidinyl-CoA-based HAT inhibitors block DNA repair and provide cancer-specific chemo- and radio-sensitization," *Cell Cycle* 8(17):2779-88 (2009); Arif, M., et al., "Protein lysine acetylation in cellular function and its role in cancer manifestation," *Biochim Biophys Acta* 1799 (10-12):702-16 (2010). Histone acetylation controls gene expression by recruiting protein complexes that bind directly to acetylated lysine via bromodomains. Sanchez, R. and M. M. Zhou, "The role of human bromodomains in chromatin biology and gene transcription," *Curr Opin Drug Discov Devel* 12(5):659-65 (2009). One such family, the bromodomain and extra terminal domain (BET) proteins, comprises Brd2, Brd3, Brd4, and BrdT, each of which contains two bromodomains in tandem that can independently bind to acetylated lysines, as reviewed in Wu, S. Y. and C. M. Chiang, "The double bromodomain-containing chromatin adaptor Brd4 and transcriptional regulation," *J Biol Chem* 282(18):13141-5 (2007).

Interfering with BET protein interactions via bromodomain inhibition results in modulation of transcriptional programs that are often associated with diseases characterized by dysregulation of cell cycle control, inflammatory cytokine expression, viral transcription, hematopoietic differentiation, insulin transcription, and adipogenesis. Belkina, A. C. and G. V. Denis, "BET domain co-regulators in obesity, inflammation and cancer," *Nat Rev Cancer* 12(7): 465-77 (2012). BET inhibitors are believed to be useful in the treatment of diseases or conditions related to systemic or tissue inflammation, inflammatory responses to infection or hypoxia, cellular activation and proliferation, lipid metabolism, fibrosis, and the prevention and treatment of viral infections. Belkina, A. C. and G. V. Denis, "BET domain co-regulators in obesity, inflammation and cancer," *Nat Rev Cancer* 12(7):465-77 (2012); Prinjha, R. K., J. Witherington, and K. Lee, "Place your BETs: the therapeutic potential of bromodomains," *Trends Pharmacol Sci* 33(3):146-53 (2012).

Autoimmune diseases, which are often chronic and debilitating, are a result of a dysregulated immune response, which leads the body to attack its own cells, tissues, and organs. Pro-inflammatory cytokines including IL-1β, TNF-α, IL-6, MCP-1, and IL-17 are overexpressed in autoimmune disease. IL-17 expression defines the T cell subset known as Th17 cells, which are differentiated, in part, by IL-6, and drive many of the pathogenic consequences of autoimmune disease. Thus, the IL-6/Th17 axis represents an important, potentially druggable target in autoimmune disease therapy. Kimura, A. and T. Kishimoto, "IL-6: regulator of Treg/Th17 balance," *Eur J Immunol* 40(7):1830-5 (2010). BET inhibitors are expected to have anti-inflammatory and immunomodulatory properties. Belkina, A. C. and G. V. Denis, "BET domain co-regulators in obesity, inflammation and cancer," *Nat Rev Cancer* 12(7):465-77 (2012); Prinjha, R. K., J. Witherington, and K. Lee, "Place your BETs: the therapeutic potential of bromodomains," *Trends PharmacolSci* 33(3):146-53 (2012). BET inhibitors have been shown to have a broad spectrum of anti-inflammatory effects in vitro including the ability to decrease expression of pro-inflammatory cytokines such as IL-1β, MCP-1, TNF-α, and IL-6 in activated immune cells. Mirguet, O., et al., "From ApoAI upregulation to BET family bromodomain inhibition: discovery of I-BET151," *Bioorg Med Chem Lett* 22(8):2963-7 (2012); Nicodeme, E., et al., "Suppression of inflammation by a synthetic histone mimic," *Nature* 468 (7327):1119-23 (2010); Seal, J., et al., "Identification of a novel series of BET family bromodomain inhibitors: binding mode and profile of I-BET151 (GSK1210151A)," *Bioorg Med Chem Lett* 22(8):2968-72 (2012). The mechanism for these anti-inflammatory effects may involve BET inhibitor disruption of Brd4 co-activation of NF-κB-regulated pro-inflammatory cytokines and/or displacement of BET proteins from cytokine promoters, including IL-6. Nicodeme, E., et al., "Suppression of inflammation by a synthetic histone mimic," *Nature* 468(7327):1119-23 (2010); Zhang, G., et al., "Down-regulation of NF-kappaB Transcriptional Activity in HIVassociated Kidney Disease by BRD4 Inhibition," *J Biol Chem,* 287(34):8840-51 (2012); Zhou, M., et al., "Bromodomain protein Brd4 regulates human immunodeficiency virus transcription through phosphorylation of CDK9 at threonine 29," *J Virol* 83(2):1036-44 (2009). In addition, because Brd4 is involved in T-cell lineage differentiation, BET inhibitors may be useful in inflammatory disorders characterized by specific programs of T cell differentiation. Zhang, W. S., et al., "Bromodomain-Containing-Protein 4 (BRD4) Regulates RNA Polymerase II Serine 2 Phosphorylation in Human CD4+ T Cells," *J Biol Chem* (2012).

The anti-inflammatory and immunomodulatory effects of BET inhibition have also been confirmed in vivo. A BET inhibitor prevented endotoxin- or bacterial sepsis-induced death and cecal ligation puncture-induced death in mice, suggesting utility for BET inhibitors in sepsis and acute inflammatory disorders. Nicodeme, E., et al., "Suppression of inflammation by a synthetic histone mimic," *Nature* 468(7327):1119-23 (2010). A BET inhibitor has been shown to ameliorate inflammation and kidney injury in HIV-1 transgenic mice, an animal model for HIV-associated nephropathy, in part through inhibition of Brd4 interaction with NF-κB. Zhang, G., et al., "Down-regulation of NF-kappaB Transcriptional Activity in HIV associated Kidney Disease by BRD4 Inhibition," *J Biol Chem* 287(34):8840-51 (2012). The utility of BET inhibition in autoimmune disease was demonstrated in a mouse model of multiple sclerosis, where BET inhibition resulted in abrogation of clinical signs of disease, in part, through inhibition of IL-6 and IL-17. R. Jahagirdar, S. M. et al., "An Orally Bioavailable Small Molecule RVX-297 Significantly Decreases Disease in a Mouse Model of Multiple Sclerosis," *World Congress of Inflammation*, Paris, France (2011). These results were supported in a similar mouse model where it was shown that treatment with a BET inhibitor inhibited T cell differentiation into pro-autoimmune Th1 and Th17 subsets in vitro, and further abrogated disease induction by pro-inflammatory Th1 cells. Bandukwala, H. S., et al., "Selective inhibition of CD4+ T-cell cytokine production and autoimmunity by BET protein and c-Myc inhibitors," *Proc Natl Acad Sci USA* 109(36):14532-7 (2012).

BET inhibitors may be useful in the treatment of a variety of chronic autoimmune inflammatory conditions. Thus, one aspect of the invention provides compounds, compositions, and methods for treating autoimmune and/or inflammatory diseases by administering one or more compounds of the invention or pharmaceutical compositions comprising one or more of those compounds. Examples of autoimmune and inflammatory diseases, disorders, and syndromes that may be treated using the compounds and methods of the invention include but are not limited to, inflammatory pelvic disease, urethritis, skin sunburn, sinusitis, pneumonitis, encephalitis, meningitis, myocarditis, nephritis (Zhang, G., et al., "Down-regulation of NF-kappaB Transcriptional Activity in HIVassociated Kidney Disease by BRD4 Inhibition," *J Biol Chem* 287(34):8840-51 (2012)), osteomyelitis, myositis, hepatitis, gastritis, enteritis, dermatitis, gingivitis, appendicitis, pancreatitis, cholecystitis, agammaglobulinemia, psoriasis, allergy, Crohn's disease, irritable bowel syndrome, ulcerative colitis (Prinjha, R. K., J. Witherington, and K. Lee, "Place your BETs: the therapeutic potential of bromodomains," *Trends Pharmacol Sci* 33(3):146-53 (2012)), Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis (Bandukwala, H. S., et al., "Selective inhibition of CD4+ T-cell cytokine production and autoimmunity by BET protein and c-Myc inhibitors," *Proc Natl Acad Sci USA* 109(36):14532-7 (2012)), scleroderma, vasculitis, autoimmune hemolytic and thrombocytopenic states, Goodpasture's syndrome, atherosclerosis, Addison's disease, Parkinson's disease, Alzheimer's disease, Type I diabetes (Belkina, A. C. and G. V. Denis, "BET domain co-regulators in obesity, inflammation and cancer," *Nat Rev Cancer* 12(7):465-77 (2012)), septic shock (Zhang, G., et al., "Down-regulation of NF-kappaB Transcriptional Activity in HIVassociated Kidney Disease by BRD4 Inhibition," *J Biol Chem* 287(34):8840-51 (2012)), systemic lupus erythematosus (SLE) (Prinjha, R. K., J. Witherington, and K. Lee, "Place your BETs: the therapeutic potential of bromodomains," *Trends Pharmacol Sci* 33(3):146-53 (2012)), rheumatoid arthritis (Denis, G. V., "Bromodomain coactivators in cancer, obesity, type 2 diabetes, and inflammation," *Discov Med* 10(55):489-99 (2010)), psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, uveitis, dry eye disease, scleroderma, mycosis fungoides, and Graves' disease.

BET inhibitors may be useful in the treatment of a wide variety of acute inflammatory conditions. Thus, one aspect of the invention provides compounds, compositions, and methods for treating inflammatory conditions including but not limited to, acute gout, nephritis including lupus nephritis, vasculitis with organ involvement, such as glomerulonephritis, vasculitis, including giant cell arteritis, Wegener's granulomatosis, polyarteritis nodosa, Behcet's disease, Kawasaki disease, and Takayasu's arteritis.

BET inhibitors may be useful in the prevention and treatment of diseases or conditions that involve inflammatory responses to infections with bacteria, viruses, fungi, parasites, and their toxins, such as, but not limited to sepsis, sepsis syndrome, septic shock (Nicodeme, E., et al., "Suppression of inflammation by a synthetic histone mimic," *Nature* 468(7327):1119-23 (2010)), systemic inflammatory response syndrome (SIRS), multi-organ dysfunction syndrome, toxic shock syndrome, acute lung injury, adult respiratory distress syndrome (ARDS), acute renal failure, fulminant hepatitis, burns, post-surgical syndromes, sarcoidosis, Herxheimer reactions, encephalitis, myelitis, meningitis, malaria, and SIRS associated with viral infections, such as influenza, herpes zoster, herpes simplex, and coronavirus. Belkina, A. C. and G. V. Denis, "BET domain co-regulators in obesity, inflammation and cancer," *Nat Rev Cancer* 12(7):465-77 (2012). Thus, one aspect of the invention provides compounds, compositions, and methods for treating these inflammatory responses to infections with bacteria, viruses, fungi, parasites, and their toxins described herein.

Cancer is a group of diseases caused by dysregulated cell proliferation. Therapeutic approaches aim to decrease the numbers of cancer cells by inhibiting cell replication or by inducing cancer cell differentiation or death, but there is still significant unmet medical need for more efficacious therapeutic agents. Cancer cells accumulate genetic and epigenetic changes that alter cell growth and metabolism, promoting cell proliferation and increasing resistance to programmed cell death, or apoptosis. Some of these changes include inactivation of tumor suppressor genes, activation of oncogenes, and modifications of the regulation of chromatin structure, including deregulation of histone PTMs. Watson, J. D., "Curing 'incurable' cancer," *Cancer Discov* 1(6):477-80 (2011); Morin, R. D., et al., "Frequent mutation of histone-modifying genes in non-Hodgkin lymphoma" *Nature* 476(7360):298-303 (2011).

One aspect of the invention provides compounds, compositions, and methods for treating human cancer, including, but not limited to, cancers that result from aberrant translocation or overexpression of BET proteins (e.g., NUT midline carcinoma (NMC) (French, C. A., "NUT midline carcinoma," *Cancer Genet Cytogenet* 203(1):16-20 (2010) and B-cell lymphoma (Greenwald, R. J., et al., "E mu-BRD2 transgenic mice develop B-cell lymphoma and leukemia," *Blood* 103(4):1475-84 (2004)). NMC tumor cell growth is driven by a translocation of the Brd4 or Brd3 gene to the nutlin 1 gene. Filippakopoulos, P., et al., "Selective inhibition of BET bromodomains," *Nature* 468(7327):1067-73 (2010). BET inhibition has demonstrated potent antitumor activity in murine xenograft models of NMC, a rare but lethal form of cancer. The present disclosure provides a method for treating human cancers, including, but not limited to, cancers dependent on a member of the myc family of oncoproteins including c-myc, MYCN, and L-myc. Vita, M. and M. Henriksson, "The Myc oncoprotein as a therapeutic target for human cancer," *Semin Cancer Biol* 16(4): 318-30 (2006). These cancers include Burkitt's lymphoma, acute myelogenous leukemia, multiple myeloma, and aggressive human medulloblastoma. Vita, M. and M. Henriksson, "The Myc oncoprotein as a therapeutic target for human cancer," *Semin Cancer Biol* 16(4):318-30 (2006). Cancers in which c-myc is overexpressed may be particularly susceptible to BET protein inhibition; it has been shown that treatment of tumors that have activation of c-myc with a BET inhibitor resulted in tumor regression through inactivation of c-myc transcription. Dawson, M. A., et al., "Inhibition of BET recruitment to chromatin as an effective treatment for MLL-fusion leukaemia," *Nature* 478(7370): 529-33 (2011); Delmore, J. E., et al., "BET bromodomain inhibition as a therapeutic strategy to target c-Myc," *Cell* 146(6):904-17 (2010); Mertz, J. A., et al., "Targeting MYC dependence in cancer by inhibiting BET bromodomains," *Proc Natl Acad Sci USA* 108(40):16669-74 (2011); Ott, C. J., et al., "BET bromodomain inhibition targets both c-Myc and IL7R in highrisk acute lymphoblastic leukemia," *Blood* 120(14):2843-52 (2012); Zuber, J., et al., "RNAi screen identifies Brd4 as a therapeutic target in acute myeloid leukaemia," *Nature* 478(7370):524-8 (2011).

Embodiments of the invention include methods for treating human cancers that rely on BET proteins and pTEFb (Cdk9/CyclinT) to regulate oncogenes (Wang, S. and P. M. Fischer, "Cyclin-dependent kinase 9: a key transcriptional regulator and potential drug target in oncology, virology and cardiology," *Trends Pharmacol Sci* 29(6):302-13 (2008)), and cancers that can be treated by inducing apoptosis or senescence by inhibiting Bcl2, cyclin-dependent kinase 6 (CDK6) (Dawson, M. A., et al., "Inhibition of BET recruitment to chromatin as an effective treatment for MLL-fusion leukaemia," *Nature* 478(7370):529-33 (2011)), or human telomerase reverse transcriptase (hTERT) (Delmore, J. E., et al., "BET bromodomain inhibition as a therapeutic strategy to target c-Myc," *Cell* 146(6):904-17 (2010); Ruden, M. and N. Puri, "Novel anticancer therapeutics targeting telomerase," *Cancer Treat Rev* 39(5):444-456 (2012)).

Inhibition of BET proteins may also result in inhibition of enhancer and/or super-enhancer known to drive transcriptional programs associated with several human disease etiologies (Hnisz, D. et al. "Super-enhancers in the control of cell identity and disease," *Cell* 155:934-947 (2013); Loven, J. et al. "Selective inhibition of tumor oncogenes by disruption of super-enhancers." *Cell* 153: 320-334 (2013); Whyte, W. A. et al. "Master transcription factors and mediator establish super-enhancers at key cell identity genes," *Cell* 153:307-319 (2013)). The MYC oncogene is an example of a gene associated with a super enhancer that is disrupted by BET-bromodomain inhibitors. See, e.g., Loven (2013). Thus, one aspect of the invention provides compounds, compositions, and methods for treating such diseases and disorders, including cancers associated with a super-enhancer or enhancer that may be disrupted with a BET inhibitor.

BET inhibitors may be useful in the treatment of cancers including, but not limited to, adrenal cancer, acinic cell carcinoma, acoustic neuroma, acral lentiginous melanoma, acrospiroma, acute eosinophilic leukemia, acute erythroid leukemia, acute lymphoblastic leukemia (see, e.g., Loven (2013)), acute megakaryoblastic leukemia, acute monocytic leukemia, acute myeloid leukemia (Dawson, M. A., et al., "Inhibition of BET recruitment to chromatin as an effective treatment for MLL-fusion leukaemia," *Nature* 478(7370): 529-33 (2011); Mertz, J. A., et al., "Targeting MYC dependence in cancer by inhibiting BET bromodomains," *Proc Natl Acad Sci USA* 108(40):16669-74 (2011); Zuber, J., et al., "RNAi screen identifies Brd4 as a therapeutic target in acute myeloid leukaemia," *Nature* 478(7370):524-8 (2011)), adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma (Wu, X. et al. "Bromodomain and extraterminal (BET) protein inhibition suppresses human T cell leukemia virus 1 (HTLV-1) Tax protein-mediated tumorigenesis by inhibiting nuclear factor kappaB (NF-kappaB) signaling," *J Biol Chem* 288:36094-36105 (2013)), aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma (Knoechel, B. et al. "An epigenetic mechanism of resistance to targeted therapy in T cell acute lymphoblastic leukemia," *Nat Genet* 46:364-370 (2014); Loosveld, M. et al. "Therapeutic Targeting of c-Myc in T-Cell Acute Lymphoblastic Leukemia (T-ALL)," *Oncotarget* 5(10):3168-72 (2014); Reynolds, C. et al. "Repression of BIM mediates survival signaling by MYC and AKT in high-risk T-cell acute lymphoblastic leukemia," *Leukemia* 28(9):1819-27 (2014); Roderick, J. E. et al. "c-Myc inhibition prevents leukemia initiation in mice and impairs the growth of relapsed and induction failure pediatric T-ALL cells,*" Blood* 123:1040-1050 (2014)), angiomyolipoma, angiosarcoma, astrocytoma, atypical teratoid rhabdoid tumor, B-cell acute lymphoblastic leukemia (Ott, C. J., et al., "BET bromodomain inhibition targets both c-Myc and IL7R in highrisk acute lymphoblastic leukemia," *Blood* 120(14):2843-52 (2012)), B-cell chronic lymphocytic leukemia, B-cell prolymphocytic leukemia, B-cell lymphoma (Greenwald, R. J., et al., "E mu-BRD2 transgenic mice develop B-cell lymphoma and leukemia," *Blood* 103(4):1475-84 (2004)), basal cell carcinoma, biliary tract cancer, bladder cancer, blastoma, bone cancer (Lamoureux, F. et al. "Selective inhibition of BET bromodomain epigenetic signalling interferes with the bone-associated tumour vicious cycle," *Nature Comm* 5:3511 (2014), Brenner tumor, Brown tumor, Burkitt's lymphoma (Mertz, J. A., et al., "Targeting MYC dependence in cancer by inhibiting BET bromodomains," *Proc Natl Acad Sci USA* 108(40):16669-74 (2011)), breast cancer (Feng, Q. et al. "An epigenomic approach to therapy for tamoxifen-resistant breast cancer," *Cell Res* 24:809-819 (2014); Nagarajan, S. et al. "Bromodomain Protein BRD4 is Required for Estrogen Receptor-Dependent Enhancer Activation and Gene Transcription," *Cell Rep* 8:460-469 (2014); Shi, J. et al. "Disrupting the Interaction of BRD4 with Diacetylated Twist Suppresses Tumorigenesis in Basal-like Breast Cancer," *Cancer Cell* 25:210-225 (2014)), brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma (Chapuy, B. et al. "Discovery and characterization of super-enhancer-associated dependencies in diffuse large B cell lymphoma," *Cancer Cell* 24:777-790 (2013); Trabucco, S. E. et al. "Inhibition of bromodomain proteins for the treatment of human diffuse large B-cell lymphoma," *Clin Can Res* 21(1):113-122 (2015); Ceribelli, M. et al. "Blockade of oncogenic IkappaB kinase activity in diffuse large B-cell lymphoma by bromodomain and extra-terminal domain protein inhibitors," *PNAS* 111:11365-11370 (2014)), dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme (Cheng, Z et al. "Inhibition of BET bromodomain targets genetically diverse glioblastoma," *Clin Can Res* 19:1748-1759 (2013); Pastori, C. et al. "BET bromodomain proteins are required for glioblastoma cell proliferation," *Epigenetics* 9:611-620 (2014)), glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma (Lwin, T. et al. "A microenvironment-mediated c-Myc/miR-548m/HDAC6 amplification loop in non-Hodgkin B cell lymphomas," *J Clin Invest* 123:4612-4626 (2013)), invasive lobular carcinoma, intestinal cancer, kidney cancer, laryngeal cancer, lentigo maligna, lethal midline carcinoma, leukemia, Leydig cell tumor, liposarcoma, lung cancer, lymphangioma, lymphangiosarcoma, lymphoepithelioma, lymphoma, acute lymphocytic leukemia, acute myelogenous leukemia (Mertz, J. A., et al., "Targeting MYC dependence in cancer by inhibiting BET bromodomains," *Proc Natl Acad Sci USA* 108 (40):16669-74 (2011)), chronic lymphocytic leukemia, liver cancer, small cell lung cancer, non-small cell lung cancer (Lockwood, W. W. et al. "Sensitivity of human lung adenocarcinoma cell lines to targeted inhibition of BET epigenetic signaling proteins," *PNAS* 109:19408-19413 (2012); Shimamura, T. et al. "Efficacy of BET bromodomain inhibition in Kras-mutant non-small cell lung cancer," *Clin Can Res* 19:6183-6192 (2013)) MALT lymphoma, malignant fibrous histiocytoma, malignant peripheral nerve sheath tumor (Baude, A. et al. "PRC2 loss amplifies Ras signaling in cancer," *Nat Genet* 46:1154-1155 (2014); Patel, A. J. et al. "BET bromodomain inhibition triggers apoptosis of NF1-associated malignant peripheral nerve sheath tumors through Bim induction," *Cell Rep* 6:81-92 (2014)), malignant triton tumor, mantle cell lymphoma (Moros, A. et al. "Synergistic antitumor activity of lenalidomide with the BET bromodomain inhibitor CP1203 in bortezomib-resistant mantle cell lymphoma," *Leukemia* 28:2049-2059 (2014)), marginal zone B-cell lymphoma, mast cell leukemia, mediastinal germ cell tumor, medullary carcinoma of the breast, medullary thyroid cancer, medulloblastoma (Bandopadhayay, P. et al. "BET bromodomain inhibition of MYC-amplified medulloblastoma," *Clin Can Res* 20:912-925 (2014); Henssen, A. G. et al. "BET bromodomain protein inhibition is a therapeutic option for medulloblastoma" *Oncotarget* 4(11):2080-2089 (2013); Long, J. et al. "The BET bromodomain inhibitor I-BET151 acts downstream of Smoothened to abrogate the growth of Hedgehog driven cancers," *J Biol Chem* 289(51):35494-35502 (2014); Tang, Y. et al. "Epigenetic targeting of Hedgehog pathway transcriptional output through BET bromodomain inhibition," *Nat Med* 20(7):732-40 (2014); Venataraman, S. et al. "Inhibition of BRD4 attenuates tumor cell self-renewal and suppresses stem cell signaling in MYC driven medulloblastoma," *Oncotarget* 5(9):2355-71 (2014)) melanoma (Segura et al, "BRD4 is a novel therapeutic target in melanoma," *Cancer Res* 72(8): Supplement 1 (2012)), meningioma, Merkel cell cancer, mesothelioma, metastatic urothelial carcinoma, mixed Mullerian tumor, mixed lineage leukemia (Dawson, M. A., et al., "Inhibition of BET recruitment to chromatin as an effective treatment for MLL-fusion leukaemia," *Nature* 478(7370):529-33 (2011)), mucinous tumor, multiple myeloma (Delmore, J. E., et al., "BET bromodomain inhibition as a therapeutic strategy to target c-Myc," *Cell* 146(6):904-17 (2010)), muscle tissue neoplasm, mycosis fungoides, myxoid liposarcoma, myxoma, myxosarcoma, nasopharyngeal carcinoma, neurinoma, neuroblastoma (Puissant, A. et al. "Targeting MYCN in neuroblastoma by BET bromodomain inhibition," *Cancer Discov* 3:308-323 (2013); Wyce, A. et al. "BET inhibition silences expression of MYCN and BCL2 and induces cytotoxicity in neuroblastoma tumor models," *PLoS One* 8:e72967 (2014)), neurofibroma, neuroma, nodular melanoma, NUT-midline carcinoma (Filippakopoulos, P., et al., "Selective inhibition of BET bromodomains," *Nature* 468 (7327):1067-73 (2010)), ocular cancer, oligoastrocytoma, oligodendroglioma, oncocytoma, optic nerve sheath meningioma, optic nerve tumor, oral cancer, osteosarcoma (Lamoureux, F. et al. "Selective inhibition of BET bromodomain epigenetic signalling interferes with the bone-associated tumour vicious cycle" *Nat Commun* 5:3511 (2014); Lee, D. H. et al. "Synergistic effect of JQ1 and rapamycin for treatment of human osteosarcoma," *Int J Cancer* 136(9): 2055-2064 (2014)), ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma (Tolani, B. et al. "Targeting Myc in KSHV-associated primary effusion lymphoma with BET bromodomain inhibitors," *Oncogene* 33:2928-2937 (2014)), primary peritoneal cancer, prostate cancer (Asangani, I. A. et al. "Therapeutic targeting of BET bromodomain proteins in castration-resistant prostate cancer," *Nature* 510:278-282 (2014); Cho, H. et al. "RapidCaP, a novel GEM model for metastatic prostate cancer analysis and therapy, reveals myc as a driver of Pten-mutant metastasis," *Cancer Discov* 4:318-333 (2014); Gao, L. et al. "Androgen receptor promotes ligand-independent prostate cancer progression through c-Myc upregulation," *PLoS One* 8:e63563 (2013): Wyce, A. et al. "Inhibition of BET bromodomain proteins as a therapeutic approach in prostate cancer," *Oncotarget* 4:2419-2429 (2013)), pancreatic cancer (Sahai, V. et al. "BET bromodomain inhibitors block growth of pancreatic cancer cells in three-dimensional collagen," *Mol Cancer Ther* 13:1907-1917 (2014)), pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor. Thus, one aspect of the inventions provides compounds, compositions, and methods for treating such cancers.

BET inhibitors of the invention may be useful in the treatment of cancers that are resistant to current and future cancer treatments, as BET proteins are involved in the mechanisms of resistance of several anti-cancer treatment, including chemotherapy (Feng, Q., et al. "An epigenomic approach to therapy for tamoxifen-resistant breast cancer" *Cell Res* 24:809-819 (2014)), immunotherapy (Emadali, A., et al. "Identification of a novel BET bromodomain inhibitor-sensitive, gene regulatory circuit that controls Rituximab response and tumour growth in aggressive lymphoid cancers," *EMBO Mol Med* 5:1180-1195 (2013))., hormone-deprivation therapies (Asangani, I. A. et al. "Therapeutic targeting of BET bromodomain proteins in castration-resistant prostate cancer," *Nature* 510:278-282 (2014)), or other molecules ((Knoechel, B. et al. "An epigenetic mechanism of resistance to targeted therapy in T cell acute lymphoblastic leukemia," *Nat Genet* 46:364-370 (2014)). In these instances, the BET proteins are involved in the resistance mechanism to the cancer therapy, and treatment with a BET inhibitor could either restore sensitivity to the treatment, inhibit proliferation or induce cell death or senescence, either alone or in combination with other therapies (Moros, A. et al. "Synergistic antitumor activity of lenalidomide with the BET bromodomain inhibitor CPI203 in bortezomib-resistant mantle cell lymphoma," *Leukemia* 28:2049-2059 (2014)).

BET inhibitors may be useful in the treatment of benign proliferative and fibrotic disorders, including benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, juvenile polyposis syndrome, idiopathic pulmonary fibrosis, renal fibrosis, post-operative stricture, keloid formation, scleroderma, and cardiac fibrosis. Tang, X. et al., "Assessment of Brd4 Inhibition in Idiopathic Pulmonary Fibrosis Lung Fibroblasts and in Vivo Models of Lung Fibrosis," *Am J Pathology* 183(2):470-479 (2013). Thus, one aspect of the invention provides compounds, compositions, and methods for treating such benign proliferative and fibrotic disorders.

Cardiovascular disease (CVD) is the leading cause of mortality and morbidity in the United States. Roger, V. L., et al., "Heart disease and stroke statistics—2012 update: a report from the American Heart Association," *Circulation* 125(1):e2-e220 (2012). Atherosclerosis, an underlying cause of CVD, is a multifactorial disease characterized by dyslipidemia and inflammation. BET inhibitors are expected to be efficacious in atherosclerosis and associated conditions because of aforementioned anti-inflammatory effects as well as ability to increase transcription of ApoA-I, the major constituent of HDL. Mirguet, O., et al., "From ApoAI upregulation to BET family bromodomain inhibition: discovery of 1-BET151," *Bioorg Med Chem Lett* 22(8):2963-7 (2012); Chung, C. W., et al., "Discovery and characterization of small molecule inhibitors of the BET family bromodomains," *J Med Chem* 54(11):3827-38 (2011). Accordingly, one aspect of the invention provides compounds, compositions, and methods for treating cardiovascular disease, including but not limited to atherosclerosis.

Up-regulation of ApoA-1 is considered to be a useful strategy in treatment of atherosclerosis and CVD. Degoma, E. M. and D. J. Rader, "Novel HDL-directed pharmacotherapeutic strategies," *Nat Rev* Cardiol 8(5):266-77 (2011). BET inhibitors have been shown to increase ApoA-I transcription and protein expression. Mirguet, O., et al., "From ApoAI upregulation to BET family bromodomain inhibition: discovery of I-BET151," *Bioorg Med Chem Lett* 22(8):2963-7 (2012); Chung, C. W., et al., "Discovery and characterization of small molecule inhibitors of the BET family bromodomains," *J Med Chem* 54(11):3827-38 (2011). It has also been shown that BET inhibitors bind directly to BET proteins and inhibit their binding to acetylated histones at the ApoA-1 promoter, suggesting the presence of a BET protein repression complex on the ApoA-1 promoter, which can be functionally disrupted by BET inhibitors. It follows that, BET inhibitors may be useful in the treatment of disorders of lipid metabolism via the regulation of ApoA-I and HDL such as hypercholesterolemia, dyslipidemia, atherosclerosis (Degoma, E. M. and D. J. Rader, "Novel HDL-directed pharmacotherapeutic strategies," *Nat Rev* Cardiol 8(5):266-77 (2011)), and Alzheimer's disease and other neurological disorders. Elliott, D. A., et al., "Apolipoproteins in the brain: implications for neurological and psychiatric disorders," *Clin Lipidol* 51(4):555-573 (2010). Thus, one aspect of the invention provides compounds, compositions, and methods for treating cardiovascular disorders by upregulation of ApoA-1.

BET inhibitors may be useful in the prevention and treatment of conditions associated with ischemia-reperfusion injury such as, but not limited to, myocardial infarction, stroke, acute coronary syndromes (Prinjha, R. K., J. Witherington, and K. Lee, "Place your BETs: the therapeutic potential of bromodomains," *Trends PharmacolSci* 33(3): 146-53 (2012)), renal reperfusion injury, organ transplantation, coronary artery bypass grafting, cardio-pulmonary bypass procedures, hypertension, pulmonary, renal, hepatic, gastro-intestinal, or peripheral limb embolism. Accordingly, one aspect of the invention provides compounds, compositions, and methods for prevention and treatment of conditions described herein that are associated with ischemia-reperfusion injury.

Obesity-associated inflammation is a hallmark of type II diabetes, insulin resistance, and other metabolic disorders. Belkina, A. C. and G. V. Denis, "BET domain co-regulators in obesity, inflammation and cancer," *Nat Rev Cancer* 12(7): 465-77 (2012); Denis, G. V., "Bromodomain coactivators in cancer, obesity, type 2 diabetes, and inflammation," *Discov Med* 10(55):489-99 (2010). Consistent with the ability of BET inhibitors to inhibit inflammation, gene disruption of Brd2 in mice ablates inflammation and protects animals from obesity-induced insulin resistance. Wang, F., et al., "Brd2 disruption in mice causes severe obesity without Type 2 diabetes," *Biochem J* 425(1):71-83 (2010). It has been shown that Brd2 interacts with PPARγ and opposes its transcriptional function. Knockdown of Brd2 in vitro promotes transcription of PPARγ-regulated networks, including those controlling adipogenesis. Denis, G. V., et al, "An emerging role for bromodomain-containing proteins in chromatin regulation and transcriptional control of adipogenesis," *FEBS Lett* 584(15):3260-8 (2010). In addition Brd2 is highly expressed in pancreatic β-cells and regulates proliferation and insulin transcription. Wang, F., et al., "Brd2 disruption in mice causes severe obesity without Type 2 diabetes," *Biochem J* 425(1):71-83 (2010). Taken together, the combined effects of BET inhibitors on inflammation and metabolism decrease insulin resistance and may be useful in the treatment of pre-diabetic and type II diabetic individuals as well as patients with other metabolic complications. Belkina, A. C. and G. V. Denis, "BET domain co-regulators in obesity, inflammation and cancer," *Nat Rev Cancer* 12(7): 465-77 (2012). Accordingly, one aspect of the invention provides compounds, compositions, and methods for treatment and prevention of metabolic disorders, including but not limited to obesity-associated inflammation, type II diabetes, and insulin resistance.

BET inhibitors may be useful in the prevention and treatment of episome-based DNA viruses including, but not limited to, human papillomavirus, herpes virus, Epstein-Barr virus, human immunodeficiency virus (Belkina, A. C. and G. V. Denis, "BET domain co-regulators in obesity, inflammation and cancer," *Nat Rev Cancer* 12(7):465-77 (2012)), adenovirus, poxvirus, hepatitis B virus, and hepatitis C virus. Host-encoded BET proteins have been shown to be important for transcriptional activation and repression of viral promoters. Brd4 interacts with the E2 protein of human papilloma virus (HPV) to enable E2 mediated transcription of E2-target genes. Gagnon, D., et al., "Proteasomal degradation of the papillomavirus E2 protein is inhibited by overexpression of bromodomain-containing protein 4," *J Virol* 83(9):4127-39 (2009). Similarly, Brd2, Brd3, and Brd4 all bind to latent nuclear antigen 1 (LANAI), encoded by Kaposi's sarcoma-associated herpes virus (KSHV), promoting LANA1-dependent proliferation of KSHV-infected cells. You, J., et al., "Kaposi's sarcoma-associated herpesvirus latency-associated nuclear antigen interacts with bromodomain protein Brd4 on host mitotic chromosomes," *J Virol* 80(18):8909-19 (2006). A BET inhibitor has been shown to inhibit the Brd4-mediated recruitment of the transcription elongation complex pTEFb to the Epstein-Barr virus (EBV) viral C promoter, suggesting therapeutic value for EBV-associated malignancies. Palermo, R. D., et al., "RNA polymerase II stalling promotes nucleosome occlusion and pTEFb recruitment to drive immortalization by Epstein-Barr virus," *PLoS Pathog* 7(10):e1002334 (2011). Also, a BET inhibitor reactivated HIV in models of latent T cell infection and latent monocyte infection, potentially allowing for viral eradication by complementary anti-retroviral therapy. Zhu, J., et al., "Reactivation of Latent HIV-1 by Inhibition of BRD4," *Cell Rep* 2(4):807-816 (2012); Banerjee, C., et al., "BET bromodomain inhibition as a novel strategy for reactivation of HIV-1," *J Leukoc Biol* 92(6):1147-1154 (2012); Bartholomeeusen, K., et al., "BET bromodomain inhibition activates transcription via a transient release of P-TEFb from 7SK snRNP," *J Biol Chem* 287(43):36609-36616 (2012); Li, Z., et al., "The BET bromodomain inhibitor JQ1 activates HIV latency through antagonizing Brd4 inhibition of Tat-transactivation," *Nucleic Acids Res* (2012). Thus, the invention also provides compounds, compositions, and methods for treatment and prevention of episome-based DNA virus infections. In particular, one aspect of the invention provides compounds, compositions, and methods for treatment and/or prevention of a viral infection, including, but not limited to infection by HPV, KSHV, EBV, HIV, HBV, HCV, adenovirus, poxvirus herpes virus, or a malignancy associated with that infection.

Some central nervous system (CNS) diseases are characterized by disorders in epigenetic processes. Brd2 haploinsufficiency has been linked to neuronal deficits and epilepsy. Velisek, L., et al., "GABAergic neuron deficit as an idiopathic generalized epilepsy mechanism: the role of BRD2 haploinsufficiency in juvenile myoclonic epilepsy," *PLoS One* 6(8): e23656 (2011). SNPs in various bromodomain-containing proteins have also been linked to mental disorders including schizophrenia and bipolar disorders. Prinjha, R. K., J. Witherington, and K. Lee, "Place your BETs: the therapeutic potential of bromodomains," *Trends Pharmacol Sci* 33(3):146-53 (2012). In addition, the ability of BET inhibitors to increase ApoA-I transcription may make BET inhibitors useful in Alzheimer's disease therapy considering the suggested relationship between increased ApoA-I and Alzheimer's disease and other neurological disorders. Elliott, D. A., et al., "Apolipoproteins in the brain: implications for neurological and psychiatric disorders," *Clin Lipidol* 51(4):555-573 (2010). Accordingly, one aspect of the invention provides compounds, compositions, and methods for treating such CNS diseases and disorders.

BRDT is the testis-specific member of the BET protein family which is essential for chromatin remodeling during spermatogenesis. Gaucher, J., et al., "Bromodomain-dependent stage-specific male genome programming by Brdt," *EMBO J* 31(19):3809-20 (2012); Shang, E., et al., "The first bromodomain of Brdt, a testis-specific member of the BET sub-family of double-bromodomain-containing proteins, is essential for male germ cell differentiation," *Development* 134(19):3507-15 (2007). Genetic depletion of BRDT or inhibition of BRDT interaction with acetylated histones by a BET inhibitor resulted in a contraceptive effect in mice, which was reversible when small molecule BET inhibitors were used. Matzuk, M. M., et al., "Small-Molecule Inhibition of BRDT for Male Contraception," *Cell* 150(4):673-684 (2012); Berkovits, B. D., et al., "The testis-specific double bromodomain-containing protein BRDT forms a complex with multiple spliceosome components and is required for mRNA splicing and 3'-UTR truncation in round spermatids," *Nucleic Acids Res* 40(15):7162-75 (2012). These data suggest potential utility of BET inhibitors as a novel and efficacious approach to male contraception. Thus, another aspect of the invention provides compounds, compositions, and methods for male contraception.

Monocyte chemotactic protein-1 (MCP-1, CCL2) plays an important role in cardiovascular disease. Niu, J. and P. E. Kolattukudy, "Role of MCP-1 in cardiovascular disease: molecular mechanisms and clinical implications," *Clin Sci* (Lond) 117(3):95-109 (2009). MCP-1, by its chemotactic activity, regulates recruitment of monocytes from the arterial lumen to the subendothelial space, where they develop into macrophage foam cells, and initiate the formation of fatty streaks which can develop into atherosclerotic plaque. Dawson, J., et al., "Targeting monocyte chemoattractant protein-1 signalling in disease," *Expert Opin Ther Targets* 7(1):35-48 (2003). The critical role of MCP-1 (and its cognate receptor CCR2) in the development of atherosclerosis has been examined in various transgenic and knockout mouse models on a hyperlipidemic background. Boring, L., et al., "Decreased lesion formation in CCR2−/− mice reveals a role for chemokines in the initiation of atherosclerosis," *Nature* 394(6696):894-7 (1998); Gosling, J., et al., "MCP-1 deficiency reduces susceptibility to atherosclerosis in mice that overexpress human apolipoprotein B," *J Clin Invest* 103(6):773-8 (1999); Gu, L., et al., "Absence of monocyte chemoattractant protein-1 reduces atherosclerosis in low density lipoprotein receptor-deficient mice," *Mol Cell* 2(2): 275-81 (1998); Aiello, R. J., et al., "Monocyte chemoattractant protein-1 accelerates atherosclerosis in apolipoprotein E-deficient mice," *Arterioscler Thromb Vasc Biol* 19(6): 1518-25 (1999). These reports demonstrate that abrogation of MCP-1 signaling results in decreased macrophage infiltration to the arterial wall and decreased atherosclerotic lesion development.

The association between MCP-1 and cardiovascular disease in humans is well-established. Niu, J. and P. E. Kolattukudy, "Role of MCP-1 in cardiovascular disease: molecular mechanisms and clinical implications," *Clin Sci* (Lond) 117(3):95-109 (2009). MCP-1 and its receptor are overexpressed by endothelial cells, smooth muscle cells, and infiltrating monocytes/macrophages in human atherosclerotic plaque. Nelken, N. A., et al., "Monocyte chemoattractant protein-1 in human atheromatous plaques," *J Clin Invest* 88(4):1121-7 (1991). Moreover, elevated circulating levels of MCP-1 are positively correlated with most cardiovascular risk factors, measures of coronary atherosclerosis burden, and the incidence of coronary heart disease (CHD). Deo, R., et al., "Association among plasma levels of monocyte chemoattractant protein-1, traditional cardiovascular risk factors, and subclinical atherosclerosis," *J Am Coll Cardiol* 44(9):1812-8 (2004). CHD patients with among the highest levels of MCP-1 are those with acute coronary syndrome (ACS). de Lemos, J. A., et al., "Association between plasma levels of monocyte chemoattractant protein-1 and long-term clinical outcomes in patients with acute coronary syndromes," *Circulation* 107(5):690-5 (2003). In addition to playing a role in the underlying inflammation associated with CHD, MCP-1 has been shown to be involved in plaque rupture, ischemic/reperfusion injury, restenosis, and heart transplant rejection. Niu, J. and P. E. Kolattukudy, "Role of MCP-1 in cardiovascular disease: molecular mechanisms and clinical implications," *Clin Sci* (Lond) 117(3):95-109 (2009).

MCP-1 also promotes tissue inflammation associated with autoimmune diseases including rheumatoid arthritis (RA) and multiple sclerosis (MS). MCP-1 plays a role in the infiltration of macrophages and lymphocytes into the joint in RA, and is overexpressed in the synovial fluid of RA patients. Koch, A. E., et al., "Enhanced production of monocyte chemoattractant protein-1 in rheumatoid arthritis," *J Clin Invest* 90(3):772-9 (1992). Blockade of MCP-1 and MCP-1 signaling in animal models of RA have also shown the importance of MCP-1 to macrophage accumulation and proinflammatory cytokine expression associated with RA. Brodmerkel, C. M., et al., "Discovery and pharmacological characterization of a novel rodent-active CCR2 antagonist, INCB3344," *J Immunol* 175(8):5370-8 (2005); Bruhl, H., et al., "Dual role of CCR2 during initiation and progression of collagen-induced arthritis: evidence for regulatory activity of CCR2+ T cells," *J Immunol* 172(2):890-8 (2004); Gong, J. H., et al., "An antagonist of monocyte chemoattractant protein 1 (MCP-1) inhibits arthritis in the MRL-lpr mouse model," *J Exp Med* 186(1):131-7 (1997); 65. Gong, J. H., et al., "Post-onset inhibition of murine arthritis using combined chemokine antagonist therapy," *Rheumatology* (Oxford) 43(1): 39-42 (2004).

Overexpression of MCP-1, in the brain, cerebrospinal fluid (CSF), and blood, has also been associated with chronic and acute MS in humans. Mahad, D. J. and R. M. Ransohoff, "The role of MCP-1 (CCL2) and CCR2 in multiple sclerosis and experimental autoimmune encephalomyelitis (EAE)," *Semin Immunol* 15(1):23-32 (2003). MCP-1 is overexpressed by a variety of cell types in the brain during disease progression and contributes to the infiltration of macrophages and lymphocytes which mediate the tissue damage associated with MS. Genetic depletion of MCP-1 or CCR2 in the experimental autoimmune encephalomyelitis (EAE) mouse model, a model resembling human MS, results in resistance to disease, primarily because of decreased macrophage infiltration to the CNS. Fife, B. T., et al., "CC chemokine receptor 2 is critical for induction of experimental autoimmune encephalomyelitis," *J Exp Med* 192(6):899-905 (2000); Huang, D. R., et al., "Absence of monocyte chemoattractant protein 1 in mice leads to decreased local macrophage recruitment and antigen-specific T helper cell type 1 immune response in experimental autoimmune encephalomyelitis," *J Exp Med* 193(6):713-26 (2001).

Preclinical data have suggested that small- and large-molecule inhibitors of MCP-1 and CCR2 have potential as therapeutic agents in inflammatory and autoimmune indications. Thus, one aspect of the invention provides compounds, compositions, and methods for treating cardiovascular, inflammatory, and autoimmune conditions associated with MCP-1 and CCR2.

Accordingly, the invention provides compounds that are useful for inhibition of BET protein function by binding to bromodomains, pharmaceutical compositions comprising one or more of those compounds, and use of these compounds or compositions in the treatment and prevention of diseases and conditions, including, but not limited to, cancer, autoimmune, and cardiovascular diseases.

One embodiment of the invention provides compounds of Formula I and methods of administering a therapeutically effective amount of those compounds to a mammal (e.g., a human) in need thereof:

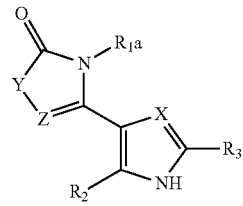

Formula I or a stereoisomer, tautomer, pharmaceutically acceptable salt, or hydrate thereof, wherein:

X is selected from CH and N;
Y is selected from —NH, —NR$_{1b}$ and oxygen;
Z is selected from N, and —CH—;
R$_{1a}$ and R$_{1b}$ are independently selected from alkyl (C$_1$-C$_6$), carbocycle (C$_3$-C$_{10}$), heterocycle (C$_2$-C$_{10}$) optionally substituted with 1 to 3 groups selected from R$_4$;
R$_2$ is selected from aryl (C$_5$-C$_{10}$) and heteroaryl (C$_5$-C$_{10}$) optionally substituted with 1 to 5 groups selected from R$_5$;
R$_3$ is selected from carbocycle (C$_3$-C$_{10}$) and heterocycle (C$_2$-C$_{10}$) optionally substituted with 1 to 5 groups selected from R$_5$;
each R$_4$ is independently selected from deuterium, alkyl (C$_1$-C$_6$) (such as methyl, ethyl, propyl, isopropyl, butyl), cycloalkyl (C$_3$-C$_8$) (such as cyclopropyl, cyclobutyl, cyclopentyl, cyclohexyl); alkoxy (C$_1$-C$_6$) (such as methoxy, ethoxy, isopropoxy), amino (such as —NH$_2$, —NHMe, —NHEt, —NHiPr, —NHBu-NMe$_2$, NMeEt, —NEt$_2$, —NEtBu), —NHC(O)NH-alkyl(C$_1$-C$_6$), halogen (such as F, Cl), amide (such as —NHC(O)Me, —NHC(O)Et, —C(O)NHMe, —C(O)NEt$_2$, —C(O)NiPr), —CF$_3$, —CN, —N$_3$, ketone (such as acetyl, —C(O)Et, —C(O)Pr), —S(O)-alkyl(C$_1$-C$_4$) (such as —S(O)Me, —S(O)Et), —SO$_2$-alkyl(C$_1$-C$_6$) (such as —SO$_2$Me, —SO$_2$Et, —SO$_2$Pr), thioalkyl(C$_1$-C$_6$) (such as —SMe, —SEt, —SPr, —SBu), —COOH, and ester (such as —C(O)OMe, —C(O)OEt, —C(O)OBu), each of which may be optionally substituted with hydrogen, F, Cl, Br, —OH, —NH$_2$, —NHMe, —OMe, —SMe, oxo, and/or thio-oxo; and each R$_5$ is independently selected from deuterium, alkyl (C$_1$-C$_6$) (such as methyl, ethyl, propyl, isopropyl, butyl), alkoxy (C$_1$-C$_6$) (such as methoxy, ethoxy, isopropoxy), amino (such as —NH$_2$, —NHMe, —NHEt, —NHiPr, —NHBu-NMe$_2$, NMeEt, —NEt$_2$, —NEtBu), —NHC(O)NH— alkyl(C$_1$-C$_6$), halogen (such as F, Cl), amide (such as —NHC(O)Me, —NHC(O)Et, —C(O)NHMe, —C(O)NEt$_2$, —C(O)NiPr), —CF$_3$, —CN, —N$_3$, ketone (such as acetyl, —C(O)Et, —C(O)Pr), —S(O)- alkyl($C_1$-$C_4$) (such as —S(O)Me, —S(O)Et), —$SO_2$-alkyl($C_1$-$C_6$) (such as —$SO_2$Me, —$SO_2$Et, —$SO_2$Pr), thioalkyl($C_1$-$C_6$) (such as —SMe, —SEt, —SPr, —SBu), —COOH, and ester (such as —C(O)OMe, —C(O)OEt, —C(O)OBu), each of which may be optionally substituted with hydrogen, F, Cl, Br, —OH, —$NH_2$, —NHMe, —OMe, —SMe, oxo, and/or thio-OXO.

In another aspect of the invention, a pharmaceutical composition comprising a compound of Formula I, or a pharmaceutically acceptable salt thereof and one or more pharmaceutically acceptable carriers, diluents or excipients is provided.

In yet another aspect of the invention there is provided a compound of Formula I, or a pharmaceutically acceptable salt thereof for use in therapy, in particular in the treatment of diseases or conditions for which a bromodomain inhibitor is indicated.

In yet another aspect of the invention there is provided a compound of Formula I, or a pharmaceutically acceptable salt thereof in the manufacture of a medicament for the treatment of diseases or conditions for which a bromodomain inhibitor is indicated.

Definitions

As used in the present specification, the following words, phrases and symbols are generally intended to have the meanings as set forth below, except to the extent that the context in which they are used indicates otherwise. The following abbreviations and terms have the indicated meanings throughout.

As used herein, "cardiovascular disease" refers to diseases, disorders and conditions of the heart and circulatory system that are mediated by BET inhibition. Exemplary cardiovascular diseases, including cholesterol- or lipid-related disorders, include, but are not limited to, acute coronary syndrome, angina, arteriosclerosis, atherosclerosis, carotid atherosclerosis, cerebrovascular disease, cerebral infarction, congestive heart failure, congenital heart disease, coronary heart disease, coronary artery disease, coronary plaque stabilization, dyslipidemias, dyslipoproteinemias, endothelium dysfunctions, familial hypercholesterolemia, familial combined hyperlipidemia, hypoalphalipoproteinemia, hypertriglyceridemia, hyperbetalipoproteinemia, hypercholesterolemia, hypertension, hyperlipidemia, intermittent claudication, ischemia, ischemia reperfusion injury, ischemic heart diseases, cardiac ischemia, metabolic syndrome, multi-infarct dementia, myocardial infarction, obesity, peripheral vascular disease, reperfusion injury, restenosis, renal artery atherosclerosis, rheumatic heart disease, stroke, thrombotic disorder, transitory ischemic attacks, and lipoprotein abnormalities associated with Alzheimer's disease, obesity, diabetes mellitus, syndrome X, impotence, multiple sclerosis, Parkinson's disease, and inflammatory diseases.

As used herein, "inflammatory diseases" refers to diseases, disorders, and conditions that are mediated by BET inhibition. Exemplary inflammatory diseases, include, but are not limited to, arthritis, asthma, dermatitis, psoriasis, cystic fibrosis, post transplantation late and chronic solid organ rejection, multiple sclerosis, systemic lupus erythematosus, inflammatory bowel diseases, autoimmune diabetes, diabetic retinopathy, diabetic nephropathy, diabetic vasculopathy, ocular inflammation, uveitis, rhinitis, ischemia-reperfusion injury, post-angioplasty restenosis, chronic obstructive pulmonary disease (COPD), glomerulonephritis, Graves disease, gastrointestinal allergies, conjunctivitis, atherosclerosis, coronary artery disease, angina, and small artery disease.

As used herein, "cancer" refers to diseases, disorders, and conditions that are mediated by BET inhibition. Exemplary cancers, include, but are not limited to, chronic lymphocytic leukemia and multiple myeloma, follicular lymphoma, diffuse large B cell lymphoma with germinal center phenotype, Burkitt's lymphoma, Hodgkin's lymphoma, follicular lymphomas and activated, anaplastic large cell lymphoma, neuroblastoma and primary neuroectodermal tumor, rhabdomyosarcoma, prostate cancer, breast cancer, NMC (NUT-midline carcinoma), acute myeloid leukemia (AML), acute B lymphoblastic leukemia (B-ALL), Burkitt's Lymphoma, B-cell lymphoma, melanoma, mixed lineage leukemia, multiple myeloma, pro-myelocytic leukemia (PML), non-Hodgkin's lymphoma, neuroblastoma, medulloblastoma, lung carcinoma (NSCLC, SCLC), and colon carcinoma.

"Subject" refers to an animal, such as a mammal, that has been or will be the object of treatment, observation, or experiment. The methods described herein may be useful for both human therapy and veterinary applications. In one embodiment, the subject is a human.

As used herein, "treatment" or "treating" refers to an amelioration of a disease or disorder, or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder. For example, treating a cholesterol disorder may comprise decreasing blood cholesterol levels.

As used herein, "prevention" or "preventing" refers to a reduction of the risk of acquiring a given disease or disorder.

A dash ("-") that is not between two letters or symbols is used to indicate a point of attachment for a substituent. For example, —$CONH_2$ is attached through the carbon atom.

By "optional" or "optionally" is meant that the subsequently described event or circumstance may or may not occur, and that the description includes instances where the event or circumstance occurs and instances in which is does not. For example, "optionally substituted aryl" encompasses both "aryl" and "substituted aryl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "hydrate" refers to a crystal form with either a stoichiometric or non-stoichiometric amount of water is incorporated into the crystal structure.

The term "alkenyl" as used herein refers to an unsaturated straight or branched hydrocarbon having at least one carbon-carbon double bond, such as a straight or branched group of 2-8 carbon atoms, referred to herein as ($C_2$-$C_8$)alkenyl. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, and 4-(2-methyl-3-butene)-pentenyl.

The term "alkoxy" as used herein refers to an alkyl group attached to an oxygen (—O-alkyl-). "Alkoxy" groups also include an alkenyl group attached to an oxygen ("alkenyloxy") or an alkynyl group attached to an oxygen ("alkynyloxy") groups. Exemplary alkoxy groups include, but are not limited to, groups with an alkyl, alkenyl or alkynyl group of 1-8 carbon atoms, referred to herein as $(C_1-C_8)$alkoxy. Exemplary alkoxy groups include, but are not limited to methoxy and ethoxy.

The term "alkyl" as used herein refers to a saturated straight or branched hydrocarbon, such as a straight or branched group of 1-8 carbon atoms, referred to herein as $(C_1-C_8)$alkyl. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl.

The term "alkynyl" as used herein refers to an unsaturated straight or branched hydrocarbon having at least one carbon-carbon triple bond, such as a straight or branched group of 2-8 carbon atoms, referred to herein as $(C_2-C_8)$alkynyl. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl.

The term "amide" as used herein refers to the form —$NR_aC(O)(R_b)$— or —$C(O)NR_bR_c$, wherein $R_a$, $R_b$ and $R_c$ are each independently selected from alkyl, alkenyl, alkynyl, aryl, arylalkyl, cycloalkyl, haloalkyl, heteroaryl, heterocyclyl, and hydrogen. The amide can be attached to another group through the carbon, the nitrogen, $R_b$, or $R_c$. The amide also may be cyclic, for example $R_b$ and $R_c$, may be joined to form a 3- to 8-membered ring, such as 5- or 6-membered ring. The term "amide" encompasses groups such as sulfonamide, urea, ureido, carbamate, carbamic acid, and cyclic versions thereof. The term "amide" also encompasses an amide group attached to a carboxy group, e.g., -amide-COOH or salts such as -amide-COONa, an amino group attached to a carboxy group (e.g., -amino-COOH or salts such as -amino-COONa).

The term "amine" or "amino" as used herein refers to the form —$NR_dR_e$ or —$N(R_d)R_e$—, where $R_d$ and $R_e$ are independently selected from alkyl, alkenyl, alkynyl, aryl, arylalkyl, carbamate, cycloalkyl, haloalkyl, heteroaryl, heterocycle, and hydrogen. The amino can be attached to the parent molecular group through the nitrogen. The amino also may be cyclic, for example any two of $R_d$ and $R_e$ may be joined together or with the N to form a 3- to 12-membered ring (e.g., morpholino or piperidinyl). The term amino also includes the corresponding quaternary ammonium salt of any amino group. Exemplary amino groups include alkylamino groups, wherein at least one of $R_d$ or $R_e$ is an alkyl group. In some embodiments $R_d$ and $R_e$ each may be optionally substituted with hydroxyl, halogen, alkoxy, ester, or amino.

The term "aryl" as used herein refers to a mono-, bi-, or other multi-carbocyclic, aromatic ring system. The aryl group can optionally be fused to one or more rings selected from aryls, cycloalkyls, and heterocyclyls. The aryl groups of this present disclosure can be substituted with groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include, but are not limited to a monocyclic aromatic ring system, wherein the ring comprises 6 carbon atoms, referred to herein as "$(C_6)$aryl."

The term "arylalkyl" as used herein refers to an alkyl group having at least one aryl substituent (e.g., -aryl-alkyl-). Exemplary arylalkyl groups include, but are not limited to, arylalkyls having a monocyclic aromatic ring system, wherein the ring comprises 6 carbon atoms, referred to herein as "$(C_6)$arylalkyl."

The term "carbamate" as used herein refers to the form —$R_gOC(O)N(R_h)$—, —$R_gOC(O)N(R_h)R_i$—, or —$OC(O)NR_hR_i$, wherein $R_g$, $R_h$ and $R_i$ are each independently selected from alkyl, alkenyl, alkynyl, aryl, arylalkyl, cycloalkyl, haloalkyl, heteroaryl, heterocyclyl, and hydrogen. Exemplary carbamates include, but are not limited to, arylcarbamates or heteroaryl carbamates (e.g., wherein at least one of $R_g$, $R_h$ and $R_i$ are independently selected from aryl or heteroaryl, such as pyridine, pyridazine, pyrimidine, and pyrazine).

The term "carbocycle" as used herein refers to an aryl or cycloalkyl group.

The term "carboxy" as used herein refers to —COOH or its corresponding carboxylate salts (e.g., —COONa). The term carboxy also includes "carboxycarbonyl," e.g. a carboxy group attached to a carbonyl group, e.g., —C(O)—COOH or salts, such as —C(O)—COONa.

The term "cyano" as used herein refers to —CN.

The term "cycloalkoxy" as used herein refers to a cycloalkyl group attached to an oxygen.

The term "cycloalkyl" as used herein refers to a saturated or unsaturated cyclic, bicyclic, or bridged bicyclic hydrocarbon group of 3-12 carbons, or 3-8 carbons, referred to herein as "$(C_3-C_8)$cycloalkyl," derived from a cycloalkane. Exemplary cycloalkyl groups include, but are not limited to, cyclohexanes, cyclohexenes, cyclopentanes, and cyclopentenes. Cycloalkyl groups may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Cycloalkyl groups can be fused to other cycloalkyl saturated or unsaturated, aryl, or heterocyclyl groups.

The term "dicarboxylic acid" as used herein refers to a group containing at least two carboxylic acid groups such as saturated and unsaturated hydrocarbon dicarboxylic acids and salts thereof. Exemplary dicarboxylic acids include alkyl dicarboxylic acids. Dicarboxylic acids may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone. Dicarboxylic acids include, but are not limited to succinic acid, glutaric acid, adipic acid, suberic acid, sebacic acid, azelaic acid, maleic acid, phthalic acid, aspartic acid, glutamic acid, malonic acid, fumaric acid, (+)/(−)-malic acid, (+)/(−) tartaric acid, isophthalic acid, and terephthalic acid. Dicarboxylic acids further include carboxylic acid derivatives thereof, such as anhydrides, imides, hydrazides (for example, succinic anhydride and succinimide).

The term "ester" refers to the structure —C(O)O—, —C(O)O—$R_j$—, —$R_kC(O)O—R_j$—, or —$R_kC(O)O$—, where O is not bound to hydrogen, and $R_j$ and $R_k$ can independently be selected from alkoxy, aryloxy, alkyl, alkenyl, alkynyl, amide, amino, aryl, arylalkyl, cycloalkyl, ether, haloalkyl, heteroaryl, and heterocyclyl. $R_k$ can be a hydrogen atom, but $R_j$ cannot be a hydrogen atom. The ester may be cyclic, for example the carbon atom and $R_j$, the oxygen atom and $R_k$, or $R_j$ and $R_k$ may be joined to form a 3- to 12-membered ring. Exemplary esters include, but are not limited to, alkyl esters wherein at least one of $R_j$ or $R_k$ is alkyl, such as —O—C(O)-alkyl, —C(O)—O-alkyl-, and -alkyl-C(O)—O-alkyl-. Exemplary esters also include aryl or heteoraryl esters, e.g. wherein at least one of $R_j$ or $R_k$ is a heteroaryl group such as pyridine, pyridazine, pyrimidine and pyrazine, such as a nicotinate ester. Exemplary esters also include reverse esters having the structure —$R_k$C(O)O—, where the oxygen is bound to the parent molecule. Exemplary reverse esters include succinate, D-argininate, L-argininate, L-lysinate and D-lysinate. Esters also include carboxylic acid anhydrides and acid halides.

The terms "halo" or "halogen" as used herein refer to F, Cl, Br, or I.

The term "haloalkyl" as used herein refers to an alkyl group substituted with one or more halogen atoms. "Haloalkyls" also encompass alkenyl or alkynyl groups substituted with one or more halogen atoms.

The term "heteroaryl" as used herein refers to a mono-, bi-, or multi-cyclic, aromatic ring system containing one or more heteroatoms, for example 1-3 heteroatoms, such as nitrogen, oxygen, and sulfur. Heteroaryls can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heteroaryls can also be fused to non-aromatic rings. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidilyl, tetrazolyl, furyl, thienyl, isoxazolyl, thiazolyl, furyl, phenyl, isoxazolyl, and oxazolyl. Exemplary heteroaryl groups include, but are not limited to, a monocyclic aromatic ring, wherein the ring comprises 2-5 carbon atoms and 1-3 heteroatoms, referred to herein as "($C_2$-$C_5$)heteroaryl."

The terms "heterocycle," "heterocyclyl," or "heterocyclic" as used herein refer to a saturated or unsaturated 3-, 4-, 5-, 6- or 7-membered ring containing one, two, or three heteroatoms independently selected from nitrogen, oxygen, and sulfur. Heterocycles can be aromatic (heteroaryls) or non-aromatic. Heterocycles can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heterocycles also include bicyclic, tricyclic, and tetracyclic groups in which any of the above heterocyclic rings is fused to one or two rings independently selected from aryls, cycloalkyls, and heterocycles. Exemplary heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolidin-2-onyl, pyrrolinyl, pyrrolyl, quinolinyl, quinoxaloyl, tetrahydrofuryl, tetrahydroisoquinolyl, tetrahydropyranyl, tetrahydroquinolyl, tetrazolyl, thiadiazolyl, thiazolidinyl, thiazolyl, thienyl, thiomorpholinyl, thiopyranyl, and triazolyl.

The terms "hydroxy" and "hydroxyl" as used herein refer to —OH.

The term "hydroxyalkyl" as used herein refers to a hydroxy attached to an alkyl group.

The term "hydroxyaryl" as used herein refers to a hydroxy attached to an aryl group.

The term "ketone" as used herein refers to the structure —C(O)—$R_n$ (such as acetyl, —C(O)CH$_3$) or —$R_n$—C(O)—$R_o$—. The ketone can be attached to another group through $R_n$ or $R_o$. $R_n$ or $R_o$ can be alkyl, alkenyl, alkynyl, cycloalkyl, heterocyclyl or aryl, or $R_n$ or $R_o$ can be joined to form a 3- to 12-membered ring.

The term "monoester" as used herein refers to an analogue of a dicarboxylic acid wherein one of the carboxylic acids is functionalized as an ester and the other carboxylic acid is a free carboxylic acid or salt of a carboxylic acid. Examples of monoesters include, but are not limited to, to monoesters of succinic acid, glutaric acid, adipic acid, suberic acid, sebacic acid, azelaic acid, oxalic and maleic acid.

The term "phenyl" as used herein refers to a 6-membered carbocyclic aromatic ring. The phenyl group can also be fused to a cyclohexane or cyclopentane ring. Phenyl can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, phosphate, sulfide, sulfinyl, sulfonyl, sulfonic acid, sulfonamide and thioketone.

The term "thioalkyl" as used herein refers to an alkyl group attached to a sulfur (—S-alkyl-).

"Alkyl," "alkenyl," "alkynyl", "alkoxy", "amino" and "amide" groups can be optionally substituted with or interrupted by or branched with at least one group selected from alkoxy, aryloxy, alkyl, alkenyl, alkynyl, amide, amino, aryl, arylalkyl, carbamate, carbonyl, carboxy, cyano, cycloalkyl, ester, ether, formyl, halogen, haloalkyl, heteroaryl, heterocyclyl, hydroxyl, ketone, phosphate, sulfide, sulfinyl, sulfonyl, sulfonic acid, sulfonamide, thioketone, ureido and N. The substituents may be branched to form a substituted or unsubstituted heterocycle or cycloalkyl.

As used herein, a suitable substitution on an optionally substituted substituent refers to a group that does not nullify the synthetic or pharmaceutical utility of the compounds of the present disclosure or the intermediates useful for preparing them. Examples of suitable substitutions include, but are not limited to: $C_{1-8}$ alkyl, alkenyl or alkynyl; $C_{1-6}$ aryl, $C_{2-5}$ heteroaryl; $C_{37}$ cycloalkyl; $C_{1-8}$ alkoxy; $C_6$ aryloxy; —CN; —OH; oxo; halo, carboxy; amino, such as —NH($C_{1-8}$ alkyl), —N($C_{1-8}$ alkyl)$_2$, —NH(($C_6$)aryl), or —N(($C_6$)aryl)$_2$; formyl; ketones, such as —CO($C_{1-8}$ alkyl), —CO(($C_6$ aryl) esters, such as —CO$_2$($C_{1-8}$ alkyl) and —CO$_2$ ($C_6$ aryl). One of skill in art can readily choose a suitable substitution based on the stability and pharmacological and synthetic activity of the compound of the present disclosure.

The term "pharmaceutically acceptable carrier" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutically acceptable composition" as used herein refers to a composition comprising at least one compound as disclosed herein formulated together with one or more pharmaceutically acceptable carriers.

The term "pharmaceutically acceptable prodrugs" as used herein represents those prodrugs of the compounds of the present disclosure that are, within the scope of sound medical judgment, suitable for use in contact with the tissues of humans and lower animals without undue toxicity, irritation, allergic response, commensurate with a reasonable benefit/risk ratio, and effective for their intended use, as well as the zwitterionic forms, where possible, of the compounds of the present disclosure. A discussion is provided in Higuchi et al., "Prodrugs as Novel Delivery Systems," *ACS Symposium Series*, Vol. 14, and in Roche, E. B., ed. *Bioreversible Carriers in Drug Design*, American Pharmaceutical Association and Pergamon Press, 1987, both of which are incorporated herein by reference.

The term "pharmaceutically acceptable salt(s)" refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, matate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions, that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present disclosure encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

Individual stereoisomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well-known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well-known asymmetric synthetic methods.

Geometric isomers can also exist in the compounds of the present disclosure. The present disclosure encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the E and Z isomers.

Substituents around a carbon-carbon double bond alternatively can be referred to as "cis" or "trans," where "cis" represents substituents on the same side of the double bond and "trans" represents substituents on opposite sides of the double bond. The arrangements of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The compounds disclosed herein may exist as tautomers and both tautomeric forms are intended to be encompassed by the scope of the present disclosure, even though only one tautomeric structure is depicted.

EXEMPLARY EMBODIMENTS OF THE INVENTION

Certain embodiments of the invention provide compounds of Formula I, which include compounds of Formula Ia, compositions and formulations containing such compounds, and methods of using and making such compounds.

Some embodiments relate to a compound according to Formula I:

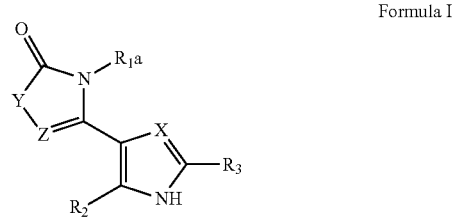

Formula I or a stereoisomer, tautomer, pharmaceutically acceptable salt, or hydrate thereof, wherein:

X is selected from CH and N;

Y is selected from —NH, —N—$R_{1b}$ and oxygen;

Z is selected from N, and —CH—;

$R_{1a}$ and $R_{1b}$ are independently selected from alkyl ($C_1$-$C_6$), carbocycle ($C_3$-$C_{10}$), and heterocycle ($C_2$-$C_{10}$) optionally substituted with 1 to 3 groups selected from $R_4$;

$R_2$ is selected from aryl ($C_5$-$C_{10}$) and heteroaryl ($C_5$-$C_{10}$) optionally substituted with 1 to 5 groups selected from $R_5$;

$R_3$ is selected from carbocycle ($C_3$-$C_{10}$) and heterocycle ($C_2$-$C_{10}$) optionally substituted with 1 to 5 groups selected from $R_5$;

each $R_4$ is independently selected from deuterium, alkyl ($C_1$-$C_6$) (such as methyl, ethyl, propyl, isopropyl, butyl), cycloalkyl ($C_3$-$C_8$) (such as cyclopropyl, cyclobutyl, cyclopentyl, cyclohexyl), alkoxy ($C_1$-$C_6$) (such as methoxy, ethoxy, isopropoxy), amino (such as —$NH_2$, —NHMe, —NHEt, —NHiPr, —NHBu-$NMe_2$, NMeEt, —$NEt_2$, —NEtBu), —NHC(O)NH-alkyl($C_1$-$C_6$), halogen (such as F, Cl), amide (such as —NHC(O)Me, —NHC(O)Et, —C(O)NHMe, —C(O)$NEt_2$, —C(O)NiPr), —$CF_3$, —CN, —$N_3$, ketone (such as acetyl, —C(O)Et, —C(O)Pr), —S(O)-alkyl($C_1$-$C_4$) (such as —S(O)Me, —S(O)Et), —$SO_2$-alkyl($C_1$-$C_6$) (such as —$SO_2$Me, —$SO_2$Et, —$SO_2$Pr), thioalkyl($C_1$-$C_6$) (such as —SMe, —SEt, —SPr, —SBu), —COOH, and ester (such as —C(O)OMe, —C(O)OEt, —C(O)OBu), each of which may be optionally substituted with hydrogen, F, Cl, Br, —OH, —$NH_2$, —NHMe, —OMe, —SMe, oxo, and/or thio-oxo; and each $R_5$ is independently selected from deuterium, alkyl ($C_1$-$C_6$) (such as methyl, ethyl, propyl, isopropyl, butyl), alkoxy($C_1$-$C_6$) (such as methoxy, ethoxy, isopropoxy), amino (such as —$NH_2$, —NHMe, —NHEt, —NHiPr, —NHBu-$NMe_2$, NMeEt, —$NEt_2$, —NEtBu), —NHC(O)NH— alkyl($C_1$-$C_6$), halogen (such as F, Cl), amide (such as —NHC(O)Me, —NHC(O)Et, —C(O)NHMe, —C(O)$NEt_2$, —C(O)NiPr), —$CF_3$, —CN, —$N_3$, ketone (such as acetyl, —C(O)Et, —C(O)Pr), —S(O)-alkyl($C_1$-$C_4$) (such as —S(O)Me, —S(O)Et), —$SO_2$-alkyl($C_1$-$C_6$) (such as —$SO_2$Me, —$SO_2$Et, —$SO_2$Pr), thioalkyl($C_1$-$C_6$) (such as —SMe, —SEt, —SPr, —SBu), —COOH, and ester (such as —C(O)OMe, —C(O)OEt, —C(O)OBu), each of which may be optionally substituted with hydrogen, F, Cl, Br, —OH, —$NH_2$, —NHMe, —OMe, —SMe, oxo, and/or thio-OXO.

Some embodiments provide compound of Formula Ia, which are a subset of compounds of Formula I, compositions and formulations containing such compounds, and methods of using and making such compounds:

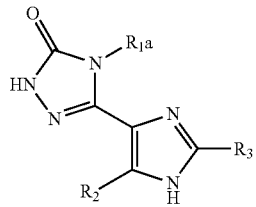

Formula Ia or a stereoisomer, tautomer, pharmaceutically acceptable salt, or hydrate thereof, wherein: $R_{1a}$ is selected from alkyl ($C_1$-$C_6$), carbocycle ($C_3$-$C_{10}$), and heterocycle ($C_2$-$C_{10}$) optionally substituted with 1 to 3 groups selected from $R_4$;

$R_2$ is selected from aryl ($C_5$-$C_{10}$) and heteroaryl ($C_5$-$C_{10}$) optionally substituted with 1 to 5 groups selected from $R_5$;

$R_3$ is selected from carbocycle ($C_3$-$C_{10}$) and heterocycle ($C_2$-$C_{10}$) optionally substituted with 1 to 5 groups selected from $R_5$;

each $R_4$ is independently selected from deuterium, alkyl ($C_1$-$C_6$) (such as methyl, ethyl, propyl, isopropyl, butyl), cycloalkyl ($C_3$-$C_8$) (such as cyclopropyl, cyclobutyl, cyclopentyl, cyclohexyl), alkoxy ($C_1$-$C_6$) (such as methoxy, ethoxy, isopropoxy), amino (such as —$NH_2$, —NHMe, —NHEt, —NHiPr, —NHBu-$NMe_2$, NMeEt, —$NEt_2$, —NEtBu), —NHC(O)NH-alkyl($C_1$-$C_6$), halogen (such as F, Cl), amide (such as —NHC(O)Me, —NHC(O)Et, —C(O)NHMe, —C(O)$NEt_2$, —C(O)NiPr), —$CF_3$, —CN, —$N_3$, ketone (such as acetyl, —C(O)Et, —C(O)Pr), —S(O)-alkyl($C_1$-$C_4$) (such as —S(O)Me, —S(O)Et), —$SO_2$-alkyl($C_1$-$C_6$) (such as —$SO_2$Me, —$SO_2$Et, —$SO_2$Pr), thioalkyl($C_1$-$C_6$) (such as —SMe, —SEt, —SPr, —SBu), —COOH, and ester (such as —C(O)OMe, —C(O)OEt, —C(O)OBu), each of which may be optionally substituted with hydrogen, F, Cl, Br, —OH, —$NH_2$, —NHMe, —OMe, —SMe, oxo, and/or thio-oxo; and each $R_5$ is independently selected from deuterium, alkyl ($C_1$-$C_6$) (such as methyl, ethyl, propyl, isopropyl, butyl), alkoxy ($C_1$-$C_6$) (such as methoxy, ethoxy, isopropoxy), amino (such as —$NH_2$, —NHMe, —NHEt, —NHiPr, —NHBu-$NMe_2$, NMeEt, —$NEt_2$, —NEtBu), —NHC(O)NH— alkyl($C_1$-$C_6$), halogen (such as F, Cl), amide (such as —NHC(O)Me, —NHC(O)Et, —C(O)NHMe, —C(O)$NEt_2$, —C(O)NiPr), —$CF_3$, —CN, —$N_3$, ketone ($C_1$-$C_6$) (such as acetyl, —C(O)Et, —C(O)Pr), —S(O)-alkyl($C_1$-$C_4$) (such as —S(O)Me, —S(O)Et), —$SO_2$-alkyl($C_1$-$C_6$) (such as —$SO_2$Me, —$SO_2$Et, —$SO_2$Pr), thioalkyl($C_1$-$C_6$) (such as —SMe, —SEt, —SPr, —SBu), —COOH, and ester (such as —C(O)OMe, —C(O)OEt, —C(O)OBu), each of which may be optionally substituted with hydrogen, F, Cl, Br, —OH, —$NH_2$, —NHMe, —OMe, —SMe, oxo, and/or thio-OXO.

In some embodiments, each $R_4$ in Formula I or Formula Ia is independently selected from deuterium, alkyl ($C_1$-$C_6$) (such as methyl, ethyl, propyl, isopropyl, butyl), alkoxy ($C_1$-$C_6$) (such as methoxy, ethoxy, isopropoxy), amino (such as —$NH_2$, —NHMe, —NHEt, —NHiPr, —NHBu-$NMe_2$, NMeEt, —$NEt_2$, —NEtBu), —NHC(O)NH-alkyl($C_1$-$C_6$), halogen (such as F, Cl), amide (such as —NHC(O)Me, —NHC(O)Et, —C(O)NHMe, —C(O)$NEt_2$, —C(O)NiPr), —$CF_3$, —CN, —$N_3$, ketone (such as acetyl, —C(O)Et, —C(O)Pr), —S(O)-alkyl($C_1$-$C_4$) (such as —S(O)Me, —S(O)Et), —$SO_2$-alkyl($C_1$-$C_6$) (such as —$SO_2$Me, —$SO_2$Et, —$SO_2$Pr), thioalkyl($C_1$-$C_6$) (such as —SMe, —SEt, —SPr, —SBu), —COOH, and ester (such as —C(O)OMe, —C(O)OEt, —C(O)OBu), each of which may be optionally substituted with hydrogen, F, Cl, Br, —OH, —$NH_2$, —NHMe, —OMe, —SMe, oxo, and/or thio-oxo; and X, Y, Z, $R_{1a}$, $R_{1b}$, $R_2$, $R_3$, and $R_5$ are as defined in paragraphs 83 or 84.

In some embodiments according to Formula I, X is N; and Y, Z, $R_{1a}$, $R_{1b}$, $R_2$, $R_3$, $R_4$, and $R_5$ are as defined in any one or combination of paragraphs 83-124 herein.

In some embodiments according to Formula I, X is CH; and Y, Z, $R_{1a}$, $R_{1b}$, $R_2$, $R_3$, $R_4$, and $R_5$ are as defined in any one or combination of paragraphs 83-124 herein.

In some embodiments according to Formula I, Y is —$NR_{1b}$; and X, Z, $R_{1a}$, $R_{1b}$, $R_2$, $R_3$, $R_4$, and $R_5$ are as defined in any one or combination of paragraphs 83-124 herein.

In some embodiments according to Formula I, Y is —NH; and X, Z, $R_{1a}$, $R_{1b}$, $R_2$, $R_3$, $R_4$, and $R_5$ are as defined in any one or combination of paragraphs 83-124 herein.

In some embodiments according to Formula I, Y is oxygen; and X, Z, $R_{1a}$, $R_{1b}$, $R_2$, $R_3$, $R_4$, and $R_5$ are as defined in any one or combination of paragraphs 83-124 herein.

In some embodiments according to Formula I, Z is N; and X, Y, $R_{1a}$, $R_{1b}$, $R_2$, $R_3$, $R_4$, and $R_5$ are as defined in any one or combination of paragraphs 83-124 herein.

In some embodiments according to Formula I, Z is CH; and X, Y, $R_{1a}$, $R_{1b}$, $R_2$, $R_3$, $R_4$, and $R_5$ are as defined in any one or combination of paragraphs 83-124 herein.

In some embodiments according to Formula I or Formula Ia, $R_{1a}$ is selected from alkyl ($C_1$-$C_6$), carbocycle ($C_3$-$C_6$), heterocycle ($C_2$-$C_5$) optionally substituted with 1 to 3 groups selected from $R_4$; and X, Y, Z, $R_{1b}$, $R_2$, $R_3$, $R_4$, and $R_5$ are as defined in any one or combination of paragraphs 83-124 herein.

In some embodiments according to Formula I or Formula Ia, $R_{1a}$ is selected from alkyl ($C_1$-$C_6$) and carbocycle ($C_3$-$C_6$) optionally substituted with 1 to 3 groups selected from $R_4$; and X, Y, Z, $R_{1b}$, $R_2$, $R_3$, $R_4$, and $R_5$ are as defined in any one or combination of paragraphs 83-124 herein.

In some embodiments according to Formula I or Formula Ia, $R_{1a}$ is selected from, but not limited to, the following structures, which may be optionally substituted with 1 to 3 groups selected from $R_4$:

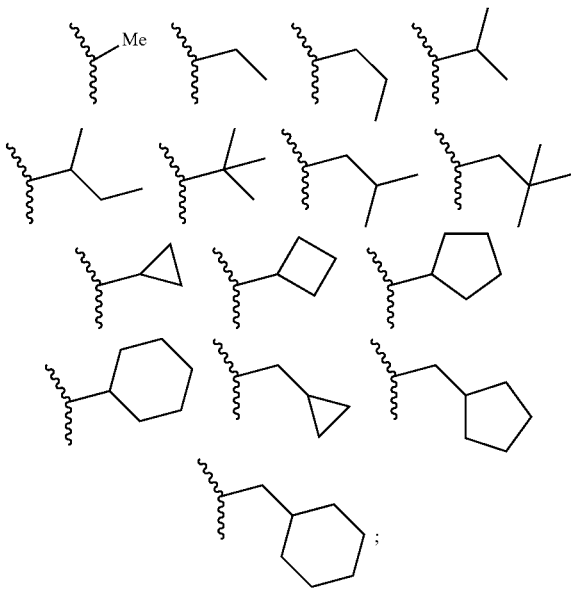

and X, Y, Z, $R_{1b}$, $R_2$, $R_3$, $R_4$, and $R_5$ are as defined in any one or combination of paragraphs 83-124 herein.

In some embodiments according to Formula I of Formula Ia, $R_{1a}$ is selected from, but not limited to, the following structures, which may be optionally substituted with 1 to 3 groups selected from $R_4$:

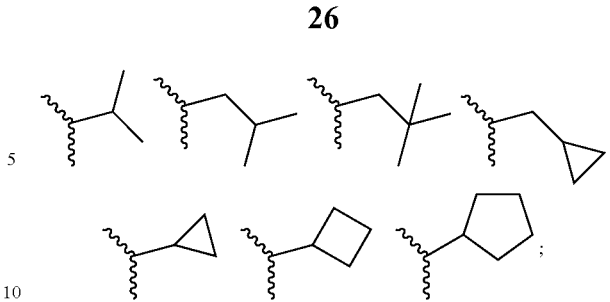

and X, Y, Z, $R_{1b}$, $R_2$, $R_3$, $R_4$, and $R_5$ are as defined in any one or combination of paragraphs 83-124 herein.

In some embodiments according to Formula I or Formula Ia, $R_{1a}$ is

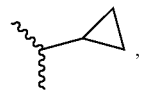

which may be optionally substituted with 1 to 3 groups selected from $R_4$; and X, Y, Z, $R_{1b}$, $R_2$, $R_3$, $R_4$, and $R_5$ are as defined in any one or combination of paragraphs 83-124 herein.

In some embodiments according to Formula I or Formula Ia, $R_{1a}$ is

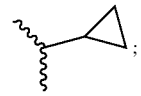 [SMILES: *C1CC1]

and X, Y, Z, $R_{1b}$, $R_2$,

In some embodiments according to Formula I or Formula Ia, $R_{1a}$ is selected from, but not limited to, the following structures, which may be optionally substituted with 1 to 3 groups selected from $R_4$:

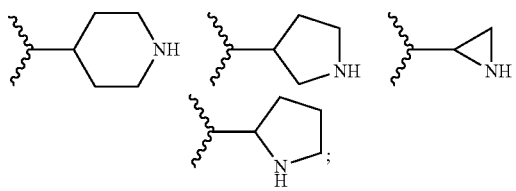

and X, Y, Z, $R_{1b}$, $R_2$, $R_3$, $R_4$, and $R_5$ are as defined in any one or combination of paragraphs 83-156 herein.

In some embodiments according to Formula I, $R_{1b}$ is selected from alkyl ($C_1$-$C_6$); and X, Y, Z, $R_{1a}$, $R_2$, $R_3$, $R_4$, and $R_5$ are as defined in any one or combination of paragraphs 83-124 herein.

In some embodiments according to Formula I, $R_{1b}$ is selected from methyl and ethyl; and X, Y, Z, $R_{1a}$, $R_2$, $R_3$, $R_4$, and $R_5$ are as defined in any one or combination of paragraphs 83-124 herein.

In some embodiments according to Formula I, $R_{1b}$ is methyl; and X, Y, Z, $R_{1a}$, $R_2$, $R_3$, $R_4$, and $R_5$ are as defined in any one or combination of paragraphs 83-124 herein.

In some embodiments according to Formula I or Formula Ia, $R_2$ is selected from optionally substituted bicyclic aryl and bicyclic heteroaryl groups; and X, Y, Z, $R_{1a}$, $R_{1b}$, $R_3$, $R_4$, and $R_5$ are as defined in any one or combination of paragraphs 83-124 herein.

In some embodiments according to Formula I or Formula Ia, $R_2$ is selected from aryl ($C_5$-$C_{10}$) optionally substituted with 1 to 5 groups selected from $R_5$; and X, Y, Z, $R_{1a}$, $R_{1b}$, $R_3$, $R_4$, and $R_5$ are as defined in any one or combination of paragraphs 83-124 herein.

In some embodiments according to Formula I or Formula Ia, $R_2$ is selected from heteroaryl ($C_5$-$C_{10}$) optionally substituted with 1 to 5 groups selected from $R_5$; and X, Y, Z, $R_{1a}$, $R_{1b}$, $R_3$, $R_4$, and $R_5$ are as defined in any one or combination of paragraphs 83-124 herein.

In some embodiments according to Formula I or Formula Ia, $R_2$ is selected from, but not limited to, the following structures, which may be optionally substituted with 1 to 5 groups selected from $R_5$:

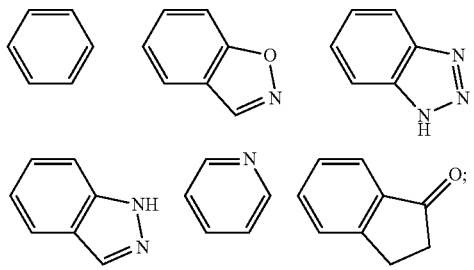

and X, Y, Z, $R_{1a}$, $R_{1b}$, $R_3$, $R_4$, and $R_5$ are as defined in any one or combination of paragraphs 83-124 herein.

In some embodiments according to Formula I or Formula Ia, $R_2$ is selected from, but not limited to, the following structures, which may be optionally substituted with 1 to 5 groups selected from $R_5$:

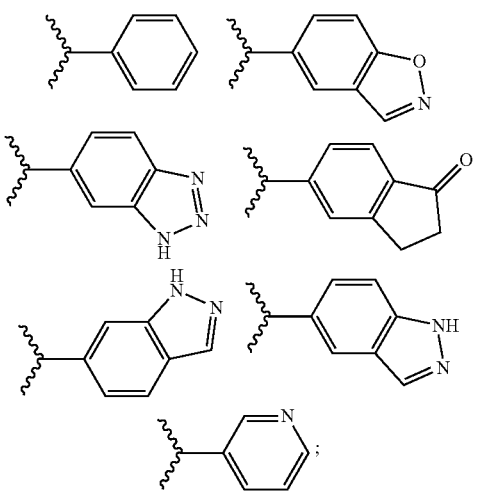

and X, Y, Z, $R_{1a}$, $R_{1b}$, $R_3$, $R_4$, and $R_5$ are as defined in any one or combination of paragraphs 83-124 herein.

In some embodiments according to Formula I or Formula Ia, $R_2$ is selected from, but not limited to, the following structures:

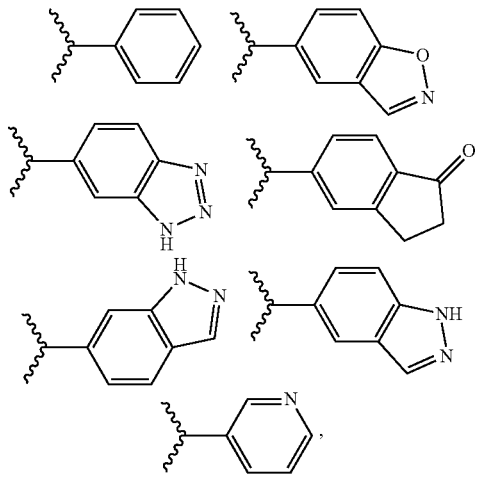

which may be optionally substituted with 1 to 2 groups selected from alkyl ($C_1$-$C_6$), halogen, ketone, amide, and ester; and X, Y, Z, $R_{1a}$, $R_{1b}$, $R_3$, $R_4$, and $R_5$ are as defined in any one or combination of paragraphs 83-124 herein.

In some embodiments according to Formula I or Formula Ia, $R_2$ is selected from, but not limited to, the following structures:

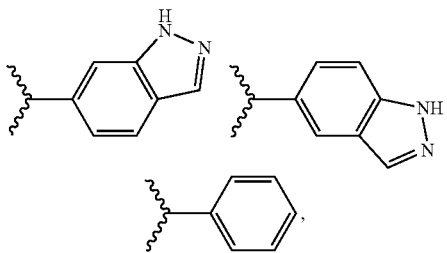

which may be optionally substituted with 1 to 2 groups selected from alkyl ($C_1$-$C_6$), halogen, ketone, amide, and ester; and X, Y, Z, $R_{1a}$, $R_{1b}$, $R_3$, $R_4$, and $R_5$ are as defined in any one or combination of paragraphs 83-124 herein.

In some embodiments according to Formula I or Formula Ia, $R_2$ is selected from, but not limited to, the following structures:

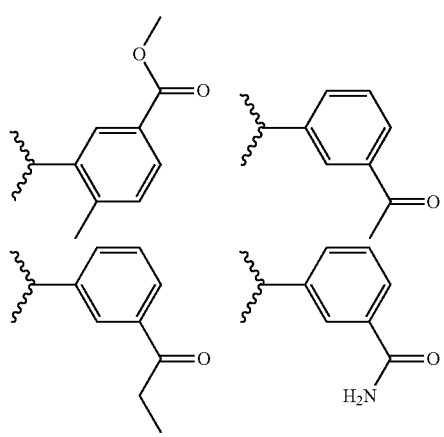

-continued

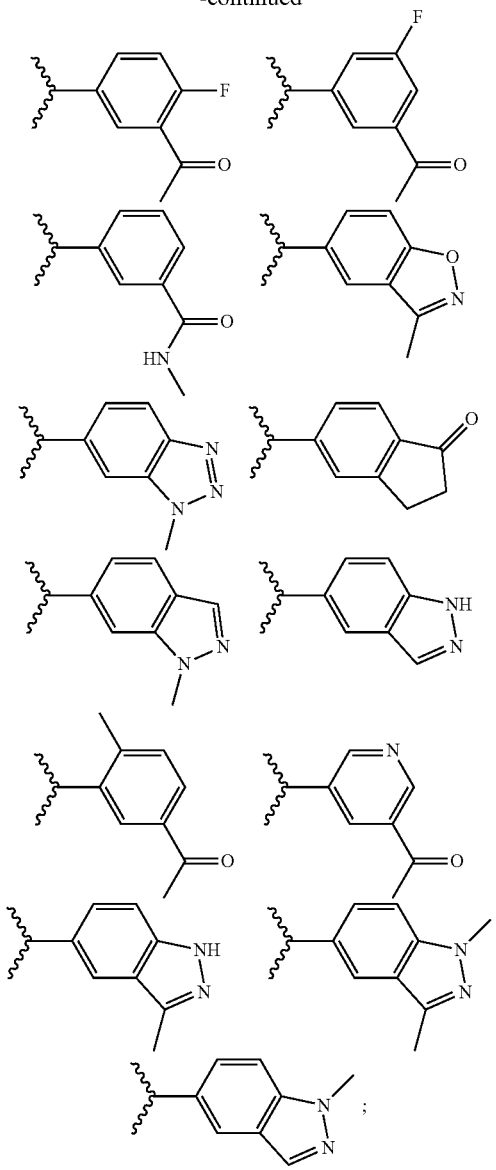

and X, Y, Z, $R_{1a}$, $R_{1b}$, $R_3$, $R_4$, and $R_5$ are as defined in any one or combination of paragraphs 83-124 herein.

In some embodiments according to Formula I or Formula Ia, $R_2$ is

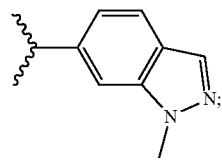

and X, Y, Z, $R_{1a}$, $R_{1b}$, $R_3$, and $R_4$ are as defined in any one or combination of paragraphs 83-124 herein.

In some embodiments according to Formula I or Formula Ia, $R_3$ is selected from carbocycle ($C_3$-$C_{10}$) optionally substituted with 1 to 5 groups selected from $R_5$; and X, Y, Z, $R_{1a}$, $R_{1b}$, $R_2$, $R_4$, and $R_5$ are as defined in any one or combination of paragraphs 83-124 herein.

In some embodiments according to Formula I or Formula Ia, $R_3$ is selected from aryl groups ($C_5$-$C_{10}$) optionally substituted with 1 to 5 groups selected from $R_5$; and X, Y, Z, $R_{1a}$, $R_{1b}$, $R_2$, $R_4$, and $R_5$ are as defined in any one or combination of paragraphs 83-124 herein.

In some embodiments according to Formula I or Formula Ia, $R_3$ is selected from heterocycle ($C_2$-$C_{10}$) optionally substituted with 1 to 5 groups selected from $R_5$; and X, Y, Z, $R_{1a}$, $R_{1b}$, $R_2$, $R_4$, and $R_5$ are as defined in any one or combination of paragraphs 83-124 herein.

In some embodiments according to Formula I or Formula Ia, $R_3$ is selected from, but not limited to, the following structures, which may be optionally substituted with 1 to 5 groups selected from $R_5$:

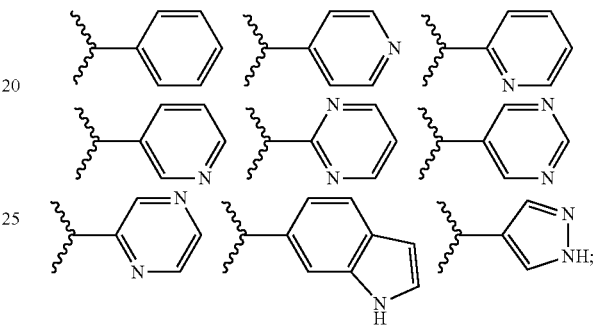

and X, Y, Z, $R_{1a}$, $R_{1b}$, $R_2$, $R_4$, and $R_5$ are as defined in any one or combination of paragraphs 83-124 herein.

In some embodiments according to Formula I or Formula Ia, $R_3$ is selected from, but not limited to, the following structures, which may be optionally substituted with 1 to 5 groups selected from $R_5$:

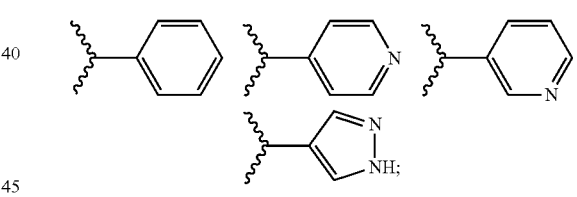

and X, Y, Z, $R_{1a}$, $R_{1b}$, $R_2$, $R_4$, and $R_5$ are as defined in any one or combination of paragraphs 83-124 herein.

In some embodiments according to Formula I or Formula Ia, $R_3$ is selected from, but not limited to, the following structures:

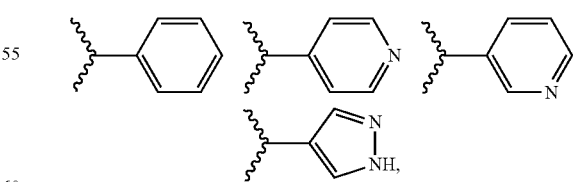

which may be optionally substituted with alkyl ($C_1$-$C_6$); and X, Y, Z, $R_{1a}$, $R_{1b}$, $R_2$, $R_4$, and $R_5$ are as defined in any one or combination of paragraphs 83-124 herein.

In some embodiments according to Formula I or Formula Ia, $R_3$ is selected from, but not limited to, the following structures:

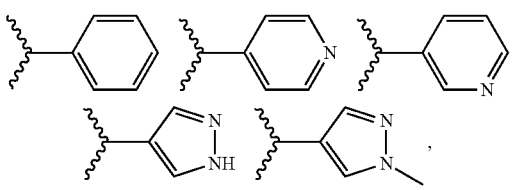

and X, Y, Z, $R_{1a}$, $R_{1b}$, $R_2$, $R_4$, and $R_5$ are as defined in any one or combination of paragraphs 83-156 herein.

In some embodiments according to Formula I or Formula Ia, $R_3$ is selected from phenyl groups which may be optionally substituted with 1 to 5 groups selected from $R_5$; and X, Y, Z, $R_{1a}$, $R_{1b}$, $R_2$, $R_4$, and $R_5$ are as defined in any one or combination of paragraphs 83-124 herein.

In some embodiments according to Formula I or Formula Ia, $R_3$ is an unsubstituted phenyl group; and X, Y, Z, $R_{1a}$, $R_{1b}$, $R_2$, $R_4$, and $R_5$ are as defined in any one or combination of paragraphs 83-124 herein.

In some embodiment according to Formula I or Formula Ia, each $R_4$ is independently selected from deuterium, alkyl ($C_1$-$C_6$) (such as methyl, ethyl, propyl, isopropyl, butyl), alkoxy ($C_1$-$C_6$) (such as methoxy, ethoxy, isopropoxy), amino (such as —$NH_2$, —NHMe, —NHEt, —NHiPr, —NHBu-$NMe_2$, NMeEt, —$NEt_2$, —NEtBu), —NHC(O)NH-alkyl($C_1$-$C_6$), halogen (such as F, Cl), amide (such as —NHC(O)Me, —NHC(O)Et, —C(O)NHMe, —C(O)$NEt_2$, —C(O)NiPr), —$CF_3$, —CN, —$N_3$, ketone (such as acetyl, —C(O)Et, —C(O)Pr), —S(O)-alkyl($C_1$-$C_4$) (such as —S(O)Me, —S(O)Et), —$SO_2$-alkyl($C_1$-$C_6$) (such as —$SO_2$Me, —$SO_2$Et, —$SO_2$Pr), and thioalkyl($C_1$-$C_6$) (such as —SMe, —SEt, —SPr, —SBu); and X, Y, Z, $R_{1a}$, $R_{1b}$, $R_2$, $R_3$, and $R_5$ are as defined in any one or combination of paragraphs 83-124 herein.

In some embodiment according to Formula I or Formula Ia, each $R_4$ is independently selected from deuterium, alkyl ($C_1$-$C_3$) (such as methyl, ethyl, propyl), alkoxy ($C_1$-$C_3$) (such as methoxy, ethoxy), and halogen (such as F, Cl); and X, Y, Z, $R_{1a}$, $R_{1b}$, $R_2$, $R_3$, and $R_5$ are as defined in any one or combination of paragraphs 83-124 herein.

In some embodiments according to Formula I or Formula Ia, each $R_4$ is independently selected from cycloalkyl ($C_3$-$C_8$) (such as cyclopropyl, cyclobutyl, cyclopentyl, cyclohexyl); and X, Y, Z, $R_{1a}$, $R_{1b}$, $R_2$, $R_3$, and $R_4$ are as defined in any one or combination of paragraphs 83-124 herein.

In some embodiment according to Formula I or Formula Ia, each $R_5$ is independently selected from deuterium, alkyl ($C_1$-$C_6$) (such as methyl, ethyl, propyl, isopropyl, butyl), alkoxy ($C_1$-$C_6$) (such as methoxy, ethoxy, isopropoxy), amino (such as —$NH_2$, —NHMe, —NHEt, —NHiPr, —NHBu-$NMe_2$, NMeEt, —$NEt_2$, —NEtBu), —NHC(O)NH-alkyl($C_1$-$C_6$), halogen (such as F, Cl), amide (such as —NHC(O)Me, —NHC(O)Et, —C(O)NHMe, —C(O)$NEt_2$, —C(O)NiPr), —$CF_3$, —CN, —$N_3$, ketone (such as acetyl, —C(O)Et, —C(O)Pr), —S(O)-alkyl($C_1$-$C_4$) (such as —S(O)Me, —S(O)Et), —$SO_2$-alkyl($C_1$-$C_6$) (such as —$SO_2$Me, —$SO_2$Et, —$SO_2$Pr), thioalkyl($C_1$-$C_6$) (such as —SMe, —SEt, —SPr, —SBu), —COOH, and ester (such as —C(O)OMe, —C(O)OEt, —C(O)OBu); and X, Y, Z, $R_{1a}$, $R_{1b}$, $R_2$, $R_3$, and $R_4$ are as defined in any one or combination of paragraphs 83-123 herein.

In certain embodiments, the compound of Formula I or Formula Ia is selected from:
3-(5-(3-Acetylphenyl)-2-phenyl-1H-imidazol-4-yl)-4-cyclopropyl-1H-1,2,4-triazol-5(4H)-one;

Methyl 3-(4-(4-cyclopropyl-5-oxo-4,5-dihydro-1H-1,2,4-triazol-3-yl)-2-phenyl-1H-imidazol-5-yl)-4-methylbenzoate;
3-(4-(4-Cyclopropyl-5-oxo-4,5-dihydro-1H-1,2,4-triazol-3-yl)-2-phenyl-1H-imidazol-5-yl)-N-methylbenzamide;
3-(4-(4-Cyclopropyl-5-oxo-4,5-dihydro-1H-1,2,4-triazol-3-yl)-2-phenyl-1H-imidazol-5-yl)benzamide;
4-Cyclopropyl-3-(5-(3-oxo-2,3-dihydro-1H-inden-5-yl)-2-phenyl-1H-imidazol-4-yl)-1H-1,2,4-triazol-5(4H)-one;
4-Cyclopropyl-3-(2-phenyl-5-(3-propionylphenyl)-1H-imidazol-4-yl)-1H-1,2,4-triazol-5(4H)-one;
4-Cyclopropyl-3-(5-(1-methyl-1H-indazol-6-yl)-2-phenyl-1H-imidazol-4-yl)-1H-1,2,4-triazol-5(4H)-one;
3-(5-(3-Acetyl-4-fluorophenyl)-2-phenyl-1H-imidazol-4-yl)-4-cyclopropyl-1H-1,2,4-triazol-5(4H)-one;
3-(5-(3-Acetyl-5-fluorophenyl)-2-phenyl-1H-imidazol-4-yl)-4-cyclopropyl-1H-1,2,4-triazol-5(4H)-one;
4-cyclopropyl-3-(5-(1-methyl-1H-indazol-5-yl)-2-phenyl-1H-imidazol-4-yl)-1H-1,2,4-triazol-5(4H)-one;
3-(5-(5-acetyl-2-methyl phenyl)-2-phenyl-1H-imidazol-4-yl)-4-cyclopropyl-1H-1,2,4-triazol-5(4H)-one;
3-(5-(5-acetylpyridin-3-yl)-2-phenyl-1H-imidazol-4-yl)-4-cyclopropyl-1H-1,2,4-triazol-5(4H)-one formate;
4-cyclopropyl-3-(5-(1,3-dimethyl-1H-indazol-5-yl)-2-phenyl-1H-imidazol-4-yl)-1H-1,2,4-triazol-5(4H)-one;
4-(Cyclopropylmethyl)-3-(5-(1-methyl-1H-indazol-6-yl)-2-phenyl-1H-imidazol-4-yl)-1H-1,2,4-triazol-5(4H)-one;
4-Isopropyl-3-(5-(1-methyl-1H-indazol-6-yl)-2-phenyl-1H-imidazol-4-yl)-1H-1,2,4-triazol-5(4H)-one;
4-(tert-Butyl)-3-(5-(1-methyl-1H-indazol-6-yl)-2-phenyl-1H-imidazol-4-yl)-1H-1,2,4-triazol-5(4H)-one;
4-Cyclopentyl-3-(5-(1-methyl-1H-indazol-6-yl)-2-phenyl-1H-imidazol-4-yl)-1H-1,2,4-triazol-5(4H)-one;
4-Cyclobutyl-3-(5-(1-methyl-1H-indazol-6-yl)-2-phenyl-1H-imidazol-4-yl)-1H-1,2,4-triazol-5(4H)-one;
4-Cyclohexyl-3-(5-(1-methyl-1H-indazol-6-yl)-2-phenyl-1H-imidazol-4-yl)-1H-1,2,4-triazol-5(4H)-one;
4-Isobutyl-3-(5-(1-methyl-1H-indazol-6-yl)-2-phenyl-1H-imidazol-4-yl)-1H-1,2,4-triazol-5(4H)-one;
3-(5-(1-Methyl-1H-indazol-6-yl)-2-phenyl-1H-imidazol-4-yl)-4-neopentyl-1H-1,2,4-triazol-5(4H)-one;
4-Cyclopropyl-1-ethyl-3-(5-(1-methyl-1H-indazol-6-yl)-2-phenyl-1H-imidazol-4-yl)-1H-1,2,4-triazol-5(4H)-one;
4-Cyclopropyl-1-(cyclopropylmethyl)-3-(5-(1-methyl-1H-indazol-6-yl)-2-phenyl-1H-imidazol-4-yl)-1H-1,2,4-triazol-5(4H)-one;
4-Cyclopropyl-1-(2-methoxyethyl)-3-(5-(1-methyl-1H-indazol-6-yl)-2-phenyl-1H-imidazol-4-yl)-1H-1,2,4-triazol-5(4H)-one;
4-Cyclopropyl-3-(5-(3-methylbenzo[d]isoxazol-5-yl)-2-phenyl-1H-imidazol-4-yl)-1H-1,2,4-triazol-5(4H)-one;
4-Cyclopropyl-3-(5-(1-methyl-1H-benzo[d][1,2,3]triazol-6-yl)-2-phenyl-1H-imidazol-4-yl)-1H-1,2,4-triazol-5(4H)-one;
4-Cyclopropyl-3-(5-(3-methyl-1H-indazol-5-yl)-2-phenyl-1H-imidazol-4-yl)-1H-1,2,4-triazol-5(4H)-one;
4-Cyclopropyl-3-(5-(1-methyl-1H-indazol-6-yl)-2-(pyridin-4-yl)-1H-imidazol-4-yl)-1H-1,2,4-triazol-5(4H)-one;
4-Cyclopropyl-3-(5-(1-methyl-1H-indazol-6-yl)-2-(pyridin-3-yl)-1H-imidazol-4-yl)-1H-1,2,4-triazol-5(4H)-one;
3-(2-(1H-Indol-6-yl)-5-(1-methyl-1H-indazol-6-yl)-1H-imidazol-4-yl)-4-cyclopropyl-1H-1,2,4-triazol-5(4H)-one;
4-Cyclopropyl-3-(5-(1-methyl-1H-indazol-6-yl)-2-(1H-pyrazol-4-yl)-1H-imidazol-4-yl)-1H-1,2,4-triazol-5(4H)-one;

4-Cyclopropyl-3-(5-(1-methyl-1H-indazol-6-yl)-2-(1-methyl-1H-pyrazol-4-yl)-1H-imidazol-4-yl)-1H-1,2,4-triazol-5(4H)-one;

and stereoisomers, tautomers, pharmaceutically acceptable salts, or hydrates thereof.

In certain embodiments, the compound of Formula I is 4-cyclopropyl-1-methyl-3-(5-(1-methyl-1H-indazol-6-yl)-2-phenyl-1H-imidazol-4-yl)-1H-1,2,4-triazol-5(4H)-one or a stereoisomer, tautomer, pharmaceutically acceptable salt, or hydrate thereof.

In certain embodiments, the pharmaceutically acceptable salt of a compound of Formula I is selected from a hydrochloride or dihydrochloride salt.

In certain embodiments, the pharmaceutically acceptable salt of a compound of Formula I or Formula Ia is selected from:

3-(5-(3-acetylphenyl)-2-phenyl-1H-imidazol-4-yl)-4-cyclopropyl-1H-1,2,4-triazol-5(4H)-one hydrochloride;

methyl 3-(4-(4-cyclopropyl-5-oxo-4,5-dihydro-1H-1,2,4-triazol-3-yl)-2-phenyl-1H-imidazol-5-yl)-4-methyl benzoate hydrochloride;

3-(4-(4-cyclopropyl-5-oxo-4,5-dihydro-1H-1,2,4-triazol-3-yl)-2-phenyl-1H-imidazol-5-yl)-N-methyl benzamide hydrochloride;

3-(4-(4-cyclopropyl-5-oxo-4,5-dihydro-1H-1,2,4-triazol-3-yl)-2-phenyl-1H-imidazol-5-yl)benzamide hydrochloride;

4-cyclopropyl-3-(5-(3-oxo-2,3-dihydro-1H-inden-5-yl)-2-phenyl-1H-imidazol-4-yl)-1H-1,2,4-triazol-5(4H)-one hydrochloride;

4-cyclopropyl-3-(2-phenyl-5-(3-propionylphenyl)-1H-imidazol-4-yl)-1H-1,2,4-triazol-5(4H)-one hydrochloride;

4-cyclopropyl-3-(5-(1-methyl-1H-indazol-6-yl)-2-phenyl-1H-imidazol-4-yl)-1H-1,2,4-triazol-5(4H)-one hydrochloride;

3-(5-(3-acetyl-4-fluorophenyl)-2-phenyl-1H-imidazol-4-yl)-4-cyclopropyl-1H-1,2,4-triazol-5(4H)-one hydrochloride;

3-(5-(3-acetyl-5-fluorophenyl)-2-phenyl-1H-imidazol-4-yl)-4-cyclopropyl-1H-1,2,4-triazol-5(4H)-one hydrochloride;

4-cyclopropyl-3-(5-(1-methyl-1H-indazol-5-yl)-2-phenyl-1H-imidazol-4-yl)-1H-1,2,4-triazol-5(4H)-one hydrochloride;

3-(5-(5-acetyl-2-methylphenyl)-2-phenyl-1H-imidazol-4-yl)-4-cyclopropyl-1H-1,2,4-triazol-5(4H)-one hydrochloride;

4-cyclopropyl-3-(5-(3-methyl-1H-indazol-5-yl)-2-phenyl-1H-imidazol-4-yl)-1H-1,2,4-triazol-5(4H)-one hydrochloride;

4-cyclopropyl-3-(5-(1-methyl-1H-benzo[d][1,2,3]triazol-6-yl)-2-phenyl-1H-imidazol-4-yl)-1H-1,2,4-triazol-5(4H)-one hydrochloride;

4-cyclopropyl-3-(5-(1,3-dimethyl-1H-indazol-5-yl)-2-phenyl-1H-imidazol-4-yl)-1H-1,2,4-triazol-5(4H)-one hydrochloride;

4-cyclopropyl-3-(5-(1-methyl-1H-indazol-6-yl)-2-(pyridin-4-yl)-1H-imidazol-4-yl)-1H-1,2,4-triazol-5(4H)-one dihydrochloride;

4-cyclopropyl-3-(5-(1-methyl-1H-indazol-6-yl)-2-(pyridin-3-yl)-1H-imidazol-4-yl)-1H-1,2,4-triazol-5(4H)-one dihydrochloride;

4-cyclopropyl-3-(5-(1-methyl-1H-indazol-6-yl)-2-(1-methyl-1H-pyrazol-4-yl)-1H-imidazol-4-yl)-1H-1,2,4-triazol-5(4H)-one hydrochloride; and 4-cyclopropyl-3-(5-(1-methyl-1H-indazol-6-yl)-2-(1H-pyrazol-4-yl)-1H-imidazol-4-yl)-1H-1,2,4-triazol-5(4H)-one hydrochloride; and stereoisomers, tautomers, or hydrates thereof.

In certain embodiments, the pharmaceutically acceptable salt of a compound of Formula I is 4-cyclopropyl-1-methyl-3-(5-(1-methyl-1H-indazol-6-yl)-2-phenyl-1H-imidazol-4-yl)-1H-1,2,4-triazol-5(4H)-one hydrochloride.

Another aspect of the invention provides a method for inhibition of BET protein function by binding to bromodomains, and their use in the treatment and prevention of diseases and conditions in a mammal (e.g., a human) comprising administering a therapeutically effective amount of a compound of Formula I or Formula Ia or a stereoisomer, tautomer, pharmaceutically acceptable salt, or hydrate thereof.

In one embodiment, because of potent effects of BET inhibitors in vitro on IL-6 and IL-17 transcription, BET inhibitor compounds of Formula I or Formula Ia or a stereoisomer, tautomer, pharmaceutically acceptable salt, or hydrate thereof may be used as therapeutics for inflammatory disorders in which IL-6 and/or IL-17 have been implicated in disease. The following autoimmune diseases are amenable to therapeutic use of BET inhibition by administration of a compound of Formula I or Formula Ia or a stereoisomer, tautomer, pharmaceutically acceptable salt, or hydrate thereof because of a prominent role of IL-6 and/or IL-17: Acute Disseminated Encephalomyelitis (T. Ishizu et al., "CSF cytokine and chemokine profiles in acute disseminated encephalomyelitis," *J Neuroimmunol* 175(1-2): 52-8 (2006)), Agammaglobulinemia (M. Gonzalez-Serrano, et al.," Increased Pro-inflammatory Cytokine Production After Lipopolysaccharide Stimulation in Patients with X-linked Agammaglobulinemia," *J Clin Immunol* 32(5):967-74 (2012)), Allergic Disease (L. McKinley et al., "TH17 cells mediate steroid-resistant airway inflammation and airway hyperresponsiveness in mice," *J Immunol* 181(6):4089-97 (2008)), Ankylosing spondylitis (A. Taylan et al., "Evaluation of the T helper 17 axis in ankylosing spondylitis," *Rheumatol Int* 32(8):2511-5 (2012)), Anti-GBM/Anti-TBM nephritis (Y. Ito et al., "Pathogenic significance of interleukin-6 in a patient with antiglomerular basement membrane antibody-induced glomerulonephritis with multinucleated giant cells," *Am J Kidney Dis* 26(1):72-9 (1995)), Anti-phospholipid syndrome (P. Soltesz et al., "Immunological features of primary anti-phospholipid syndrome in connection with endothelial dysfunction," *Rheumatology* (Oxford) 47(11):1628-34 (2008)), Autoimmune aplastic anemia (Y. Gu et al., "Interleukin (IL)-17 promotes macrophages to produce IL-8, IL-6 and tumour necrosis factor-alpha in aplastic anaemia," *BrJ Haematol* 142(1):109-14 (2008)), Autoimmune hepatitis (L. Zhao et al., "Interleukin-17 contributes to the pathogenesis of autoimmune hepatitis through inducing hepatic interleukin-6 expression," *PLoS One* 6(4): e18909 (2011)), Autoimmune inner ear disease (B. Gloddek et al., "Pharmacological influence on inner ear endothelial cells in relation to the pathogenesis of sensorineural hearing loss," *Adv Otorhinolaryngol* 59:75-83 (2002)), Autoimmune myocarditis (T. Yamashita et al., "IL-6-mediated Th17 differentiation through RORgammat is essential for the initiation of experimental autoimmune myocarditis," *Cardiovasc Res* 91(4):640-8 (2011)), Autoimmune pancreatitis (J. Ni et al.," Involvement of Interleukin-17A in Pancreatic Damage in Rat Experimental Acute Necrotizing Pancreatitis," Inflammation (2012)), Autoimmune retinopathy (S. Hohki et al., "Blockade of interleukin-6 signaling suppresses experimental autoimmune uveoretinitis by the inhibition of inflammatory Th17 responses," *Exp Eye Res* 91(2):162-70 (2010)), Autoimmune thrombocytopenic purpura (D. Ma et al., "Profile of Th17 cytokines (IL-17, TGF-beta, IL-6) and Th1 cytokine (IFN-gamma) in patients with immune thrombocytopenic purpura," *Ann Hematol* 87(11):899-904 (2008)), Behcet's Disease (T. Yoshimura et al., "Involvement of Th17 cells and the effect of anti-IL-6 therapy in autoimmune uveitis," *Rheumatology* (Oxford) 48(4):347-54 (2009)), Bullous pemphigoid (L. D'Auria et al., "Cytokines and bullous pemphigoid," *Eur Cytokine Netw* 10(2):123-34 (1999)), Castleman's Disease (H. El-Osta and R. Kurzrock, "Castleman's disease: from basic mechanisms to molecular therapeutics," *Oncologist* 16(4):497-511 (2011)), Celiac Disease (A. Lahdenpera et al., "Up-regulation of small intestinal interleukin-17 immunity in untreated coeliac disease but not in potential coeliac disease or in type 1 diabetes," *Clin Exp Immunol* 167(2):226-34 (2012)), Churg-Strauss syndrome (A. Fujioka et al., "The analysis of mRNA expression of cytokines from skin lesions in Churg-Strauss syndrome," *J Dermatol* 25(3):171-7 (1998)), Crohn's Disease (V. Holtta et al., "IL-23/IL-17 immunity as a hallmark of Crohn's disease," *Inflamm Bowel Dis* 14(9):1175-84 (2008)), Cogan's syndrome (M. Shibuya et al., "Successful treatment with tocilizumab in a case of Cogan's syndrome complicated with aortitis," *Mod Rheumatol* (2012)), Dry eye syndrome (C. De Paiva et al., "IL-17 disrupts corneal barrier following desiccating stress," *Mucosal Immunol* 2(3):243-53 (2009)), Essential mixed cryoglobulinemia (A. Antonelli et al., "Serum levels of proinflammatory cytokines interleukin-1beta, interleukin-6, and tumor necrosis factor alpha in mixed cryoglobulinemia," *Arthritis Rheum* 60(12):3841-7 (2009)), Dermatomyositis (G. Chevrel et al., "Interleukin-17 increases the effects of IL-1 beta on muscle cells: arguments for the role of T cells in the pathogenesis of myositis," *J Neuroimmunol* 137(1-2):125-33 (2003)), Devic's Disease (U. Linhares et al., "The Ex Vivo Production of IL-6 and IL-21 by CD4(+) T Cells is Directly Associated with Neurological Disability in Neuromyelitis Optica Patients," *J Clin Immunol* (2012)), Encephalitis (D. Kyburz and M. Corr, "Th17 cells generated in the absence of TGF-beta induce experimental allergic encephalitis upon adoptive transfer," *Expert Rev Clin Immunol* 7(3):283-5 (2011)), Eosinophlic esophagitis (P. Dias and G. Banerjee, "The Role of Th17/IL-17 on Eosinophilic Inflammation," *J Autoimmun* (2012)), Eosinophilic fasciitis (P. Dias and G. Banerjee, JAutoimmun (2012)), Erythema nodosum (I. Kahawita and D. Lockwood, "Towards understanding the pathology of erythema nodosum leprosum," *Trans R Soc Trop Med Hyg* 102(4):329-37 (2008)), Giant cell arteritis (J. Deng et al., "Th17 and Th1 T-cell responses in giant cell arteritis," *Circulation* 121(7):906-15 (2010)), Glomerulonephritis (J. Ooi et al., "Review: T helper 17 cells: their role in glomerulonephritis," *Nephrology* (Carlton) 15(5):513-21 (2010)), Goodpasture's syndrome (Y. Ito et al., "Pathogenic significance of interleukin-6 in a patient with antiglomerular basement membrane antibody-induced glomerulonephritis with multinucleated giant cells," *Am J Kidney Dis* 26(1):72-9 (1995)), Granulomatosis with Polyangiitis (Wegener's) (H. Nakahama et al., "Distinct responses of interleukin-6 and other laboratory parameters to treatment in a patient with Wegener's granulomatosis," *Intern Med* 32(2):189-92 (1993)), Graves' Disease (S. Kim et al., "Increased serum interleukin-17 in Graves' ophthalmopathy," *Graefes Arch Clin Exp Ophthalmol* 250(10):1521-6 (2012)), Guillain-Barre syndrome (M. Lu and J. Zhu, "The role of cytokines in Guillain-Barre syndrome," *J Neurol* 258(4):533-48 (2011)), Hashimoto's thyroiditis (N. Figueroa-Vega et al., "Increased circulating pro-inflammatory cytokines and Th17 lymphocytes in Hashimoto's thyroiditis," *J Clin Endocrinol Metab* 95(2):953-62 (2009)), Hemolytic anemia (L. Xu et al., "Critical role of Th17 cells in development of autoimmune hemolytic anemia," *Exp Hematol* (2012)), Henoch-Schonlein purpura (H. Jen et al., "Increased serum interleukin-17 and peripheral Th17 cells in children with acute Henoch-Schonlein purpura," *Pediatr Allergy Immunol* 22(8):862-8 (2011)), IgA nephropathy (F. Lin et al., "Imbalance of regulatory T cells to Th17 cells in IgA nephropathy," *Scand J Clin Lab Invest* 72(3):221-9 (2012)), Inclusion body myositis (P. Baron et al., "Production of IL-6 by human myoblasts stimulated with Abeta: relevance in the pathogenesis of IBM," *Neurology* 57(9):1561-5 (2001)), Type I diabetes (A. Belkina and G. Denis, *Nat Rev Cancer* 12(7):465-77 (2012)), Interstitial cystitis (L. Lamale et al., "Interleukin-6, histamine, and methylhistamine as diagnostic markers for interstitial cystitis," *Urology* 68(4):702-6 (2006)), Kawasaki's Disease (S. Jia et al., "The T helper type 17/regulatory T cell imbalance in patients with acute Kawasaki disease," *Clin Exp Immunol* 162(1):131-7 (2010)), Leukocytoclastic vasculitis (Min, C. K., et al., "Cutaneous leucoclastic vasculitis (LV) following bortezomib therapy in a myeloma patient; association with pro-inflammatory cytokines," *Eur J Haematol* 76(3):265-8 (2006)), Lichen planus (N. Rhodus et al., "Proinflammatory cytokine levels in saliva before and after treatment of (erosive) oral lichen planus with dexamethasone," *Oral Dis* 12(2):112-6 (2006)), Lupus (SLE) (M. Mok et al., "The relation of interleukin 17 (IL-17) and IL-23 to Th1/Th2 cytokines and disease activity in systemic lupus erythematosus," *J Rheumatol* 37(10):2046-52 (2010)), Microscopic polyangitis (A. Muller Kobold et al., "In vitro up-regulation of E-selectin and induction of interleukin-6 in endothelial cells by autoantibodies in Wegener's granulomatosis and microscopic polyangiitis," *Clin Exp Rheumatol* 17(4):433-40 (1999)), Multiple sclerosis (F. Jadidi-Niaragh and A. Mirshafiey, "Th17 cell, the new player of neuroinflammatory process in multiple sclerosis," Scand J *Immunol* 74(1):1-13 (2011)), Myasthenia gravis (R. Aricha et al., "Blocking of IL-6 suppresses experimental autoimmune myasthenia gravis," *J Autoimmun* 36(2):135-41 (2011)), myositis (G. Chevrel et al., "Interleukin-17 increases the effects of IL-1 beta on muscle cells: arguments for the role of T cells in the pathogenesis of myositis," *J Neuroimmunol* 137(1-2):125-33 (2003)), Optic neuritis (S. Icoz et al., "Enhanced IL-6 production in aquaporin-4 antibody positive neuromyelitis optica patients," *Int J Neurosci* 120(1):71-5 (2010)), Pemphigus (E. Lopez-Robles et al., "TNFalpha and IL-6 are mediators in the blistering process of pemphigus," *Int J Dermatol* 40(3):185-8 (2001)), POEMS syndrome (K. Kallen et al., "New developments in IL-6 dependent biology and therapy: where do we stand and what are the options?" *Expert Opin Investig Drugs* 8(9):1327-49 (1999)), Polyarteritis nodosa (T. Kawakami et al., "Serum levels of interleukin-6 in patients with cutaneous polyarteritis nodosa," *Acta Derm Venereol* 92(3):322-3 (2012)), Primary biliary cirrhosis (K. Harada et al., "Periductal interleukin-17 production in association with biliary innate immunity contributes to the pathogenesis of cholangiopathy in primary biliary cirrhosis," *Clin Exp Immunol* 157(2):261-70 (2009)), Psoriasis (S. Fujishima et al., "Involvement of IL-17F via the induction of IL-6 in psoriasis," *Arch Dermatol Res* 302(7):499-505 (2010)), Psoriatic arthritis (S. Raychaudhuri et al., IL-17 receptor and its functional significance in psoriatic arthritis," *Mol Cell Biochem* 359(1-2):419-29 (2012)), Pyoderma gangrenosum (T. Kawakami et al., "Reduction of interleukin-6, interleukin-8, and anti-phosphatidylserine-prothrombin complex antibody by granulocyte and monocyte adsorption apheresis in a patient with pyoderma gangrenosum and ulcerative colitis," *Am J Gastroenterol* 104(9):2363-4 (2009)), Relapsing polychondritis (M. Kawai et al., "Sustained response to tocilizumab, anti-interleukin-6 receptor antibody, in two patients with refractory relapsing polychondritis," *Rheumatology* (Oxford) 48(3):318-9 (2009)), Rheumatoid arthritis (Z. Ash and P. Emery, "The role of tocilizumab in the management of rheumatoid arthritis," *Expert Opin Biol Ther,* 12(9):1277-89 (2012)), Sarcoidosis (F. Belli et al., "Cytokines assay in peripheral blood and bronchoalveolar lavage in the diagnosis and staging of pulmonary granulomatous diseases," *Int J Immunopathol Pharmacol* 13(2):61-67 (2000)), Scleroderma (T. Radstake et al., "The pronounced Th17 profile in systemic sclerosis (SSc) together with intracellular expression of TGFbeta and IFNgamma distinguishes SSc phenotypes," *PLoS One,* 4(6): e5903 (2009)), Sjogren's syndrome (G. Katsifis et al., "Systemic and local interleukin-17 and linked cytokines associated with Sjogren's syndrome immunopathogenesis," *Am J Pathol* 175(3):1167-77 (2009)), Takayasu's arteritis (Y. Sun et al., "MMP-9 and IL-6 are potential biomarkers for disease activity in Takayasu's arteritis," *Int J Cardiol* 156(2):236-8 (2012)), Transverse myelitis (J. Graber et al., "Interleukin-17 in transverse myelitis and multiple sclerosis," *J Neuroimmunol* 196(1-2): 124-32 (2008)), Ulcerative colitis (J. Mudter and M. Neurath, "11-6 signaling in inflammatory bowel disease: pathophysiological role and clinical relevance," *Inflamm Bowel Dis* 13(8):1016-23 (2007)), Uveitis (H. Haruta et al., "Blockade of interleukin-6 signaling suppresses not only th17 but also interphotoreceptor retinoid binding protein-specific Th1 by promoting regulatory T cells in experimental autoimmune uveoretinitis," *Invest Ophthalmol Vis Sci* 52(6): 3264-71 (2011)), and Vitiligo (D. Bassiouny and O. Shaker, "Role of interleukin-17 in the pathogenesis of vitiligo," *Clin Exp Dermatol* 36(3):292-7 115. (2011)). Thus, the invention includes compounds of Formula I or Formula Ia, stereoisomers, tautomers, pharmaceutically acceptable salts, or hydrates thereof; pharmaceutical compositions comprising one or more of those compounds; and methods of using those compounds or compositions for treating these diseases.

Acute and chronic (non-autoimmune) inflammatory diseases characterized by increased expression of pro-inflammatory cytokines, including IL-6, MCP-1, and IL-17, would also be amenable to therapeutic BET inhibition. These include, but are not limited to, sinusitis (D. Bradley and S. Kountakis, "Role of interleukins and transforming growth factor-beta in chronic rhinosinusitis and nasal polyposis," *Laryngoscope* 115(4):684-6 (2005)), pneumonitis (Besnard, A. G., et al., "Inflammasome-IL-1-Th17 response in allergic lung inflammation" *J Mol Cell Biol* 4(1):3-10 (2012)), osteomyelitis (T. Yoshii et al., "Local levels of interleukin-1beta, -4, -6 and tumor necrosis factor alpha in an experimental model of murine osteomyelitis due to *staphylococcus aureus*," *Cytokine* 19(2):59-65 2002), gastritis (T. Bayraktaroglu et al., "Serum levels of tumor necrosis factor-alpha, interleukin-6 and interleukin-8 are not increased in dyspeptic patients with *Helicobacter pylori*-associated gastritis," *Mediators Inflamm* 13(1):25-8 (2004)), enteritis (K. Mitsuyama et al., "STAT3 activation via interleukin 6 transsignalling contributes to ileitis in SAMP1/Yit mice," *Gut* 55(9):1263-9. (2006)), gingivitis (R. Johnson et al., "Interleukin-II and IL-17 and the pathogenesis of periodontal disease," *J Periodontol* 75(1):37-43 (2004)), appendicitis (S. Latifi et al., "Persistent elevation of serum interleukin-6 in intraabdominal sepsis identifies those with prolonged length of stay," *J PediatrSurg* 39(10):1548-52 (2004)), irritable bowel syndrome (M. Ortiz-Lucas et al., "Irritable bowel syndrome immune hypothesis. Part two: the role of cytokines," *Rev Esp Enferm Dig* 102(12):711-7 (2010)), tissue graft rejection (L. Kappel et al., "IL-17 contributes to CD4-mediated graft-versus-host disease," *Blood* 113(4): 945-52 (2009)), chronic obstructive pulmonary disease (COPD) (S. Traves and L. Donnelly, "Th17 cells in airway diseases," *Curr Mol Med* 8(5):416-26 (2008)), septic shock (toxic shock syndrome, SIRS, bacterial sepsis, etc) (E. Nicodeme et al., *Nature* 468(7327):1119-23 (2010)), osteoarthritis (L. Chen et al., "IL-17RA aptamer-mediated repression of IL-6 inhibits synovium inflammation in a murine model of osteoarthritis," *Osteoarthritis Cartilage* 19(6):711-8 (2011)), acute gout (W. Urano et al., "The inflammatory process in the mechanism of decreased serum uric acid concentrations during acute gouty arthritis," *J Rheumatol* 29(9):1950-3 (2002)), acute lung injury (S. Traves and L. Donnelly, "Th17 cells in airway diseases," *Curr Mol Med* 8(5):416-26 (2008)), acute renal failure (E. Simmons et al., "Plasma cytokine levels predict mortality in patients with acute renal failure," *Kidney Int* 65(4):1357-65 (2004)), burns (P. Paquet and G. Pierard, "Interleukin-6 and the skin," *Int Arch Allergy Immunol* 109(4):308-17 (1996)), Herxheimer reaction (G. Kaplanski et al., "Jarisch-Herxheimer reaction complicating the treatment of chronic Q fever endocarditis: elevated TNFalpha and IL-6 serum levels," *J Infect* 37(1):83-4 (1998)), and SIRS associated with viral infections (A. Belkinaand G. Denis, *Nat Rev Cancer* 12(7):465-77 (2012)). Thus, the invention includes compounds of Formula I or Formula Ia, stereoisomers, tautomers, pharmaceutically acceptable salts, or hydrates thereof; pharmaceutical compositions comprising one or more of those compounds; and methods of using those compounds or compositions for treating these diseases.

In one embodiment, BET inhibitor compounds of Formula I or Formula Ia, stereoisomers, tautomers, pharmaceutically acceptable salts, or hydrates thereof, or compositions comprising one or more of those compounds may be used for treating rheumatoid arthritis (RA) and multiple sclerosis (MS). Strong proprietary data exist for the utility of BET inhibitors in preclinical models of RA and MS. R. Jahagirdar et al., "An Orally Bioavailable Small Molecule RVX-297 Significantly Decreases Disease in a Mouse Model of Multiple Sclerosis," *World Congress of Inflammation, Paris, France* (2011). Both RA and MS are characterized by a dysregulation of the IL-6 and IL-17 inflammatory pathways (A. Kimura and T. Kishimoto, "IL-6: regulator of Treg/Th17 balance," *Eur J Immunol* 40(7):1830-5 (2010)) and thus would be especially sensitive to BET inhibition. In another embodiment, BET inhibitor compounds of Formula I or Formula Ia, stereoisomers, tautomers, pharmaceutically acceptable salts, or hydrates thereof may be used for treating sepsis and associated afflictions. BET inhibition has been shown to inhibit development of sepsis, in part, by inhibiting IL-6 expression, in preclinical models in both published (E. Nicodeme et al., *Nature* 468(7327):1119-23 (2010)) and proprietary data.

In one embodiment, BET inhibitor compounds of Formula I or Formula Ia, stereoisomers, tautomers, pharmaceutically acceptable salts, or hydrates thereof, or compositions comprising one or more of those compounds may be used to treat cancer. Cancers that have an overexpression, translocation, amplification, or rearrangement c-myc or other myc family oncoproteins (MYCN, L-myc) are particularly sensitive to BET inhibition. J. Delmore et al., *Cell* 146(6):904-17 (2010); J. Mertz et al., *Proc Natl Acad Sci USA* 108(40): 16669-74 (2011). These cancers include, but are not limited to, B-acute lymphocytic leukemia, Burkitt's lymphoma, Diffuse large cell lymphoma, Multiple myeloma, Primary plasma cell leukemia, Atypical carcinoid lung cancer, Bladder cancer, Breast cancer, Cervix cancer, Colon cancer, Gastric cancer, Glioblastoma, Hepatocellular carcinoma, Large cell neuroendocrine carcinoma, Medulloblastoma, Melanoma, nodular, Melanoma, superficial spreading, Neuroblastoma, esophageal squamous cell carcinoma, Osteosarcoma, Ovarian cancer, Prostate cancer, Renal clear cell carcinoma, Retinoblastoma, Rhabdomyosarcoma, and Small cell lung carcinoma. M. Vita and M. Henriksson, *Semin Cancer Biol* 16(4):318-30 (2006).

In one embodiment, BET inhibitor compounds of Formula I or Formula Ia, stereoisomers, tautomers, pharmaceutically acceptable salts, or hydrates thereof, or compositions comprising one or more of those compounds may be used to treat cancers that result from an aberrant regulation (overexpression, translocation, etc) of BET proteins. These include, but are not limited to, NUT midline carcinoma (Brd3 or Brd4 translocation to nutlin 1 gene) (C. French Cancer Genet Cytogenet 203(1):16-20 (2010)), B-cell lymphoma (Brd2 overexpression) (R. Greenwald et al., *Blood* 103(4):1475-84 (2004)), non-small cell lung cancer (BrdT overexpression) (C. Grunwald et al., "Expression of multiple epigenetically regulated cancer/germline genes in nonsmall cell lung cancer," *Int J Cancer* 118(10):2522-8 (2006)), esophageal cancer and head and neck squamous cell carcinoma (BrdT overexpression) (M. Scanlan et al., "Expression of cancer-testis antigens in lung cancer: definition of bromodomain testis-specific gene (BRDT) as a new CT gene, CT9," *Cancer Lett* 150(2):55-64 (2000)), and colon cancer (Brd4) (R. Rodriguez et al., "Aberrant epigenetic regulation of bromodomain BRD4 in human colon cancer," *J Mol Med* (Berl) 90(5):587-95 (2012)).

In one embodiment, because BET inhibitors decrease Brd-dependent recruitment of pTEFb to genes involved in cell proliferation, BET inhibitor compounds of Formula I or Formula Ia, stereoisomers, tautomers, pharmaceutically acceptable salts, or hydrates thereof, or compositions comprising one or more of those compounds may be used to treat cancers that rely on pTEFb (Cdk9/cyclin T) and BET proteins to regulate oncogenes. These cancers include, but are not limited to, chronic lymphocytic leukemia and multiple myeloma (W. Tong et al., "Phase I and pharmacologic study of SNS-032, a potent and selective Cdk2, 7, and 9 inhibitor, in patients with advanced chronic lymphocytic leukemia and multiple myeloma," *J Clin Oncol* 28(18): 3015-22 (2010)), follicular lymphoma, diffuse large B cell lymphoma with germinal center phenotype, Burkitt's lymphoma, Hodgkin's lymphoma, follicular lymphomas and activated, anaplastic large cell lymphoma (C. Bellan et al., "CDK9/CYCLIN T1 expression during normal lymphoid differentiation and malignant transformation," *J Pathol* 203 (4):946-52 (2004)), neuroblastoma and primary neuroectodermal tumor (G. De Falco et al., "Cdk9 regulates neural differentiation and its expression correlates with the differentiation grade of neuroblastoma and PNET tumors," *Cancer Biol Ther* 4(3):277-81 (2005)), rhabdomyosarcoma (C. Simone and A. Giordano, "Abrogation of signal-dependent activation of the cdk9/cyclin T2a complex in human RD rhabdomyosarcoma cells," *Cell Death Differ* 14(1):192-5 (2007)), prostate cancer (D. Lee et al., "Androgen receptor interacts with the positive elongation factor P-TEFb and enhances the efficiency of transcriptional elongation," *J Biol Chem* 276(13):9978-84 (2001)), and breast cancer (K. Bartholomeeusen et al., "BET bromodomain inhibition activates transcription via a transient release of P-TEFb from 7SK snRNP," *J Biol Chem* (2012)).

In one embodiment, BET inhibitor compounds of Formula I or Formula Ia, stereoisomers, tautomers, pharmaceutically acceptable salts, or hydrates thereof, or compositions comprising one or more of those compounds may be used to treat cancers in which BET-responsive genes, such as CDK6, Bcl2, TYRO3, MYB, and hTERT are up-regulated. M. Dawson et al., *Nature* 478(7370):529-33 (2011); J. Delmore et al., *Cell* 146(6):904-17 (2010). These cancers include, but are not limited to, pancreatic cancer, breast cancer, colon cancer, glioblastoma, adenoid cystic carcinoma, T-cell prolymphocytic leukemia, malignant glioma, bladder cancer, medulloblastoma, thyroid cancer, melanoma, multiple myeloma, Barret's adenocarcinoma, hepatoma, prostate cancer, pro-myelocytic leukemia, chronic lymphocytic leukemia, mantle cell lymphoma, diffuse large B-cell lymphoma, small cell lung cancer, and renal carcinoma. M. Ruden and N. Puri, "Novel anticancer therapeutics targeting telomerase," *Cancer Treat Rev* (2012); P. Kelly and A. Strasser, "The role of Bcl-2 and its pro-survival relatives in tumourigenesis and cancer therapy" *Cell Death Differ* 18(9):1414-24 (2011); T. Uchida et al., "Antitumor effect of bcl-2 antisense phosphorothioate oligodeoxynucleotides on human renal-cell carcinoma cells in vitro and in mice," *Mol Urol* 5(2):71-8 (2001).

Published and proprietary data have shown direct effects of BET inhibition on cell proliferation in various cancers. In one embodiment, BET inhibitor compounds of Formula I or Formula Ia, stereoisomers, tautomers, pharmaceutically acceptable salts, or hydrates thereof, or compositions comprising one or more of those compounds may be used to treat cancers for which exist published and, for some, proprietary, in vivo and/or in vitro data showing a direct effect of BET inhibition on cell proliferation. These cancers include NMC (NUT-midline carcinoma), acute myeloid leukemia (AML), acute B lymphoblastic leukemia (B-ALL), Burkitt's Lymphoma, B-cell Lymphoma, Melanoma, mixed lineage leukemia, multiple myeloma, pro-myelocytic leukemia (PML), and non-Hodgkin's lymphoma. P. Filippakopoulos et al., *Nature* 468(7327):1067-73 (2010); M. Dawson et al., *Nature* 478(7370):529-33 (2011); Zuber, J., et al., "RNAi screen identifies Brd4 as a therapeutic target in acute myeloid leukaemia," *Nature* 478(7370):524-8 (2011); M. Segura, et al, Cancer Research. 72(8): Supplement 1 (2012). The compounds of the invention have a demonstrated BET inhibition effect on cell proliferation in vitro for the following cancers: Neuroblastoma, Medulloblastoma, lung carcinoma (NSCLC, SCLC), and colon carcinoma.

In one embodiment, because of potential synergy or additive effects between BET inhibitors and other cancer therapy, BET inhibitor compounds of Formula I or Formula Ia, stereoisomers, tautomers, pharmaceutically acceptable salts, or hydrates thereof, or compositions comprising one or more of those compounds may be combined with other therapies, chemotherapeutic agents, or anti-proliferative agents to treat human cancer and other proliferative disorders. The list of therapeutic agents which can be combined with BET inhibitors in cancer treatment includes, but is not limited to, ABT-737, Azacitidine (Vidaza), AZD1152 (Barasertib), AZD2281 (Olaparib), AZD6244 (Selumetinib), BEZ235, Bleomycin Sulfate, Bortezomib (Velcade), Busulfan (Myleran), Camptothecin, Cisplatin, Cyclophosphamide (Clafen), CYT387, Cytarabine (Ara-C), Dacarbazine, DAPT (GSI-IX), Decitabine, Dexamethasone, Doxorubicin (Adriamycin), Etoposide, Everolimus (RAD001), Flavopiridol (Alvocidib), Ganetespib (STA-9090), Gefitinib (Iressa), Idarubicin, Ifosfamide (Mitoxana), IFNa2a (Roferon A), Melphalan (Alkeran), Methazolastone (temozolomide), Metformin, Mitoxantrone (Novantrone), Paclitaxel, Phenformin, PKC412 (Midostaurin), PLX4032 (Vemurafenib), Pomalidomide (CC-4047), Prednisone (Deltasone), Rapamycin, Revlimid (Lenalidomide), Ruxolitinib (INCB018424), Sorafenib (Nexavar), SU11248 (Sunitinib), SU11274, Vinblastine, Vincristine (Oncovin), Vinorelbine (Navelbine), Vorinostat (SAHA), and WP1130 (Degrasyn).

In one embodiment, BET inhibitor compounds of Formula I or Formula Ia, stereoisomers, tautomers, pharmaceutically acceptable salts, or hydrates thereof, or compositions comprising one or more of those compounds may be used to treat benign proliferative and fibrotic disorders, including benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, juvenile polyposis syndrome, idiopathic pulmonary fibrosis, renal fibrosis, post-operative stricture, keloid formation, scleroderma, and cardiac fibrosis. X. Tang et al., Am J Pathology in press (2013).

In one embodiment, because of their ability to up-regulate ApoA-1 transcription and protein expression (O. Mirguet et al., *Bioorg Med Chem Lett* 22(8):2963-7 (2012); C. Chung et al., *J Med Chem* 54(11):3827-38 (2011)), BET inhibitor compounds of Formula I or Formula Ia, stereoisomers, tautomers, pharmaceutically acceptable salts, or hydrates thereof, or compositions comprising one or more of those compounds may be used to treat cardiovascular diseases that are generally associated with including dyslipidemia, atherosclerosis, hypercholesterolemia, and metabolic syndrome (A. Belkina and G. Denis, *Nat Rev Cancer* 12(7):465-77 (2012); G. Denis *Discov Med* 10(55):489-99 (2010)). In another embodiment, BET inhibitor compounds of Formula I or Formula Ia, stereoisomers, tautomers, pharmaceutically acceptable salts, or hydrates thereof, may be used to treat non-cardiovascular disease characterized by deficits in ApoA-1, including Alzheimer's disease. D. Elliott et al., *Clin Lipidol* 51(4):555-573 (2010).

In one embodiment, BET inhibitor compounds of Formula I or Formula Ia, stereoisomers, tautomers, pharmaceutically acceptable salts, or hydrates thereof, or compositions comprising one or more of those compounds may be used in patients with insulin resistance and type II diabetes. A. Belkina and G. Denis, *Nat Rev Cancer* 12(7):465-77 (2012); G. Denis *Discov Med* 10(55):489-99 (2010); F. Wang et al., *Biochem J* 425(1):71-83 (2010); G. Denis et al, *FEBS Lett* 584(15):3260-8 (2010). The anti-inflammatory effects of BET inhibition would have additional value in decreasing inflammation associated with diabetes and metabolic disease. K. Alexandraki et al., "Inflammatory process in type 2 diabetes: The role of cytokines," *Ann NY Acad Sci* 1084: 89-117 (2006).

In one embodiment, because of their ability to down-regulate viral promoters, BET inhibitor compounds of Formula I or Formula Ia, stereoisomers, tautomers, pharmaceutically acceptable salts, or hydrates thereof, or compositions comprising one or more of those compounds may be used as therapeutics for cancers that are associated with viruses including Epstein-Barr Virus (EBV), hepatitis virus (HBV, HCV), Kaposi's sarcoma associated virus (KSHV), human papilloma virus (HPV), Merkel cell polyomavirus, and human cytomegalovirus (CMV). D. Gagnon et al., *J Virol* 83(9):4127-39 (2009); J. You et al., *J Virol* 80(18):8909-19 (2006); R. Palermo et al., "RNA polymerase II stalling promotes nucleosome occlusion and pTEFb recruitment to drive immortalization by Epstein-Barr virus," *PLoS Pathog* 7(10):e1002334 (2011); E. Poreba et al., "Epigenetic mechanisms in virus-induced tumorigenesis," *Clin Epigenetics* 2(2):233-47. 2011. In another embodiment, because of their ability to reactivate HIV-1 in models of latent T cell infection and latent monocyte infection, BET inhibitors could be used in combination with anti-retroviral therapeutics for treating HIV. J. Zhu, et al., *Cell Rep* (2012); C. Banerjee et al., *J Leukoc Biol* (2012); K. Bartholomeeusen et al., *J Biol Chem* (2012); Z. Li et al., *Nucleic Acids Res* (2012.)

In one embodiment, because of the role of epigenetic processes and bromodomain-containing proteins in neurological disorders, BET inhibitor compounds of Formula I or Formula Ia, stereoisomers, tautomers, pharmaceutically acceptable salts, or hydrates thereof, or compositions comprising one or more of those compounds may be used to treat diseases including, but not limited to, Alzheimer's disease, Parkinson's disease, Huntington disease, bipolar disorder, schizophrenia, Rubinstein-Taybi syndrome, and epilepsy. R. Prinjha et al., *Trends PharmacolSci* 33(3):146-53 (2012); S. Muller et al., "Bromodomains as therapeutic targets," *Expert Rev Mol Med* 13:e29 (2011).

In one embodiment, because of the effect of BRDT depletion or inhibition on spermatid development, BET inhibitor compounds of Formula I or Formula Ia, stereoisomers, tautomers, pharmaceutically acceptable salts, or hydrates thereof, or compositions comprising one or more of those compounds may be used as reversible, male contraceptive agents. M. Matzuk et al., "Small-Molecule Inhibition of BRDT for Male Contraception," *Cell* 150(4): p. 673-684 (2012); B. Berkovits et al., "The testis-specific double bromodomain-containing protein BRDT forms a complex with multiple spliceosome components and is required for mRNA splicing and 3'-UTR truncation in round spermatids," *Nucleic Acids Res* 40(15):7162-75 (2012).

Pharmaceutical Compositions

Pharmaceutical compositions of the present disclosure comprise at least one compound of Formula I or Formula Ia, or tautomer, stereoisomer, pharmaceutically acceptable salt or hydrate thereof formulated together with one or more pharmaceutically acceptable carriers. These formulations include those suitable for oral, rectal, topical, buccal and parenteral (e.g., subcutaneous, intramuscular, intradermal, or intravenous) administration. The most suitable form of administration in any given case will depend on the degree and severity of the condition being treated and on the nature of the particular compound being used.

Formulations suitable for oral administration may be presented in discrete units, such as capsules, cachets, lozenges, or tablets, each containing a predetermined amount of a compound of the present disclosure as powder or granules; as a solution or a suspension in an aqueous or non-aqueous liquid; or as an oil-in-water or water-in-oil emulsion. As indicated, such formulations may be prepared by any suitable method of pharmacy which includes the step of bringing into association at least one compound of the present disclosure as the active compound and a carrier or excipient (which may constitute one or more accessory ingredients). The carrier must be acceptable in the sense of being compatible with the other ingredients of the formulation and must not be deleterious to the recipient. The carrier may be a solid or a liquid, or both, and may be formulated with at least one compound described herein as the active compound in a unit-dose formulation, for example, a tablet, which may contain from about 0.05% to about 95% by weight of the at least one active compound. Other pharmacologically active substances may also be present including other compounds. The formulations of the present disclosure may be prepared by any of the well-known techniques of pharmacy consisting essentially of admixing the components.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by, for example, dissolving or dispersing, at least one active compound of the present disclosure as described herein and optional pharmaceutical adjuvants in an excipient, such as, for example, water, saline, aqueous dextrose, glycerol, ethanol, and the like, to thereby form a solution or suspension. In general, suitable formulations may be prepared by uniformly and intimately admixing the at least one active compound of the present disclosure with a liquid or finely divided solid carrier, or both, and then, if necessary, shaping the product. For example, a tablet may be prepared by compressing or molding a powder or granules of at least one compound of the present disclosure, which may be optionally combined with one or more accessory ingredients. Compressed tablets may be prepared by compressing, in a suitable machine, at least one compound of the present disclosure in a free-flowing form, such as a powder or granules, which may be optionally mixed with a binder, lubricant, inert diluent and/or surface active/dispersing agent(s). Molded tablets may be made by molding, in a suitable machine, where the powdered form of at least one compound of the present disclosure is moistened with an inert liquid diluent.

Formulations suitable for buccal (sub-lingual) administration include lozenges comprising at least one compound of the present disclosure in a flavored base, usually sucrose and acacia or tragacanth, and pastilles comprising the at least one compound in an inert base such as gelatin and glycerin or sucrose and acacia.

Formulations of the present disclosure suitable for parenteral administration comprise sterile aqueous preparations of at least one compound of Formula I or Formula Ia or tautomer, stereoisomer, pharmaceutically acceptable salt, or hydrate thereof, which are approximately isotonic with the blood of the intended recipient. These preparations are administered intravenously, although administration may also be effected by means of subcutaneous, intramuscular, or intradermal injection. Such preparations may conveniently be prepared by admixing at least one compound described herein with water and rendering the resulting solution sterile and isotonic with the blood. Injectable compositions according to the present disclosure may contain from about 0.1 to about 5% w/w of the active compound.

Formulations suitable for rectal administration are presented as unit-dose suppositories. These may be prepared by admixing at least one compound as described herein with one or more conventional solid carriers, for example, cocoa butter, and then shaping the resulting mixture.

Formulations suitable for topical application to the skin may take the form of an ointment, lotion, paste, gel, spray, aerosol, or oil. Carriers and excipients which may be used include Vaseline, lanoline, polyethylene glycols, alcohols, and combinations of two or more thereof. The active compound (i.e., at least one compound of Formula I or Formula Ia or tautomer, stereoisomer, pharmaceutically acceptable salt, or hydrate thereof) is generally present at a concentration of from about 0.1% to about 15% w/w of the composition, for example, from about 0.5 to about 2%.

The amount of active compound administered may be dependent on the subject being treated, the subject's weight, the manner of administration and the judgment of the prescribing physician. For example, a dosing schedule may involve the daily or semi-daily administration of the encapsulated compound at a perceived dosage of about 1 µg to about 1000 mg. In another embodiment, intermittent administration, such as on a monthly or yearly basis, of a dose of the encapsulated compound may be employed. Encapsulation facilitates access to the site of action and allows the administration of the active ingredients simultaneously, in theory producing a synergistic effect. In accordance with standard dosing regimens, physicians will readily determine optimum dosages and will be able to readily modify administration to achieve such dosages.

A therapeutically effective amount of a compound or composition disclosed herein can be measured by the therapeutic effectiveness of the compound. The dosages, however, may be varied depending upon the requirements of the patient, the severity of the condition being treated, and the compound being used. In one embodiment, the therapeutically effective amount of a disclosed compound is sufficient to establish a maximal plasma concentration. Preliminary doses as, for example, determined according to animal tests, and the scaling of dosages for human administration is performed according to art-accepted practices.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferable.

Data obtained from the cell culture assays or animal studies can be used in formulating a range of dosage for use in humans. Therapeutically effective dosages achieved in one animal model may be converted for use in another animal, including humans, using conversion factors known in the art (see, e.g., Freireich et al., *Cancer Chemother. Reports* 50(4):219-244 (1966) and Table 1 for Equivalent Surface Area Dosage Factors).

TABLE 1

Equivalent Surface Area Dosage Factors:

| From: | To: | | | | |
|---|---|---|---|---|---|
| | Mouse (20 g) | Rat (150 g) | Monkey (3.5 kg) | Dog (8 kg) | Human (60 kg) |
| Mouse | 1 | ½ | ¼ | ⅙ | 1/12 |
| Rat | 2 | 1 | ½ | ¼ | 1/7 |
| Monkey | 4 | 2 | 1 | ⅗ | ⅓ |
| Dog | 6 | 4 | ⅗ | 1 | ½ |
| Human | 12 | 7 | 3 | 2 | 1 |

The dosage of such compounds lies preferably within a range of circulating concentrations that include the $ED_{50}$ with little or no toxicity. The dosage may vary within this range depending upon the dosage form employed and the route of administration utilized. Generally, a therapeutically effective amount may vary with the subject's age, condition, and gender, as well as the severity of the medical condition in the subject. The dosage may be determined by a physician and adjusted, as necessary, to suit observed effects of the treatment.

In one embodiment, a compound of Formula I or Formula Ia or a tautomer, stereoisomer, pharmaceutically acceptable salt or hydrate thereof, is administered in combination with another therapeutic agent. The other therapeutic agent can provide additive or synergistic value relative to the administration of a compound of the present disclosure alone. The therapeutic agent can be, for example, a statin; a PPAR agonist, e.g., a thiazolidinedione or fibrate; a niacin, a RVX, FXR or LXR agonist; a bile-acid reuptake inhibitor; a cholesterol absorption inhibitor; a cholesterol synthesis inhibitor; a cholesteryl ester transfer protein (CETP), an ion-exchange resin; an antioxidant; an inhibitor of AcylCoA cholesterol acyltransferase (ACAT inhibitor); a tyrophostine; a sulfonylurea-based drug; a biguanide; an alpha-glucosidase inhibitor; an apolipoprotein E regulator; a HMG-CoA reductase inhibitor, a microsomal triglyceride transfer protein; an LDL-lowing drug; an HDL-raising drug; an HDL enhancer; a regulator of the apolipoprotein A-IV and/or apolipoprotein genes; or any cardiovascular drug.

In another embodiment, a compound of Formula I or Formula Ia or a tautomer, stereoisomer, pharmaceutically acceptable salt or hydrate thereof, is administered in combination with one or more anti-inflammatory agents. Anti-inflammatory agents can include immunosuppressants, TNF inhibitors, corticosteroids, non-steroidal anti-inflammatory drugs (NSAIDs), disease-modifying anti-rheumatic drugs (DMARDS), and the like. Exemplary anti-inflammatory agents include, for example, prednisone; methylprenisolone (Medrol®), triamcinolone, methotrexate (Rheumatrex®, Trexall®), hydroxychloroquine (Plaquenil®), sulfasalzine (Azulfidine®), leflunomide (Arava®), etanercept (Enbrel®), infliximab (Remicade®), adalimumab (Humira®), rituximab (Rituxan®), abatacept (Orencia®), interleukin-1, anakinra (Kineret™), ibuprofen, ketoprofen, fenoprofen, naproxen, aspirin, acetominophen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine, or sulfasalazine.

LIST OF EXEMPLARY EMBODIMENTS

1. A compound of Formula I:

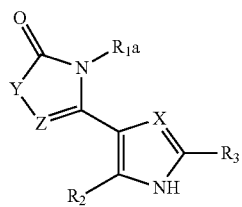

Formula I or a stereoisomer, tautomer, pharmaceutically acceptable salt, or hydrate thereof, wherein:

X is selected from CH and N;
Y is selected from —NH, —N—$R_{1b}$, and oxygen;
Z is selected from N, and —CH—;
$R_{1a}$ and $R_{1b}$ are independently selected from alkyl ($C_1$-$C_6$), carbocycle ($C_3$-$C_{10}$), heterocycle ($C_2$-$C_{10}$) optionally substituted with 1 to 3 groups selected from $R_4$;
$R_2$ is selected from aryl ($C_5$-$C_{10}$) and heteroaryl ($C_5$-$C_{10}$) optionally substituted with 1 to 5 groups selected from $R_5$;
$R_3$ is selected from carbocycle ($C_3$-$C_{10}$) and heterocycle ($C_2$-$C_{10}$) optionally substituted with 1 to 5 groups selected from $R_5$;
each $R_4$ is independently selected from deuterium, alkyl ($C_1$-$C_6$), cycloalkyl ($C_3$-$C_8$), alkoxy ($C_1$-$C_6$), amino, —NHC(O)NH-alkyl($C_1$-$C_6$), halogen, amide, —$CF_3$, —CN, —$N_3$, ketone, —S(O)-alkyl ($C_1$-$C_4$), —$SO_2$-alkyl($C_1$-$C_6$), thioalkyl($C_1$-$C_6$), —COOH, and ester, each of which may be optionally substituted with hydrogen, F, Cl, Br, —OH, —$NH_2$, —NHMe, —OMe, —SMe, oxo, and/or thio-oxo; and
each $R_5$ is independently selected from deuterium, alkyl ($C_1$-$C_6$), alkoxy($C_1$-$C_6$), amino, —NHC(O)NH-alkyl($C_1$-$C_6$), halogen, amide, —$CF_3$, —CN, —$N_3$, ketone, —S(O)-alkyl($C_1$-$C_4$), —$SO_2$-alkyl ($C_1$-$C_6$), thioalkyl($C_1$-$C_6$), —COOH, and ester, each of which may be optionally substituted with hydrogen, F, Cl, Br, —OH, —$NH_2$, —NHMe, —OMe, —SMe, oxo, and/or thio-oxo.

2. A compound according to embodiment 1, wherein the compound is a compound of Formula Ia:

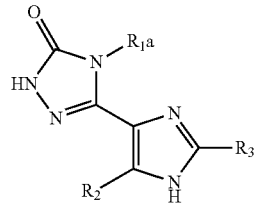

Formula Ia or a stereoisomer, tautomer, pharmaceutically acceptable salt, or hydrate thereof, wherein:
$R_{1a}$ is selected from alkyl ($C_1$-$C_6$), carbocycle ($C_3$-$C_{10}$), heterocycle ($C_2$-$C_{10}$) optionally substituted with 1 to 3 groups selected from $R_4$;
$R_2$ is selected from aryl ($C_5$-$C_{10}$) and heteroaryl ($C_5$-$C_{10}$) optionally substituted with 1 to 5 groups selected from $R_5$;
$R_3$ is selected from carbocycle ($C_3$-$C_{10}$) and heterocycle ($C_2$-$C_{10}$) optionally substituted with 1 to 5 groups selected from $R_5$;
each $R_4$ is independently selected from deuterium, alkyl ($C_1$-$C_6$), cycloalkyl ($C_3$-$C_8$), alkoxy ($C_1$-$C_6$), amino, —NHC(O)NH-alkyl($C_1$-$C_6$), halogen, amide, —$CF_3$, —CN, —$N_3$, ketone, —S(O)-alkyl ($C_1$-$C_4$), —$SO_2$-alkyl($C_1$-$C_6$), thioalkyl($C_1$-$C_6$), —COOH, and ester, each of which may be optionally substituted with hydrogen, F, Cl, Br, —OH, —$NH_2$, —NHMe, —OMe, —SMe, oxo, and/or thio-oxo; and
each $R_5$ is independently selected from deuterium, alkyl ($C_1$-$C_6$), alkoxy ($C_1$-$C_6$), amino, —NHC(O)NH-alkyl($C_1$-$C_6$), halogen, amide, —$CF_3$, —CN, —N₃, ketone (C₁-C₆), —S(O)-alkyl(C₁-C₄), —SO₂-alkyl(C₁-C₆), thioalkyl(C₁-C₆), —COOH, and ester, each of which may be optionally substituted with hydrogen, F, Cl, Br, —OH, —NH₂, —NHMe, —OMe, —SMe, oxo, and/or thio-oxo.

3. The compound according to embodiment 1, wherein X is N.
4. The compound according to embodiment 1, wherein X is CH.
5. The compound according to embodiment 1, wherein Y is —NR$_{1b}$.
6. The compound according to embodiment 1, wherein Y is —NH.
7. The compound according to embodiment 1, wherein Y is oxygen.
8. The compound according to embodiment 1, wherein Z is N.
9. The compound according to embodiment 1, wherein Z is CH.
10. The compound according to embodiment 1 or embodiment 2, wherein each R₄ is independently selected from deuterium, alkyl (C₁-C₆), alkoxy (C₁-C₆), amino, —NHC(O)NH— alkyl(C₁-C₆), halogen, amide, —CF₃, —CN, —N₃, ketone, —S(O)-alkyl(C₁-C₄), —SO₂-alkyl(C₁-C₆), thioalkyl(C₁-C₆), —COOH, and ester, each of which may be optionally substituted with hydrogen, F, Cl, Br, —OH, —NH₂, —NHMe, —OMe, —SMe, oxo, and/or thio-oxo.
11. The compound according to any one of embodiments 1-10, wherein R$_{1a}$ is selected from alkyl (C₁-C₆), carbocycle (C₃-C₆), and heterocycle (C₂-C₅) optionally substituted with 1 to 3 groups selected from R₄.
12. The compound according to any one of embodiments 1-11, wherein R$_{1a}$ is selected from alkyl (C₁-C₆) and carbocycle (C₃-C₆) optionally substituted with 1 to 3 groups selected from R₄.
13. The compound according to any one of embodiments 1-12, wherein R$_{1a}$ is selected from the following structures, which may be optionally substituted with 1 to 3 groups selected from R₄:

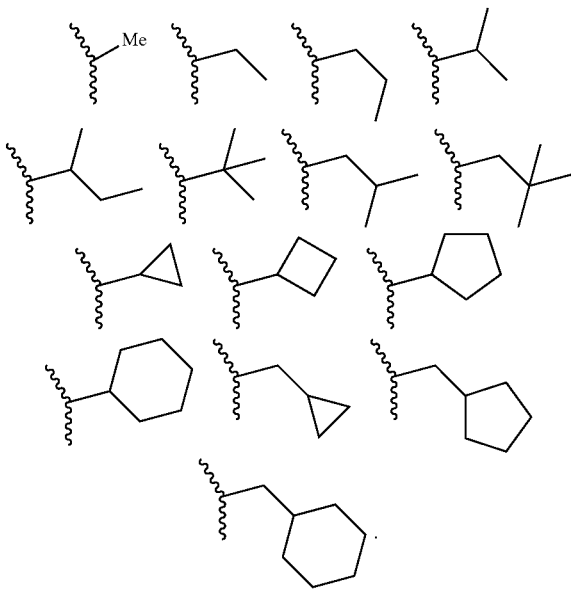

14. The compound according to any one of embodiments 1-13, wherein R$_{1a}$ is selected from the following structures, which may be optionally substituted with 1 to 3 groups selected from R₄:

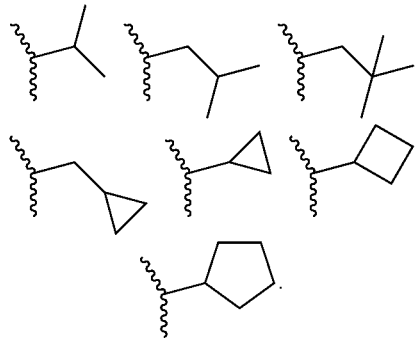

15. The compound according to any one of embodiments 1-14, wherein R$_{1a}$ is

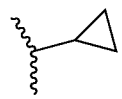

optionally substituted with 1 to 3 groups selected from R₄.

16. The compound according to any one of embodiments 1-15, wherein R$_{1a}$ is

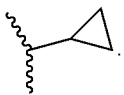.

17. The compound according to any one of embodiments 1-11, wherein R$_{1a}$ is selected from the following structures, which may be optionally substituted with 1 to 3 groups selected from R₄:

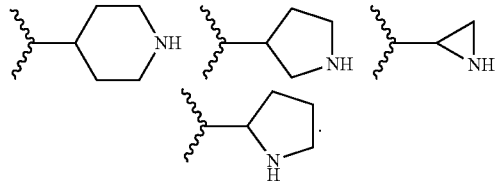

18. The compound according to any one of embodiments 1, 3-5, and 7-17, wherein R$_{1b}$ is alkyl (C₁-C₆).
19. The compound according to any one of embodiments 1, 3-5, and 7-18, wherein R$_{1b}$ is selected from methyl and ethyl.
20. The compound according to any one of embodiments 1, 3-5, and 7-19, wherein R$_{1b}$ is methyl.
21. The compound according to any one of embodiments 1-20, wherein R₂ is selected from bicyclic aryl and bicyclic heteroaryl groups optionally substituted with 1 to 5 R₅ groups.
22. The compound according to any one of embodiments 1-21, wherein R₂ is selected from aryl (C₅-C₁₀) optionally substituted with 1 to 5 groups selected from R₅.
23. The compound according to any one of embodiments 1-21, wherein R₂ is selected from heteroaryl (C₅-C₁₀) optionally substituted with 1 to 5 groups selected from R₅.

24. The compound according to any one of embodiments 1-23, wherein $R_2$ is selected from the following structures, which may be optionally substituted with 1 to 5 groups selected from $R_5$:

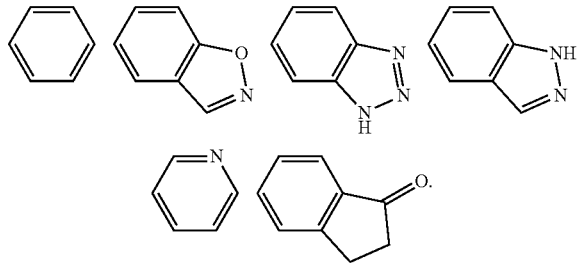

25. The compound according to any one of embodiments 1-24, wherein $R_2$ is selected from the following structures, which may be optionally substituted with 1 to 5 groups selected from $R_5$:

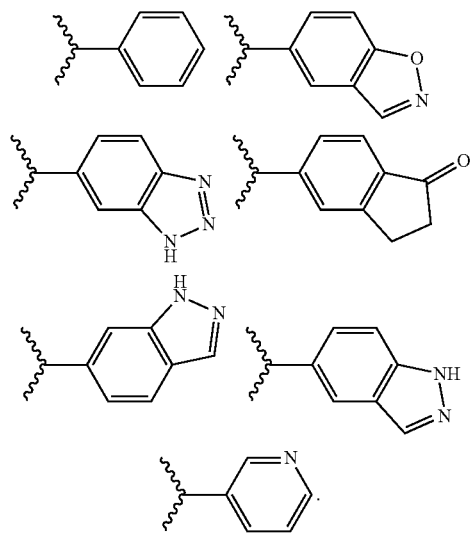

26. The compound according to any one of embodiments 1-25, wherein $R_2$ is selected from the following:

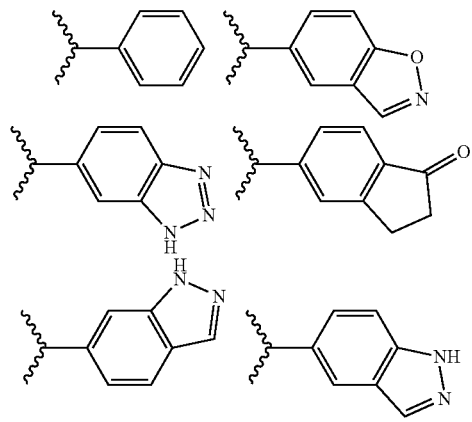

-continued

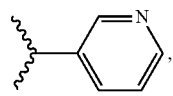

which may be optionally substituted with 1 to 2 groups selected from alkyl ($C_1$-$C_6$), halogen, ketone, amide, and ester.

27. The compound according to any one of embodiments 1-26, wherein $R_2$ is selected from the following:

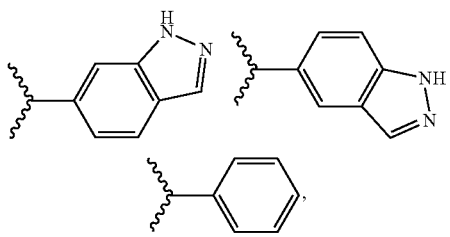

which may be optionally substituted with 1 to 2 groups selected from alkyl ($C_1$-$C_6$), halogen, ketone, amide, and ester.

28. The compound according to any one of embodiments 1-27, wherein $R_2$ is selected from the following structures, which may be optionally substituted with 1 to 5 groups selected from $R_5$:

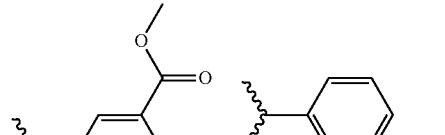

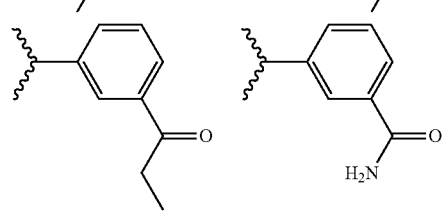

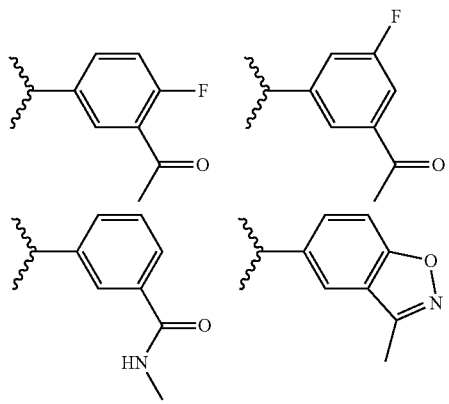

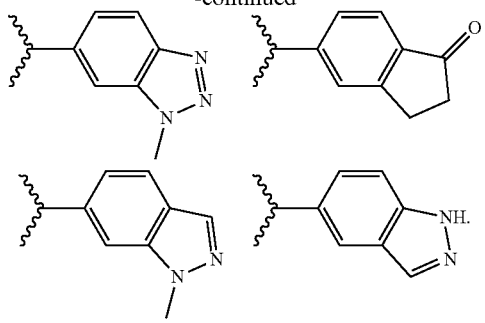

29. The compound according to any one of embodiments 1-21 or 23-28, wherein $R_2$ is

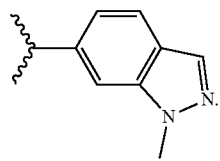 [SMILES: *c1ccc2cnn(C)c2c1]

30. The compound according to any one of embodiments 1-29, wherein $R_3$ is selected from carbocycle $(C_3-C_{10})$ optionally substituted with 1 to 5 groups selected from $R_5$.
31. The compound according to any one of embodiments 1-30, wherein $R_3$ is selected from aryl groups $(C_5-C_{10})$ optionally substituted with 1 to 5 groups selected from $R_5$.
32. The compound according to any one of embodiments 1-29, wherein $R_3$ is selected from heterocycle $(C_2-C_{10})$ optionally substituted with 1 to 5 groups selected from $R_5$.
33. The compound according to any one of embodiments 1-32, wherein $R_3$ is selected from the following structures, which may be optionally substituted with 1 to 5 groups selected from $R_5$:

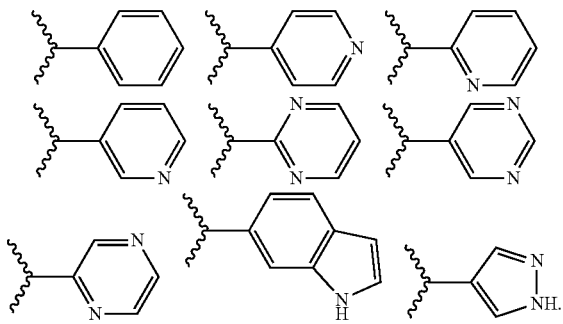

34. The compound according to any one of embodiments 1-33, wherein $R_3$ is selected from the following structures, which may be optionally substituted with 1 to 5 groups selected from $R_5$:

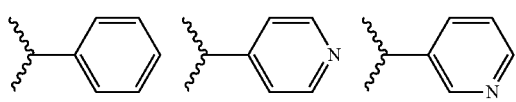

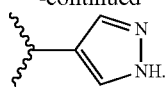

35. The compound according to any one of embodiments 1-34, wherein $R_3$ is selected from the following structures, which may be optionally substituted with alkyl $(C_1-C_6)$:

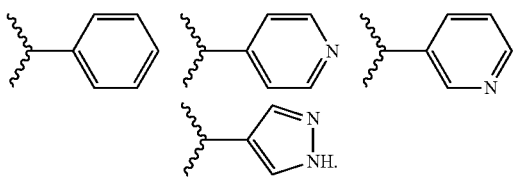

36. The compound according to any one of embodiments 1-35, wherein $R_3$ is selected from the following structures:

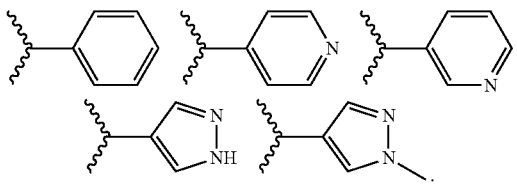

37. The compound according to any one of embodiments 1-36, wherein $R_3$ is selected from phenyl groups which may be optionally substituted with 1 to 5 groups selected from $R_5$.
38. The compound according to any one of embodiments 1-37, wherein $R_3$ is an unsubstituted phenyl group.
39. The compound according to any one of embodiments 1-38, wherein each $R_4$ is independently selected from deuterium, alkyl $(C_1-C_6)$, alkoxy $(C_1-C_6)$, amino, —NHC(O)NH-alkyl$(C_1-C_6)$, halogen, amide, —$CF_3$, —CN, —$N_3$, ketone, —S(O)-alkyl$(C_1-C_4)$, —$SO_2$-alkyl$(C_1-C_6)$, and thioalkyl$(C_1-C_6)$.
40. The compound according to any one of embodiments 1-39, wherein each $R_4$ is independently selected from deuterium, alkyl $(C_1-C_3)$, alkoxy $(C_1-C_3)$, and halogen.
41. The compound according to any one of embodiments 1-40, wherein each $R_5$ is independently selected from deuterium, alkyl $(C_1-C_6)$, alkoxy $(C_1-C_6)$, amino, —NHC(O)NH-alkyl$(C_1-C_6)$, halogen, amide, —$CF_3$, —CN, —$N_3$, ketone, —S(O)-alkyl$(C_1-C_4)$, —$SO_2$-alkyl$(C_1-C_6)$, thioalkyl$(C_1-C_6)$, —COOH, and ester.
42. The compound according to embodiment 1 or embodiment 2, wherein the compound of Formula I or Formula Ia is selected from:
3-(5-(3-Acetylphenyl)-2-phenyl-1H-imidazol-4-yl)-4-cyclopropyl-1H-1,2,4-triazol-5(4H)-one;
Methyl 3-(4-(4-cyclopropyl-5-oxo-4,5-dihydro-1H-1,2,4-triazol-3-yl)-2-phenyl-1H-imidazol-5-yl)-4-methylbenzoate;
3-(4-(4-Cyclopropyl-5-oxo-4,5-dihydro-1H-1,2,4-triazol-3-yl)-2-phenyl-1H-imidazol-5-yl)-N-methylbenzamide;
3-(4-(4-Cyclopropyl-5-oxo-4,5-dihydro-1H-1,2,4-triazol-3-yl)-2-phenyl-1H-imidazol-5-yl)benzamide;
4-Cyclopropyl-3-(5-(3-oxo-2,3-dihydro-1H-inden-5-yl)-2-phenyl-1H-imidazol-4-yl)-1H-1,2,4-triazol-5(4H)-one;

4-Cyclopropyl-3-(2-phenyl-5-(3-propionylphenyl)-1H-imidazol-4-yl)-1H-1,2,4-triazol-5(4H)-one;
4-Cyclopropyl-3-(5-(1-methyl-1H-indazol-6-yl)-2-phenyl-1H-imidazol-4-yl)-1H-1,2,4-triazol-5(4H)-one;
3-(5-(3-Acetyl-4-fluorophenyl)-2-phenyl-1H-imidazol-4-yl)-4-cyclopropyl-1H-1,2,4-triazol-5(4H)-one;
3-(5-(3-Acetyl-5-fluorophenyl)-2-phenyl-1H-imidazol-4-yl)-4-cyclopropyl-1H-1,2,4-triazol-5(4H)-one;
4-cyclopropyl-3-(5-(1-methyl-1H-indazol-5-yl)-2-phenyl-1H-imidazol-4-yl)-1H-1,2,4-triazol-5(4H)-one;
3-(5-(5-acetyl-2-methylphenyl)-2-phenyl-1H-imidazol-4-yl)-4-cyclopropyl-1H-1,2,4-triazol-5(4H)-one;
3-(5-(5-acetylpyridin-3-yl)-2-phenyl-1H-imidazol-4-yl)-4-cyclopropyl-1H-1,2,4-triazol-5(4H)-one formate;
4-cyclopropyl-3-(5-(1,3-dimethyl-1H-indazol-5-yl)-2-phenyl-1H-imidazol-4-yl)-1H-1,2,4-triazol-5(4H)-one;
4-(Cyclopropylmethyl)-3-(5-(1-methyl-1H-indazol-6-yl)-2-phenyl-1H-imidazol-4-yl)-1H-1,2,4-triazol-5(4H)-one;
4-Isopropyl-3-(5-(1-methyl-1H-indazol-6-yl)-2-phenyl-1H-imidazol-4-yl)-1H-1,2,4-triazol-5(4H)-one;
4-(tert-Butyl)-3-(5-(1-methyl-1H-indazol-6-yl)-2-phenyl-1H-imidazol-4-yl)-1H-1,2,4-triazol-5(4H)-one;
4-Cyclopentyl-3-(5-(1-methyl-1H-indazol-6-yl)-2-phenyl-1H-imidazol-4-yl)-1H-1,2,4-triazol-5(4H)-one;
4-Cyclobutyl-3-(5-(1-methyl-1H-indazol-6-yl)-2-phenyl-1H-imidazol-4-yl)-1H-1,2,4-triazol-5(4H)-one;
4-Cyclohexyl-3-(5-(1-methyl-1H-indazol-6-yl)-2-phenyl-1H-imidazol-4-yl)-1H-1,2,4-triazol-5(4H)-one;
4-Isobutyl-3-(5-(1-methyl-1H-indazol-6-yl)-2-phenyl-1H-imidazol-4-yl)-1H-1,2,4-triazol-5(4H)-one;
3-(5-(1-Methyl-1H-indazol-6-yl)-2-phenyl-1H-imidazol-4-yl)-4-neopentyl-1H-1,2,4-triazol-5(4H)-one;
4-Cyclopropyl-1-methyl-3-(5-(1-methyl-1H-indazol-6-yl)-2-phenyl-1H-imidazol-4-yl)-1H-1,2,4-triazol-5(4H)-one;
4-Cyclopropyl-1-ethyl-3-(5-(1-methyl-1H-indazol-6-yl)-2-phenyl-1H-imidazol-4-yl)-1H-1,2,4-triazol-5(4H)-one;
4-Cyclopropyl-1-(cyclopropylmethyl)-3-(5-(1-methyl-1H-indazol-6-yl)-2-phenyl-1H-imidazol-4-yl)-1H-1,2,4-triazol-5(4H)-one;
4-Cyclopropyl-1-(2-methoxyethyl)-3-(5-(1-methyl-1H-indazol-6-yl)-2-phenyl-1H-imidazol-4-yl)-1H-1,2,4-triazol-5(4H)-one;
4-Cyclopropyl-3-(5-(3-methyl benzo[d]isoxazol-5-yl)-2-phenyl-1H-imidazol-4-yl)-1H-1,2,4-triazol-5(4H)-one;
4-Cyclopropyl-3-(5-(1-methyl-1H-benzo[d][1,2,3]triazol-6-yl)-2-phenyl-1H-imidazol-4-yl)-1H-1,2,4-triazol-5(4H)-one;
4-Cyclopropyl-3-(5-(3-methyl-1H-indazol-5-yl)-2-phenyl-1H-imidazol-4-yl)-1H-1,2,4-triazol-5(4H)-one;
4-Cyclopropyl-3-(5-(1-methyl-1H-indazol-6-yl)-2-(pyridin-4-yl)-1H-imidazol-4-yl)-1H-1,2,4-triazol-5(4H)-one;
4-Cyclopropyl-3-(5-(1-methyl-1H-indazol-6-yl)-2-(pyridin-3-yl)-1H-imidazol-4-yl)-1H-1,2,4-triazol-5(4H)-one;
3-(2-(1H-Indol-6-yl)-5-(1-methyl-1H-indazol-6-yl)-1H-imidazol-4-yl)-4-cyclopropyl-1H-1,2,4-triazol-5(4H)-one;
4-Cyclopropyl-3-(5-(1-methyl-1H-indazol-6-yl)-2-(1H-pyrazol-4-yl)-1H-imidazol-4-yl)-1H-1,2,4-triazol-5(4H)-one;
4-Cyclopropyl-3-(5-(1-methyl-1H-indazol-6-yl)-2-(1-methyl-1H-pyrazol-4-yl)-1H-imidazol-4-yl)-1H-1,2,4-triazol-5(4H)-one;
and stereoisomers, tautomers, pharmaceutically acceptable salts, and hydrates thereof.

43. The compound of embodiment 1 or embodiment 2, wherein the compound of Formula I or Formula Ia is selected from the following:

3-(5-(3-acetylphenyl)-2-phenyl-1H-imidazol-4-yl)-4-cyclopropyl-1H-1,2,4-triazol-5(4H)-one hydrochloride;
methyl 3-(4-(4-cyclopropyl-5-oxo-4,5-dihydro-1H-1,2,4-triazol-3-yl)-2-phenyl-1H-imidazol-5-yl)-4-methyl benzoate hydrochloride;
3-(4-(4-cyclopropyl-5-oxo-4,5-dihydro-1H-1,2,4-triazol-3-yl)-2-phenyl-1H-imidazol-5-yl)-N-methyl benzamide hydrochloride;
3-(4-(4-cyclopropyl-5-oxo-4,5-dihydro-1H-1,2,4-triazol-3-yl)-2-phenyl-1H-imidazol-5-yl) benzamide hydrochloride;
4-cyclopropyl-3-(5-(3-oxo-2,3-dihydro-1H-inden-5-yl)-2-phenyl-1H-imidazol-4-yl)-1H-1,2,4-triazol-5(4H)-one hydrochloride;
4-cyclopropyl-3-(2-phenyl-5-(3-propionylphenyl)-1H-imidazol-4-yl)-1H-1,2,4-triazol-5(4H)-one hydrochloride;
4-cyclopropyl-3-(5-(1-methyl-1H-indazol-6-yl)-2-phenyl-1H-imidazol-4-yl)-1H-1,2,4-triazol-5(4H)-one hydrochloride;
3-(5-(3-acetyl-4-fluorophenyl)-2-phenyl-1H-imidazol-4-yl)-4-cyclopropyl-1H-1,2,4-triazol-5(4H)-one hydrochloride;
3-(5-(3-acetyl-5-fluorophenyl)-2-phenyl-1H-imidazol-4-yl)-4-cyclopropyl-1H-1,2,4-triazol-5(4H)-one hydrochloride;
4-cyclopropyl-3-(5-(1-methyl-1H-indazol-5-yl)-2-phenyl-1H-imidazol-4-yl)-1H-1,2,4-triazol-5(4H)-one hydrochloride;
3-(5-(5-acetyl-2-methylphenyl)-2-phenyl-1H-imidazol-4-yl)-4-cyclopropyl-1H-1,2,4-triazol-5(4H)-one hydrochloride;
4-cyclopropyl-3-(5-(3-methyl-1H-indazol-5-yl)-2-phenyl-1H-imidazol-4-yl)-1H-1,2,4-triazol-5(4H)-one hydrochloride;
4-cyclopropyl-3-(5-(1-methyl-1H-benzo[d][1,2,3]triazol-6-yl)-2-phenyl-1H-imidazol-4-yl)-1H-1,2,4-triazol-5(4H)-one hydrochloride;
4-cyclopropyl-3-(5-(1,3-dimethyl-1H-indazol-5-yl)-2-phenyl-1H-imidazol-4-yl)-1H-1,2,4-triazol-5(4H)-one hydrochloride;
4-cyclopropyl-3-(5-(1-methyl-1H-indazol-6-yl)-2-(pyridin-4-yl)-1H-imidazol-4-yl)-1H-1,2,4-triazol-5(4H)-one dihydrochloride;
4-cyclopropyl-3-(5-(1-methyl-1H-indazol-6-yl)-2-(pyridin-3-yl)-1H-imidazol-4-yl)-1H-1,2,4-triazol-5(4H)-one dihydrochloride;
4-cyclopropyl-3-(5-(1-methyl-1H-indazol-6-yl)-2-(1-methyl-1H-pyrazol-4-yl)-1H-imidazol-4-yl)-1H-1,2,4-triazol-5(4H)-one hydrochloride;
4-cyclopropyl-3-(5-(1-methyl-1H-indazol-6-yl)-2-(1H-pyrazol-4-yl)-1H-imidazol-4-yl)-1H-1,2,4-triazol-5(4H)-one hydrochloride;
4-cyclopropyl-1-methyl-3-(5-(1-methyl-1H-indazol-6-yl)-2-phenyl-1H-imidazol-4-yl)-1H-1,2,4-triazol-5(4H)-one hydrochloride; and
and stereoisomers, tautomers, and hydrates thereof.

44. A pharmaceutical composition comprising the compound of any one of embodiments 1-43, and a pharmaceutically acceptable carrier.

45. method for inhibition of BET protein function comprising administering a therapeutically effective amount of the compound of any one of embodiments 1-43 or a pharmaceutical composition according to embodiment 44.

46. A method of treating an autoimmune or inflammatory disorder associated with BET proteins comprising administering a therapeutically effective amount of the compound of any one of embodiments 1-43 or a pharmaceutical composition according to embodiment 44.

47. A method of treating an acute or chronic non-autoimmune inflammatory disorder characterized by disregulation of IL-6 and/or IL-17 comprising administering a therapeutically effective amount of the compound of any one of embodiments 1-43 or a pharmaceutical composition according to embodiment 44.

48. A method of treating a cancer associated with overexpression, translocation, amplification, or rearrangement of a myc family oncoprotein that is sensitive to BET inhibition comprising administering a therapeutically effective amount of the compound of any one of embodiments 1-43 or a pharmaceutical composition according to embodiment 44.

49. A method of treating a cancer associated with overexpression, translocation, amplification, or rearrangement of BET proteins comprising administering a therapeutically effective amount of the compound of any one of embodiments 1-43 or a pharmaceutical composition according to embodiment 44.

50. A method of treating a cancer that relies on pTEFb (Cdk9/cyclin T) and BET proteins to regulate oncogenes comprising administering a therapeutically effective amount of the compound of any one of embodiments 1-43 or a pharmaceutical composition according to embodiment 44.

51. A method of treating a cancer associated with upregulation of BET responsive genes CDK6, Bcl2, TYRO3, MYB, and hTERT comprising administering a therapeutically effective amount of the compound of any one of embodiments 1-43 or a pharmaceutical composition according to embodiment 44.

52. A method of treating a cancer associated with a gene regulated by a super enhancer comprising administering a therapeutically effective amount of the compound of any one of embodiments 1-43 or a pharmaceutical composition according to embodiment 44.

53. A method of treating a cancer that is sensitive to effects of BET inhibition comprising administering a therapeutically effective amount of the compound of any one of embodiments 1-43 or a pharmaceutical composition according to embodiment 44.

54. A method of treating a cancer that is resistant to treatment with immunotherapy, hormone-deprivation therapy, and/or chemotherapy comprising administering a therapeutically effective amount of the compound of any one of embodiments 1-43 or a pharmaceutical composition according to embodiment 44.

55. The method of any one of embodiments 45-54, wherein the compound of any one of embodiments 1-43 or a pharmaceutical composition according to embodiment 44 is combined with other therapies, chemotherapeutic agents or antiproliferative agents.

56. The method of embodiment 55, wherein the therapeutic agent is selected from ABT-737, Azacitidine (Vidaza), AZD1152 (Barasertib), AZD2281 (Olaparib), AZD6244 (Selumetinib), BEZ235, Bleomycin Sulfate, Bortezomib (Velcade), Busulfan (Myleran), Camptothecin, Cisplatin, Cyclophosphamide (Clafen), CYT387, Cytarabine (Ara-C), Dacarbazine, DAPT (GSI-IX), Decitabine, Dexamethasone, Doxorubicin (Adriamycin), Etoposide, Everolimus (RAD001), Flavopiridol (Alvocidib), Ganetespib (STA-9090), Gefitinib (Iressa), Idarubicin, Ifosfamide (Mitoxana), IFNa2a (Roferon A), Melphalan (Alkeran), Methazolastone (temozolomide), Metformin, Mitoxantrone (Novantrone), Paclitaxel, Phenformin, PKC412 (Midostaurin), PLX4032 (Vemurafenib), Pomalidomide (CC-4047), Prednisone (Deltasone), Rapamycin, Revlimid (Lenalidomide), Ruxolitinib (INCB018424), Sorafenib (Nexavar), SU11248 (Sunitinib), SU11274, Vinblastine, Vincristine (Oncovin), Vinorelbine (Navelbine), Vorinostat (SAHA), and WP1130 (Degrasyn).

57. A method of treating a benign proliferative or fibrotic disorder, selected from the group consisting of benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, juvenile polyposis syndrome, idiopathic pulmonary fibrosis, renal fibrosis, post-operative stricture, keloid formation, scleroderma, and cardiac fibrosis comprising administering a therapeutically effective amount of the compound of any one of embodiments 1-43 or a pharmaceutical composition according to embodiment 44.

58. A method of treating a disease or disorder that benefits from up-regulation or ApoAI transcription and protein expression comprising administering a therapeutically effective amount of the compound of any one of embodiments 1-43 or a pharmaceutical composition according to embodiment 44.

59. A method of treating a metabolic disease or disorder comprising administering a therapeutically effective amount of the compound of any one of embodiments 1-43 or a pharmaceutical composition according to embodiment 44.

60. A method of treating a cancer associated with a virus comprising administering a therapeutically effective amount of the compound of any one of embodiments 1-43 or a pharmaceutical composition according to embodiment 44.

61. A method for treating HIV infection comprising administering a therapeutically effective amount of the compound of any one of embodiments 1-43 or a pharmaceutical composition according to embodiment 44 alone or in combination with anti-retroviral therapeutic.

62. A method for treating a disease or disorder selected from Alzheimer's disease, Parkinson's disease, Huntington disease, bipolar disorder, schizophrenia, Rubinstein-Taybi syndrome, and epilepsy comprising administering a therapeutically effective amount of the compound of any one of embodiments 1-43 or a pharmaceutical composition according to embodiment 44.

63. A method of male contraception comprising administering a therapeutically effective amount of the compound of any one of embodiments 1-43 or a pharmaceutical composition according to embodiment 44.

64. The method of embodiment 46, wherein the autoimmune or inflammatory disorder is selected from Acute Disseminated Encephalomyelitis, Agammaglobulinemia, Allergic Disease, Ankylosing spondylitis, Anti-GBM/Anti-TBM nephritis, Anti-phospholipid syndrome, Autoimmune aplastic anemia, Autoimmune hepatitis, Autoimmune inner ear disease, Autoimmune myocarditis, Autoimmune pancreatitis, Autoimmune retinopathy, Autoimmune thrombocytopenic purpura, Behcet's Disease, Bullous pemphigoid, Castleman's Disease, Celiac Disease, Churg-Strauss syndrome, Crohn's Disease, Cogan's syndrome, Dry eye syndrome, Essential mixed cryoglobulinemia, Dermatomyositis, Devic's Disease, Encephalitis, Eosinophlic esophagitis, Eosinophilic fasciitis, Erythema nodosum, Giant cell arteritis, Glomerulonephritis, Goodpasture's syndrome, Granulomatosis with Polyangiitis (Wegener's), Graves' Disease, Guillain-Barre syndrome, Hashimoto's thyroiditis, Hemolytic anemia, Henoch-Schonlein purpura, idiopathic pulmonary fibrosis, IgA nephropathy, Inclusion body myositis, Type I diabetes, Interstitial cystitis, Kawasaki's Disease, Leukocytoclastic vasculitis, Lichen planus, Lupus (SLE), Microscopic polyangitis, Multiple sclerosis, Myasthenia gravis, myositis, Optic neuritis, Pemphigus, POEMS syndrome, Polyarteritis nodosa, Primary biliary cirrhosis, Psoriasis, Psoriatic arthritis, Pyoderma gangrenosum, Relapsing polychondritis, Rheumatoid arthritis, Sarcoidosis, Scleroderma, Sjogren's syndrome, Takayasu's arteritis, Transverse myelitis, Ulcerative colitis, Uveitis, and Vitiligo.

65. The method of embodiment 47, wherein the acute or chronic non-autoimmune inflammatory disorder is selected from sinusitis, pneumonitis, osteomyelitis, gastritis, enteritis, gingivitis, appendicitis, irritable bowel syndrome, tissue graft rejection, chronic obstructive pulmonary disease (COPD), septic shock, osteoarthritis, acute gout, acute lung injury, acute renal failure, burns, Herxheimer reaction, and SIRS associated with viral infections.

66. The method of embodiment 47, wherein the acute or chronic non-autoimmune inflammatory disorder is selected from rheumatoid arthritis (RA) and multiple sclerosis (MS).

67. The method of embodiment 48, wherein the cancer is selected from B-acute lymphocytic leukemia, Burkitt's lymphoma, Diffuse large cell lymphoma, Multiple myeloma, Primary plasma cell leukemia, Atypical carcinoid lung cancer, Bladder cancer, Breast cancer, Cervix cancer, Colon cancer, Gastric cancer, Glioblastoma, Hepatocellular carcinoma, Large cell neuroendocrine carcinoma, Medulloblastoma, Melanoma, nodular, Melanoma, superficial spreading, Neuroblastoma, esophageal squamous cell carcinoma, Osteosarcoma, Ovarian cancer, Prostate cancer, Renal clear cell carcinoma, Retinoblastoma, Rhabdomyosarcoma, and Small cell lung carcinoma.

68. The method of embodiment 49, wherein the cancer is selected from NUT midline carcinoma, B-cell lymphoma, non-small cell lung cancer, esophageal cancer, head and neck squamous cell carcinoma, breast cancer, prostate cancer, and colon cancer.

69. The method of embodiment 50, wherein the cancer is selected from chronic lymphocytic leukemia and multiple myeloma, follicular lymphoma, diffuse large B cell lymphoma with germinal center phenotype, Burkitt's lymphoma, Hodgkin's lymphoma, follicular lymphomas and activated, anaplastic large cell lymphoma, neuroblastoma and primary neuroectodermal tumor, rhabdomyosarcoma, prostate cancer, and breast cancer.

70. The method of embodiment 51, wherein the cancer is selected from pancreatic cancer, breast cancer, colon cancer, glioblastoma, adenoid cystic carcinoma, T-cell prolymphocytic leukemia, malignant glioma, bladder cancer, medulloblastoma, thyroid cancer, melanoma, multiple myeloma, Barret's adenocarcinoma, hepatoma, prostate cancer, pro-myelocytic leukemia, chronic lymphocytic leukemia, mantle cell lymphoma, diffuse large B-cell lymphoma, small cell lung cancer, and renal carcinoma.

71. The method of embodiment 52, wherein the gene is the MYC oncogene.

72. The method of embodiment 53, wherein the cancer is selected from NUT-midline carcinoma (NMV), acute myeloid leukemia (AML), acute B lymphoblastic leukemia (B-ALL), Burkitt's Lymphoma, B-cell Lymphoma, Melanoma, mixed lineage leukemia, multiple myeloma, pro-myelocytic leukemia (PML), non-Hodgkin's lymphoma, Neuroblastoma, Medulloblastoma, lung carcinoma (NSCLC, SCLC), breast cancer, prostate cancer, and colon carcinoma.

73. The method of embodiment 53, wherein the cancer is selected from adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute myeloid leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell acute lymphoblastic leukemia, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, Leydig cell tumor, liposarcoma, lung cancer, lymphangioma, lymphangiosarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, Merkel cell cancer, mesothelioma, metastatic urothelial carcinoma, mixed Mullerian tumor, mixed lineage leukemia, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, NUT-midline carcinoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.
74. The method of embodiment 58, wherein the disease is cardiovascular disease, dyslipidemia, atheroschlerosis, hypercholesterolemia, metabolic syndrome, and Alzheimer's disease.
75. The method of embodiment 59, wherein the metabolic disorder is selected from obesity-associated inflammation, type II diabetes, and insulin resistance.
76. The method of embodiment 60, wherein the virus is selected from Epstein-Barr Virus (EBV), hepatitis B virus (HBV), hepatitis C virus (HCV), Kaposi's sarcoma associated virus (KSHV), human papilloma virus (HPV), Merkel cell polyomavirus, and human cytomegalovirus (CMV).

EXAMPLES

General Methods.

Unless otherwise noted, reagents and solvents were used as received from commercial suppliers. Proton nuclear magnetic resonance spectra were obtained on a Bruker 400 MHz spectrometer. Spectra are given in ppm (δ) and coupling constants, J values, are reported in hertz (Hz). Mass spectra analyses were performed on Shimadzu 2020 Mass Spectrometer in ESI or APCI mode when appropriate.

Abbreviations

DCM: dichloromethane; DMF: dimethylformamide; EtOAc: ethyl acetate; NBS: N-bromosuccinimide; MeOH: methanol; PE: petroleum ether; SEM-Cl: (2-(chloromethoxy)ethyl)trimethylsilane; TEA: triethylamine; TFA: trifluoroacetic acid; THF: tetrahydrofuran; TLC: thin layer chromatography.

General Procedure A

Example 1: Preparation of 3-(5-(3-Acetylphenyl)-2-phenyl-1H-imidazol-4-yl)-4-cyclopropyl-1H-1,2,4-triazol-5(4H)-one

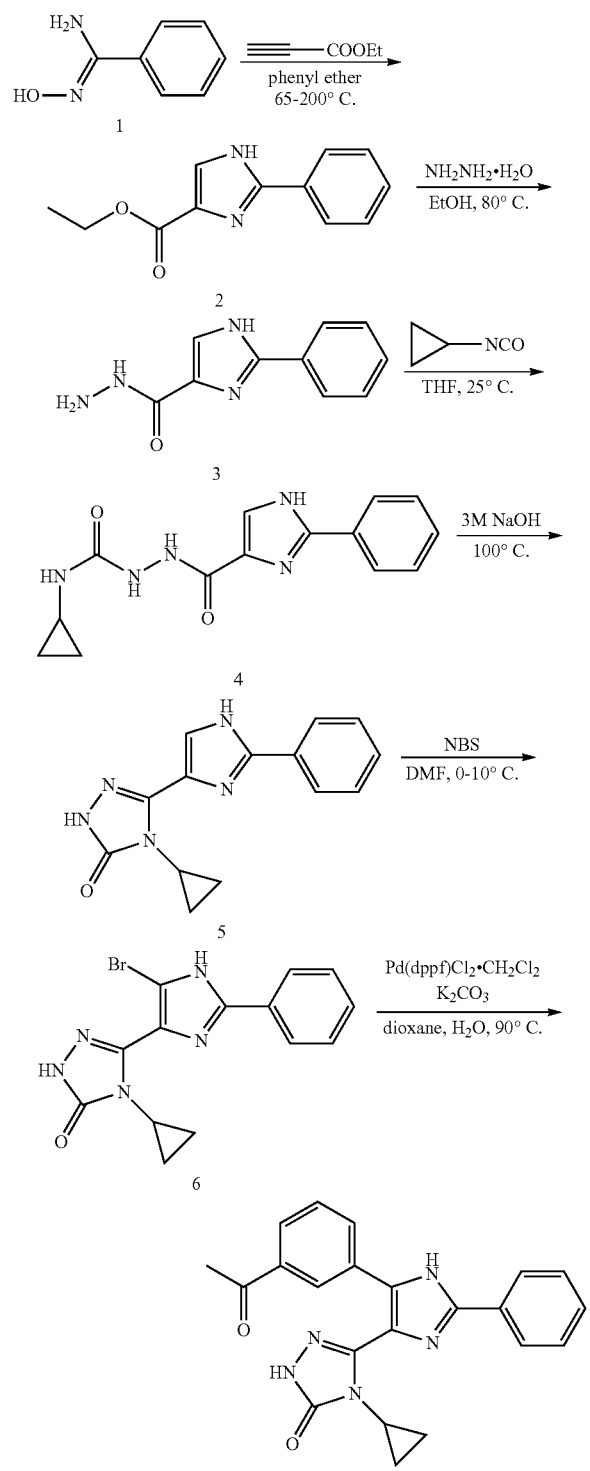

Example 1

A solution of compound 1 (25.0 g, 184 mmol, 1.00 eq), ethyl prop-2-ynoate (18.0 g, 184 mmol, 1.0 eq) in MeOH (200 mL) was heated at 65° C. for 16 h. After cooling to 25° C., MeOH was removed under reduced pressure and the residue was purified by column chromatography (PE:EtOAc=3:1) to give an oil. The oil was dissolved in phenyl ether (200 mL) and heated at 200° C. for 30 min. TLC indicated conversion to a new spot. The reaction mixture was cooled to 25° C. and poured into petroleum ether (500 mL), extracted with 1N HCl (2×200 mL). The combined aqueous layers were carefully diluted with sodium bicarbonate to basic pH and extracted with ethyl acetate (5×200 mL). The combined organic layers were dried and concentrated. The residue was purified by column chromatography (3:1 PE:EtOAc) and washed with DCM (200 mL) to afford 2 (18.0 g, 83.2 mmol, 45% yield) as a yellow solid: $^1$H NMR (400 MHz, CDCl$_3$) δ 1.30 (t, J=7.03 Hz, 3H), 4.26 (q, J=6.94 Hz, 2H), 7.36-7.54 (m, 3H), 7.92-8.02 (m, 2H), 8.13 (br s, 1H).

To a solution of compound 2 (18.0 g, 83.2 mmol, 1.0 eq) in EtOH (200 mL) was added hydrazine monohydrate (16.7 g, 333 mmol, 4.0 eq) in one portion at 25° C. The mixture was stirred at 80° C. for 16 h. TLC showed the reaction was completed. The mixture was cooled to 25° C. and concentrated under reduced pressure at 40° C. The residue was purified by silica gel chromatography (1:10 MeOH/EtOAc) to afford 3 (14.0 g, 69.2 mmol, 83% yield) as a yellow solid: $^1$H NMR (400 MHz, DMSO-d6) δ 7.35-7.42 (m, 1H), 7.43-7.51 (m, 2H), 7.73 (s, 1H), 7.99-8.06 (m, 1H), 8.97 (br s, 1H).

To a solution of compound 3 (14.0 g, 69.2 mmol, 1.0 eq) in THF (120 mL) was added a solution of isocyanatocyclopropane (28.8 g, 346 mmol, 5.0 eq) in DCM (500 mL) dropwise at 25° C. The mixture was stirred at 25° C. for 2 h. The resulting yellow precipitate was filtered and washed with EtOAc (200 mL) to afford 4 (14.0 g, 49.1 mmol, 70% yield): ESI m/z 286.1[M+1]+.

To a solution of compound 4 (14 g, 49.07 mmol, 1.0 eq) in H$_2$O (300 mL) was added NaOH (5.89 g, 147.21 mmol, 3.0 eq) in one portion at 25° C. Then the reaction mixture was heated at 100° C. After 40 h, TLC showed the reaction was completed and the mixture was cooled to 25° C. 3N HCl was added and at pH 5-6, a crystalline solid formed. The solid was isolated by filtration, washed with water (30 mL) and dried at 50° C. to afford 5 (8 g, 29.93 mmol, 61% yield): $^1$H NMR (400 MHz, DMSO-d6) δ 0.80-0.90 (m, 2H), 0.93-1.04 (m, 2H), 3.13 (dt, J=6.90, 3.33 Hz, 1H), 7.42-7.61 (m, 2H), 7.91 (s, 1H), 8.10 (d, J=7.40 Hz, 2H).

To a solution of compound 5 (8.00 g, 29.9 mmol, 1.0 eq) in DMF (60 mL) was added NBS (6.39 g, 35.9 mmol, 1.2 eq) in portions at 0° C. under N$_2$ atmosphere. The resulting mixture was stirred at 0-10° C. for 30 min. TLC showed the reaction was complete. The reaction mixture was quenched with water (50 mL) and the aqueous phase was extracted with ethyl acetate (6×100 mL). The combined organic layers were washed with sat. sodium thiosulfate (100 mL), dried with anhydrous Na$_2$SO$_4$, filtered and concentrated in vacuo. The residue was purified by silica gel chromatography (PE/EtOAc, 50-100%) to afford 6 (5.50 g, 15.9 mmol, 53% yield) as a yellow solid: $^1$H NMR (400 MHz, DMSO-d6) δ 0.62 (br s, 2H), 0.78-0.87 (m, 2H), 2.97 (br s, 1H), 7.43-7.57 (m, 3H), 7.97 (d, J=7.15 Hz, 2H).

Compound 6 (50 mg, 0.14 mmol, 1.0 eq), (3-acetylphenyl)boronic acid (45.9 mg, 0.280 mmol, 2.0 eq), K$_2$CO$_3$ (40 mg, 0.28 mmol, 2.0 eq) and Pd(dppf)Cl$_2$.CH$_2$Cl$_2$ (24 mg, 0.03 mmol, 0.20 eq) in dioxane (2 mL) and H$_2$O (0.5 mL) was degassed with nitrogen and then heated at 90° C. for 3 h under nitrogen atmosphere. LCMS showed the starting material was consumed completely. The reaction mixture was cooled to 25° C. and the solvent was removed in vacuo. The residue was dissolved in MeOH (10 mL) and filtered. The resulting filtrate was concentrated and purified by prep-HPLC (HCl buffer) to afford 3-(5-(3-acetylphenyl)-2-phenyl-1H-imidazol-4-yl)-4-cyclopropyl-1H-1,2,4-triazol-5 (4H)-one hydrochloride (Example 1) (12 mg, 31.1 umol, 22% yield) as a white solid: $^1$H NMR (400 MHz, CD$_3$OD) δ 0.63-0.83 (m, 4H), 2.47 (dt, J=7.15, 3.33 Hz, 1H), 2.67 (s, 3H), 7.60-7.74 (m, 4H), 7.87-7.97 (m, 1H), 8.03-8.17 (m, 3H), 8.37 (t, J=1.57 Hz, 1H); ESI m/z 386.2[M+1]+.

General Procedure B

Example 17: 4-(Cyclopropylmethyl)-3-(5-(1-methyl-1H-indazol-6-yl)-2-phenyl-1H-imidazol-4-yl)-1H-1,2,4-triazol-5(4H)-one)

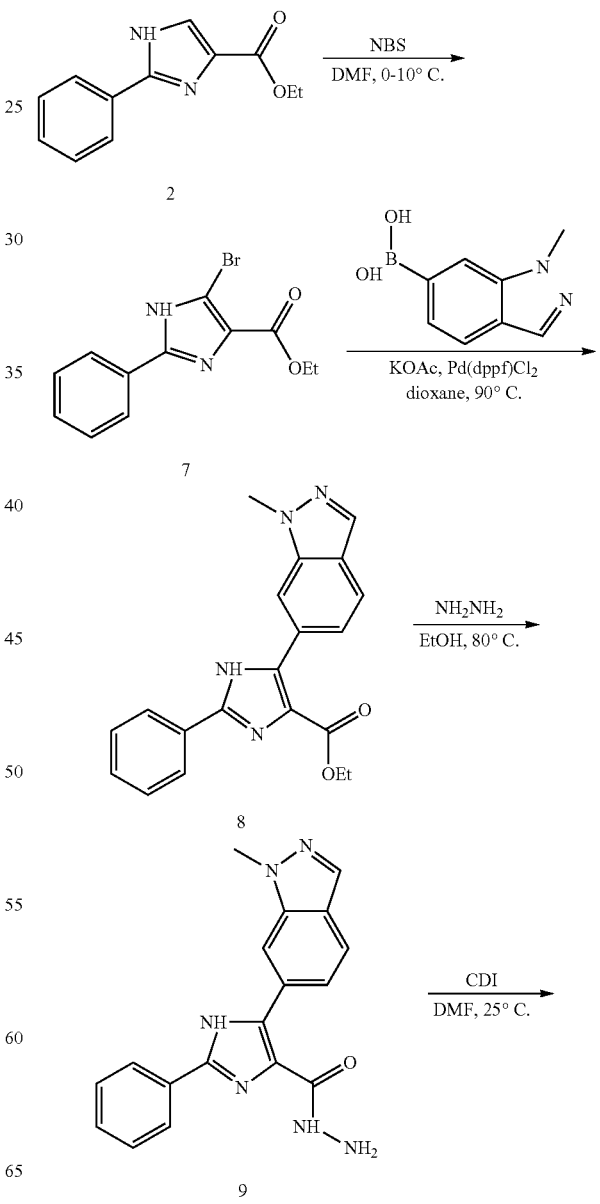

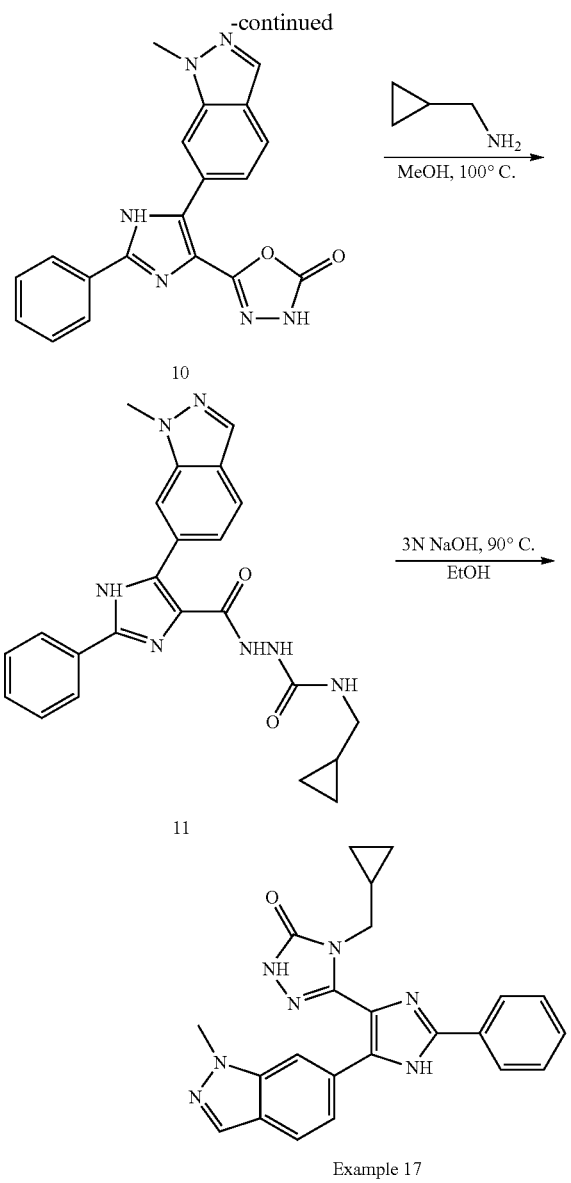

Example 17

To a solution of compound 2 (2.00 g, 9.25 mmol, 1.00 eq) in DMF (20 mL), was added NBS (1.98 g, 11.10 mmol, 1.20 eq) in portions at 0° C. under nitrogen. The mixture was stirred at 0-10° C. for 30 min. The mixture was diluted with water and the aqueous phase was extracted with EtOAc (3×80 mL). The combined organic fractions were washed with a solution of saturated sodium thiosulfate (30 mL), dried with anhydrous sodium sulfate and concentrated under vacuum to afford 7 (1.83 g, 6.20 mmol, 67% yield) as a yellow solid: $^1$H NMR (400 MHz, DMSO-d6) δ 1.34 (t, J=7.16 Hz, 3H) 4.33 (q, J=6.97 Hz, 2H) 7.49 (d, J=6.41 Hz, 3H) 8.09 (d, J=6.40 Hz, 2H) 13.51-13.85 (m, 1H).

To a mixture of compound 7 (800 mg, 2.71 mmol, 1.00 eq) and (1-methylindazol-6-yl)boronic acid (477 mg, 2.71 mmol, 1.00 eq) in dioxane (10 mL) was added KOAc (266.03 mg, 2.71 mmol, 1.00 eq) and Pd(dppf)Cl$_2$ (198 mg, 271 umol, 0.10 eq) in one portion at 25° C. under nitrogen. Then the mixture was heated to 90° C. and stirred for 16 hr. The mixture was concentrated under reduced pressure and the residue was filtered through silica gel (0-100% EtOAc in PE). The crude product was purified by preparative HPLC to afford 8 (480 mg, 1.39 mmol, 51% yield) as a yellow solid: ESI m/z 347.1[M+1].

To a mixture of compound 8 (450 mg, 1.30 mmol, 1.00 eq) in EtOH (5 mL) was added hydrazine hydrate (976 mg, 19.5 mmol, 15.0 eq) in one portion at 25° C. under nitrogen. Then the reaction mixture was stirred at 80° C. for 30 hours. The mixture was concentrated and the residue was taken up in EtOAc (10 mL). The suspension was stirred for 10 min and filtered to afford 9 (300 mg, 902 umol, 69% yield) as a gray solid: $^1$H NMR (400 MHz, DMSO-d6) δ 4.09 (s, 3H) 4.51 (br. s., 2H) 7.42-7.55 (m, 3H) 7.64 (d, J=8.67 Hz, 1H) 7.76-7.84 (m, 1H) 8.07-8.23 (m, 4H) 9.15 (br. s., 1H) 12.94 (br. s., 1H).

To a mixture of compound 9 (50 mg, 150 umol, 1.00 eq) in DMF (1.0 mL) was added carbonyldiimidazole (29 mg, 180 umol, 1.2 eq) in one portion at 25° C. under nitrogen. The reaction mixture was stirred at 25° C. for 16 hr and was concentrated in vacuum. The residue was taken up in water (5 mL) and stirred for 15 min. The precipitate was filtered and dried under vacuum to afford 10 (35 mg, 97 umol, 64% yield) as a gray solid: $^1$H NMR (400 MHz, DMSO-d6) δ 4.10 (s, 3H) 7.03 (s, 2H) 7.42-7.57 (m, 4H) 7.86 (br. s., 1H) 8.11 (d, J=13.43 Hz, 4H) 13.08-13.36 (m, 1H).

Compound 10 (35 mg, 97 umol, 1.00 eq) and cyclopropylmethanamine (69 mg, 976 umol, 10.0 eq) were taken up in MeOH (2.0 mL) in a microwave tube. The sealed tube was irradiated in the microwave at 90° C. for 1.5 hr. The reaction mixture was concentrated under vacuum to afford 11 (30 mg, 70 umol, 72% yield) as yellow solid: ESI m/z 430.2 [M+1]+.

To a mixture of compound 11 (20 mg, 47 umol, 1.0 eq) in EtOH (1.0 mL) was added NaOH (3M, 16 uL, 1.0 eq) in one portion at 25° C. under nitrogen. The reaction mixture was stirred at 90° C. for 16 hr. 3N HCl was added to lower the pH to 5-6 which caused a precipitate to form. The solid was isolated by filtration and taken up in DMF (5 mL) for purification by preparative HPLC. 4-(Cyclopropylmethyl)-3-(5-(1-methyl-1H-indazol-6-yl)-2-phenyl-1H-imidazol-4-yl)-1H-1,2,4-triazol-5(4H)-one (Example 17) (13 mg, 32 umol, 68% yield) was isolated as a white solid: $^1$H NMR (400 MHz, DMSO-d$_6$) δ 0.08-0.41 (m, 4H) 3.67 (br. s., 2H) 4.08 (s, 3H) 7.33-7.49 (m, 2H) 7.51-7.57 (m, 2H) 7.80 (d, J=8.41 Hz, 1H) 8.03-8.09 (m, 2H) 8.10-8.14 (m, 2H) 11.79 (br. s., 1H); ESI m/z 412.1[M+1]+.

General Procedure C

Example 23: 4-Cyclopropyl-3-(5-(1-methyl-1H-indazol-6-yl)-2-(pyridin-4-yl)-1H-imidazol-4-yl)-1H-1,2,4-triazol-5(4H)-one

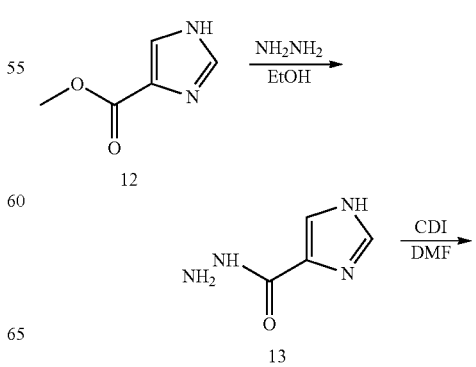

-continued

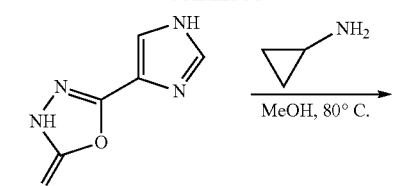
14

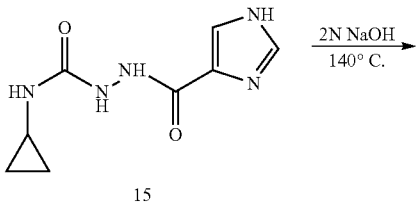
15

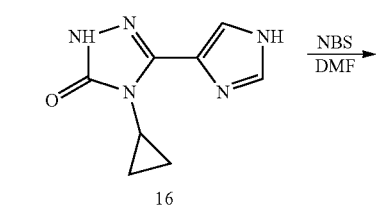
16

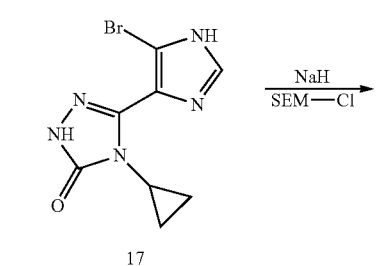
17

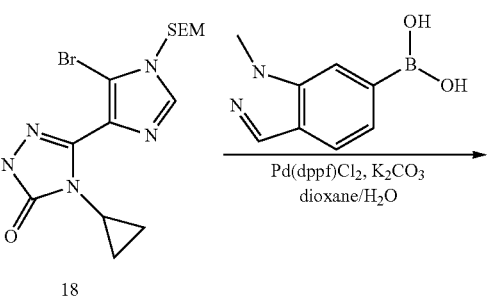
18

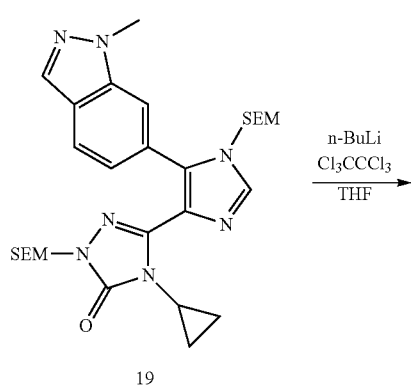
19

-continued

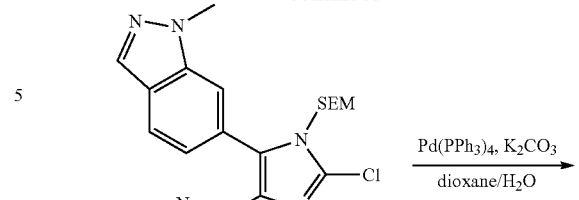
20

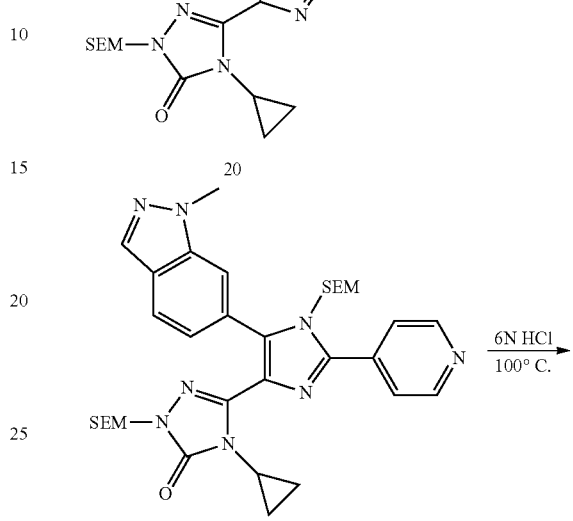
21

Example 23

A solution of compound 12 (18.0 g, 142.7 mmol, 1.0 eq) and hydrazine hydrate (35.7 g, 713.7 mmol, 5.0 eq) in EtOH (200 mL) was stirred at 90° C. for 15 h. After cooling to room temperature, a precipitate formed. The solid was filtered, and dried under vacuum to afford compound 13 (15.0 g, 119 mmol, 83% yield) as a white crystalline solid: $^1$H NMR (400 MHz, DMSO-$d_6$) δ 4.35 (br. s., 2H) 7.61 (s, 1H) 7.72 (d, J=0.88 Hz, 1H) 9.10 (br. s., 1H) 12.49 (br. s., 1H).

Carbonyldiimidazole (17.7 g, 109.4 mmol, 1.2 eq) was added to a suspension of compound 13 (11.5 g, 91.2 mmol, 1.0 eq) in DMF (110 mL) at 0° C. Initially, the solution cleared, but after stirring at 15° C. for 3 hr, a precipitate formed. The solid was filtered, washed with DCM (100 mL) and dried under vacuum to afford compound 14 (10.4 g, 67.7 mmol, 74% yield) as an off-white solid: ESI m/z 153.0[M+1]$^+$.

A clear solution of compound 14 (5.00 g, 32.87 mmol, 1.00 eq) and cyclopropanamine (9.38 g, 164.4 mmol, 5.0 eq) in MeOH (5.00 mL) was stirred under microwave irradiation at 80° C. for 2 hr. After cooling, a precipitate formed. The reaction mixture was concentrated and the residue was triturated in ethyl acetate (40 mL). The solid was filtered and dried under vacuum to afford compound 15 (4.50 g, 21.5 mmol, 65% yield) as a light-yellow solid: $^1$H NMR (400 MHz, DMSO-$d_6$) δ 0.34-0.42 (m, 2H) 0.52-0.61 (m, 2H) 2.42-2.49 (m, 1H) 6.49 (br. s., 1H) 7.71 (s, 1H) 7.75 (s, 2H) 9.34 (br. s., 1H) 12.53 (br. s., 1H).

A clear solution of compound 15 (4.70 g, 22.5 mmol, 1.0 eq) in 2N NaOH (13 mL) was stirred under microwave irradiation at 140° C. for 4 hr. The reaction mixture was cooled to 0° C., and conc. HCl was added to adjust the pH to 8. The precipitate was filtered, washed with water (100 mL) and dried under vacuum to afford compound 16 (2.90 g, 14.6 mmol, 65.1% yield, 96.4% purity) as a white solid: $^1$H NMR (400 MHz, DMSO-$d_6$) δ 0.75-0.90 (m, 4H) 3.01-3.09 (m, 1H) 7.64 (s, 1H) 7.80 (s, 1H) 11.52 (s, 1H) 12.50 (br. s., 1H); ESI m/z 192.1 [M+1]$^+$.

N-Bromosuccinimide (5.36 g, 30.1 mmol, 1.2 eq) was added in portions to a 0° C. solution of compound 16 (4.80 g, 25.1 mmol, 1.0 eq) in DMF (40 mL) over 1 hr. The reaction mixture was stirred at 0° C. for 3 h. The reaction mixture was purified by p-HPLC directly to afford compound 17 (4.60 g, 12.0 mmol, 48% yield) as a white crystalline TFA salt: $^1$H NMR (400 MHz, DMSO-$d_6$) δ 0.51-0.61 (m, 2H) 0.73-0.83 (m, 2H) 2.85-2.95 (m, 1H) 7.94 (s, 1H) 11.97 (s, 1H); ESI m/z 270.0, 272.0 [M+1]$^+$.

A solution of compound 17 (4.50 g, 11.7 mmol, 1.0 eq) in DMF (2 mL) was added dropwise to another solution of SEM-Cl (5.86 g, 35.2 mmol, 3.0 eq) in THF (50 mL) at 0° C. Then the solution was stirred at 10° C. for 1 hr at which time a precipitate formed. Sodium hydride (1.88 g, 46.9 mmol, 4.0 eq) was added to the mixture in portions. Initially, the reaction mixture turn red, but the color faded as it was stirred for 15 hr. The reaction was quenched by the dropwise addition of water (10 mL) at 0° C. Additional water (100 mL) was added and the the pH was adjusted to 7 with aq. HCl. The reaction mixture was extracted with ethyl acetate (2×100 mL). The combined organic fractions were washed with brine, dried over anhydrous sodium sulfate and concentrated. The residue was purified by column chromatography (10-50% EA in PE) to afford compound 18 (2.90 g, 5.47 mmol, 46.7% yield) as a colorless oil: $^1$H NMR (400 MHz, CDCl$_3$) δ 0.00 (s, 9H) 0.02 (s, 9H) 0.63-0.78 (m, 2H) 0.78-0.94 (m, 4H) 0.94-1.02 (m, 2H) 3.03-3.11 (m, 1H) 3.39-3.48 (m, 2H) 3.63-3.74 (m, 2H) 5.21 (s, 2H) 5.33 (br. s., 2H) 7.68 (s, 1H); ESI m/z 532.1, 530.1 [M+1]$^+$.

Compound 18 (1.50 g, 2.83 mmol, 1.0 eq), (1-methylindazol-6-yl)boronic acid (697 mg, 3.96 mmol, 1.40 eq), K$_2$CO$_3$ (782 mg, 5.66 mmol, 2.0 eq) and Pd(dppf)Cl$_2$ (207 mg, 283 umol, 0.10 eq) were combined in a mixed solvent of dioxane (20 mL) and water (5 mL). The reaction mixture was degassed with nitrogen and then heated at 90° C. for 15 hr under nitrogen atmosphere. The reaction mixture was concentrated under reduced pressure and the residue was purified by column chromatography (0-100% EA in DCM) to afford compound 19 (1.46 g, 80% purity) as a brown oil: ESI m/z 582.3 [M+1]$^+$.

n-BuLi (2.5 M, 1.81 mL, 1.80 eq) was added to a solution of compound 19 (1.46 g, 2.51 mmol, 1.00 eq) in THF (33 mL) at −78° C. under a nitrogen atmosphere. The resulting slurry was stirred at −78° C. for 5 min, then a solution of 1,1,1,2,2,2-hexachloroethane (832 mg, 3.51 mmol, 1.40 eq) in THF (3 mL) was added in portions. The reaction mixture was stirred for 30 min at −78° C. as the color turned from brown to red. The reaction was quenched by the addition of water (40 mL) at 0° C. and the reaction mixture was extracted with ethyl acetate (2×100 mL). The combined organic fractions were washed with brine (50 mL), concentrated and the residue was purified by column chromatography (20%-100% EA in PE) to afford compound 20 (1.05 g, 85% purity) as a red gum: ESI m/z 616.2 [M+1]$^+$.

Compound 20 (100 mg, 162 umol, 1.0 eq), 4-pyridylboronic acid (40 mg, 325 umol, 2.0 eq), K$_2$CO$_3$ (45 mg, 325 umol, 2.0 eq) were combined in a mixed solvent of dioxane (3 mL) and water (600 uL). Pd(PPh$_3$)$_4$(19 mg, 16 umol, 0.10 eq) was added under nitrogen atmosphere, and then the mixture was stirred at 95° C. for 15 h. The reaction mixture was concentrated under reduced pressure and the residue was purified by column chromatography (0-10% MeOH in DCM) to afford compound 21 (80 mg) as a yellow oil: ESI m/z 659.2 [M+1]+.

A solution of compound 21 (80 mg) in 6M hydrochloric acid (10 mL) was heated to 100° C. for 3 hr. The reaction mixture was concentrated and the residue was triturated in methanol (2 mL). The solid was isolated by filtration to give 4-cyclopropyl-3-(5-(1-methyl-1H-indazol-6-yl)-2-(pyridin-4-yl)-1H-imidazol-4-yl)-1H-1,2,4-triazol-5(4H)-one dihydrochloride (Example 23) (23 mg, 58 umol, 48% yield) as a yellow solid: $^1$H NMR (300 MHz, DMSO-$d_6$) δ 0.59-0.74 (m, 4H) 4.09 (s, 3H) 7.34 (d, J=8.67 Hz, 1H) 7.44-7.68 (m, 1H) 7.84 (d, J=8.48 Hz, 1H) 8.04-8.21 (m, 2H) 8.54 (d, J=5.46 Hz, 2H) 8.94 (d, J=6.40 Hz, 2H) 11.94 (br. s., 1H); ESI m/z 399.1 [M+1]+.

General Procedure D

Example 27: 4-Cyclopropyl-2-methyl-5-[4-(1-methylindazol-6-yl)-2-phenyl-1H-imidazol-5-yl]-1,2,4-triazol-3-one

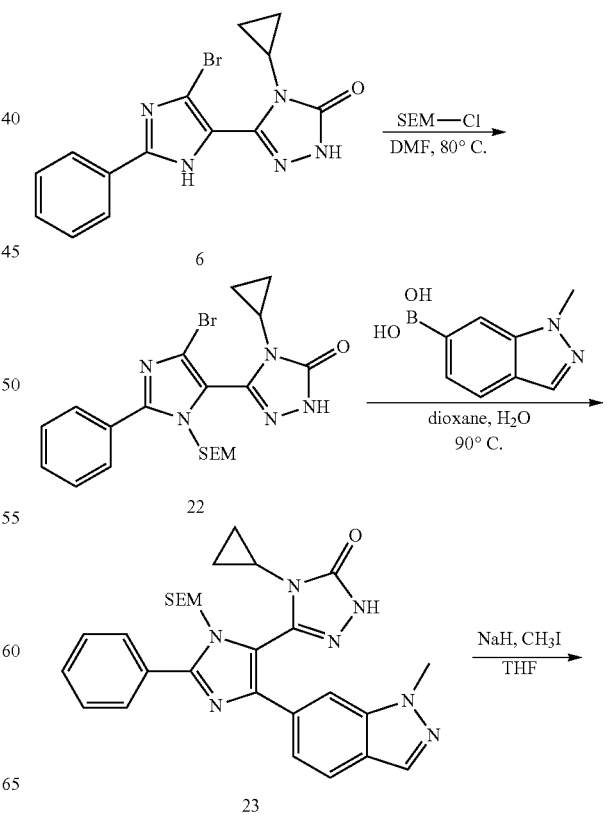

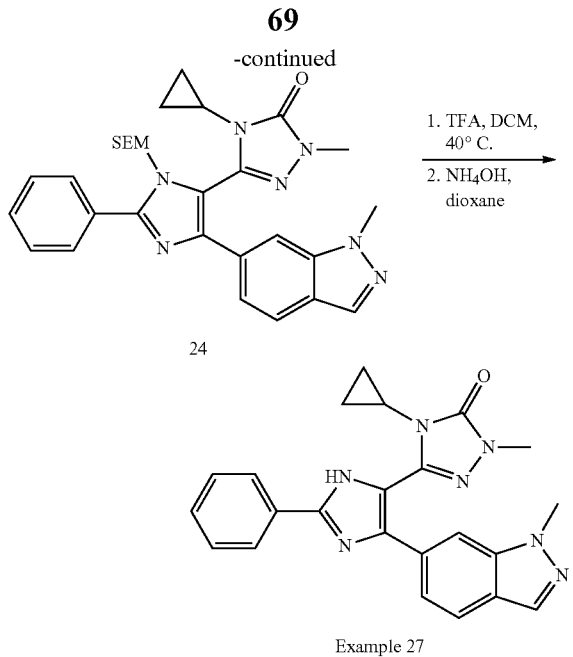

SEM-Cl (188 mg, 1.13 mmol, 1.95 eq) was added to a solution of compound 6 (200 mg, 578 umol, 1.0 eq) and TEA (146 mg, 1.44 mmol, 2.5 eq) in DMF (6 mL). The reaction mixture was purged with nitrogen and heated at 80° C. for 2 h. The yellow mixture was cooled to 25° C. and concentrated under reduced pressure. The residue was purified by silica gel chromatography (20-50% EA in PE) to afford 22 (161 mg) as yellow solid: ESI m/z 477.9[M+1]$^+$.

Compound 22 (50 mg, 105 umol, 1.0 eq) and (1-methyl-indazol-6-yl)boronic acid (26.04 mg, 147.98 umol, 1.41 eq) were combined in 1,4-dioxane (2 mL) and water (400 uL). $K_2CO_3$ (30 mg, 217 umol, 2.1 eq) and $Pd(PPh_3)_4$ (18 mg, 16 umol, 0.15 eq) were added and the mixture was purged with nitrogen. The reaction mixture was heated at 90° C. for 20 h. The residue was purified by prep-TLC (5% MeOH in DCM) to afford 23 (38 mg, 67 umol, 64% yield) as yellow solid: ESI m/z 528.2[M+1]$^+$.

Sodium hydride (4 mg, 100 umol, 1.5 eq) was added to a solution of compound 23 (38 mg, 67 umol, 1.0 eq) in THF (3 mL) at −10° C. and the reaction was stirred for 1 hr at −10° C. Iodomethane (610 mg, 4.30 mmol, 64.1 eq) was added dropwise and the reaction mixture was purged with nitrogen. After stirring for 16 hr at 15° C., the mixture was cooled to 0° C. and quenched with ice-water (15 mL). The reaction mixture was stirred for another 0.5 h and was extracted with DCM (2×10 mL). The combined organic fractions were washed with brine (2×10 mL), dried with anhydrous sodium sulfate, filtered and concentrated under vacuum. The residue was purified by prep-TLC (10% MeOH in DCM) to afford 24 (36 mg) as yellow solid: ESI m/z 542.2[M+1]$^+$.

To a solution of compound 24 (20 mg, 37 umol, 1.0 eq) in DCM (10 mL) was added TFA (3 mL) at 14° C. The reaction mixture was heated at 40° C. for 1 hr and concentrated under reduced pressure. The residue was taken up in dioxane (3 mL), then ammonium hydroxide (1.29 mg, 36.9 umol, 1.0 eq) was added dropwise. The mixture was stirred at 14° C. for 0.5 h and was concentrated under reduced pressure. The residue was purified by preparative HPLC to afford 4-cyclopropyl-1-methyl-3-(5-(1-methyl-1H-indazol-6-yl)-2-phenyl-1H-imidazol-4-yl)-1H-1,2,4-triazol-5(4H)-one hydrochloride (Example 27) (3 mg, 7.3 umol, 20% yield) as light yellow solid: $^1$H-NMR (DMSO-$d_6$, 300 MHz): δ 8.17 (d, J=7.3 Hz, 2H), 8.09 (d, J=9.2 Hz, 2H), 7.77-7.85 (m, 1H), 7.44-7.62 (m, 3H), 7.27-7.34 (m, 1H), 4.08 (s, 3H), 3.39 (s, 3H), 1.12-1.27 (m, 1H), 0.63 ppm (d, J=4.5 Hz, 4H); ESI m/z 412.0 [M+1]$^+$.

TABLE 2

Example Compounds

| Example | Chemical Name | Structure | General Procedure | Characterization | Yield |
|---|---|---|---|---|---|
| 1 | 3-(5-(3-acetylphenyl)-2-phenyl-1H-imidazol-4-yl)-4-cyclopropyl-1H-1,2,4-triazol-5(4H)-one hydrochloride | 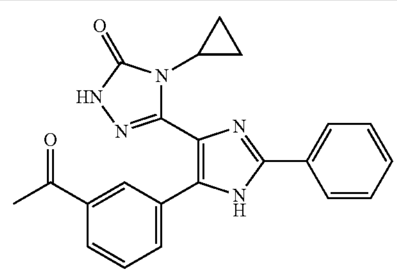 [SMILES: CC(=O)c1cccc(-c2[nH]c(-c3ccccc3)nc2-c2n[nH]c(=O)n2C2CC2)c1] | A | $^1$H NMR (400 MHz, $CD_3OD$) δ 0.63-0.83 (m, 4H), 2.47 (dt, J = 7.15, 3.33 Hz, 1H), 2.67 (s, 3H), 7.60-7.74 (m, 4H), 7.87-7.97 (m, 1H), 8.03-8.17 (m, 3H), 8.37 (t, J = 1.57 Hz, 1H); ESI m/z 386.2 [M + 1]$^+$. | 22% |
| 2 | methyl 3-(4-(4-cyclopropyl-5-oxo-4,5-dihydro-1H-1,2,4-triazol-3-yl)-2-phenyl-1H-imidazol-5-yl)-4-methyl benzoate hydrochloride | 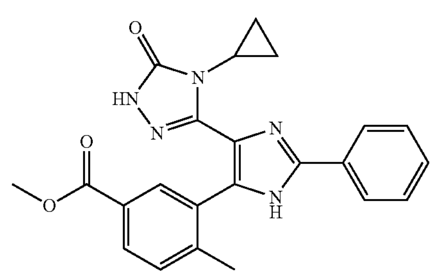 [SMILES: COC(=O)c1ccc(C)c(-c2[nH]c(-c3ccccc3)nc2-c2n[nH]c(=O)n2C2CC2)c1] | A | $^1$H NMR (400 MHz, $CD_3OD$) δ 0.72-0.79 (m, 2H), 0.80-0.87 (m, 2H), 2.20-2.29 (m, 1H), 2.41 (s, 3H), 3.93 (s, 3H), 7.57 (d, J = 8.03 Hz, 1H), 7.65-7.74 (m, 3H), 8.06 (dd, J = 7.53, 2.01 Hz, 2H), 8.10 (dd, J = 8.03, 1.76 Hz, 1H), 8.16 (d, J = 1.63 Hz, 1H); ESI m/z 416.1 [M + 1]$^+$. | 22% |

TABLE 2-continued

Example Compounds

| Example | Chemical Name | Structure | General Procedure | Characterization | Yield |
|---|---|---|---|---|---|
| 3 | 3-(4-(4-cyclopropyl-5-oxo-4,5-dihydro-1H-1,2,4-triazol-3-yl)-2-phenyl-1H-imidazol-5-yl)-N-methyl benzamide hydrochloride | 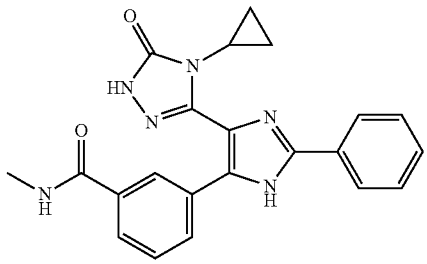 [SMILES: CNC(=O)c1cccc(-c2[nH]c(-c3ccccc3)nc2-c2n[nH]c(=O)n2C2CC2)c1] | A | $^1$H NMR (400 MHz, CD$_3$OD) δ 0.64-0.84 (m, 4H), 2.22-2.36 (m, H), 2.97 (s, 3H), 7.63-7.80 (m, 4H), 7.83-7.89 (m, 1H), 8.00 (d, J = 7.91 Hz, 1H), 8.10 (dd, J = 8.09, 1.44 Hz, 2H), 8.23 (t, J = 1.57 Hz, 1H); ESI m/z 401.1 [M + 1]$^+$. | 28% |
| 4 | 3-(4-(4-cyclopropyl-5-oxo-4,5-dihydro-1H-1,2,4-triazol-3-yl)-2-phenyl-1H-imidazol-5-yl) benzamide hydrochloride | 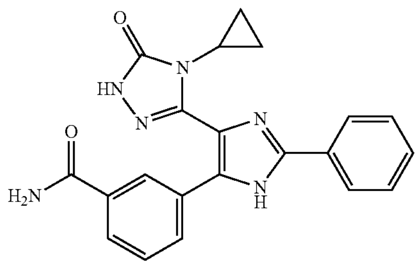 [SMILES: NC(=O)c1cccc(-c2[nH]c(-c3ccccc3)nc2-c2n[nH]c(=O)n2C2CC2)c1] | A | $^1$H NMR (400 MHz, CD$_3$OD) δ 0.65-0.82 (m, 4H), 2.24-2.36 (m, 1H), 3.33 (dt, J = 3.26, 1.63 Hz, 4H), 7.63-7.82 (m, 4H), 7.85-7.95 (m, 1H), 8.04-8.19 (m, 3H), 8.29 (t, J = 1.57 Hz, 1H); ESI m/z 387.1 [M + 1]$^+$. | 22% |
| 5 | 4-cyclopropyl-3-(5-(3-oxo-2,3-dihydro-1H-inden-5-yl)-2-phenyl-1H-imidazol-4-yl)-1H-1,2,4-triazol-5(4H)-one hydrochloride | 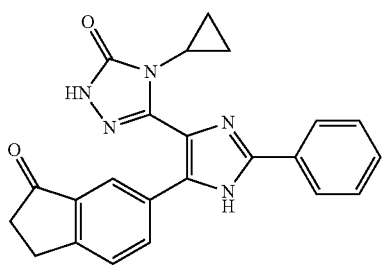 [SMILES: O=C1CCc2ccc(-c3[nH]c(-c4ccccc4)nc3-c3n[nH]c(=O)n3C3CC3)cc21] | A | $^1$H NMR (400 MHz, CD$_3$OD) δ 0.59-0.88 (m, 4H), 2.35 (dt, J = 7.03, 3.39 Hz, 1H), 2.72-2.88 (m, 2H), 3.23-3.31 (m, 2H), 7.66-7.83 (m, 4H), 7.96 (dd, J = 7.97, 1.82 Hz, 1H), 8.03-8.17 (m, 3H); ESI m/z 397.1 [M + 1]$^+$. | 16% |
| 6 | 4-cyclopropyl-3-(2-phenyl-5-(3-propionylphenyl)-1H-imidazol-4-yl)-1H-1,2,4-triazol-5(4H)-one hydrochloride | 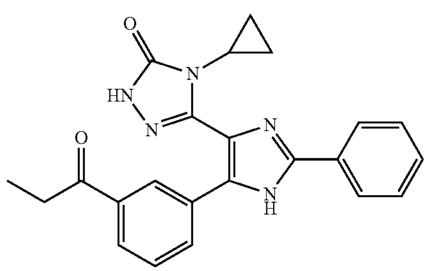 [SMILES: CCC(=O)c1cccc(-c2[nH]c(-c3ccccc3)nc2-c2n[nH]c(=O)n2C2CC2)c1] | A | $^1$H NMR (400 MHz, CD$_3$OD) δ 0.64-0.82 (m, 4H), 1.22 (t, J = 7.15 Hz, 3H), 2.50 (tt, J = 7.07, 3.65 Hz, 1H) 3.11 (q, J = 7.15 Hz, 2H), 7.58-7.70 (m, 4H), 7.90 (d, J = 7.78 Hz, 1H), 8.01-8.15 (m, 3H), 8.35 (s, 1H); ESI m/z 400 [M + 1]$^+$ | 63% |
| 7 | 4-cyclopropyl-3-(5-(1-methyl-1H-indazol-6-yl)-2-phenyl-1H-imidazol-4-yl)-1H-1,2,4-triazol-5(4H)-one hydrochloride | 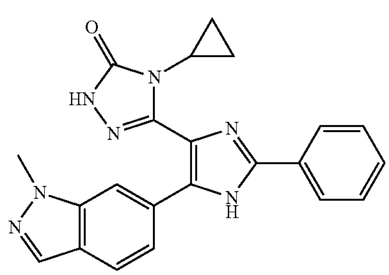 [SMILES: Cn1ncc2ccc(-c3[nH]c(-c4ccccc4)nc3-c3n[nH]c(=O)n3C3CC3)cc21] | A | $^1$H NMR (400 MHz, DMSO-d$_6$) δ 0.61-0.70 (m, 4H) 4.10 (s, 3H) 7.30 (dd, J = 8.41, 1.13 Hz, 1H) 7.51-7.69 (m, 3H) 7.83 (d, J = 8.53 Hz, 1H) 8.07-8.20 (m, 2H) 8.26 (d, J = 6.90 Hz, 2H) 12.08 (s, 1H); ESI m/z 398.2 [M + H]$^+$. | 4% |

TABLE 2-continued

Example Compounds

| Example | Chemical Name | Structure | General Procedure | Characterization | Yield |
|---|---|---|---|---|---|
| 8 | 3-(5-(3-acetyl-4-fluorophenyl)-2-phenyl-1H-imidazol-4-yl)-4-cyclopropyl-1H-1,2,4-triazol-5(4H)-one hydrochloride | 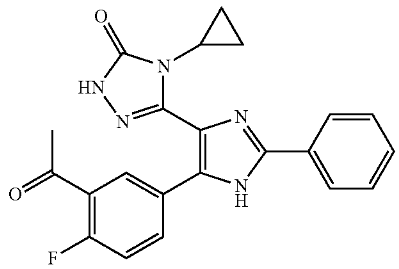 [SMILES: CC(=O)c1cc(-c2[nH]c(-c3ccccc3)nc2-c2n[nH]c(=O)n2C2CC2)ccc1F] | A | $^1$H NMR (400 MHz, CD$_3$OD) δ 0.67-0.74 (m, 2H), 0.76-0.84 (m, 2H), 2.45 (dt, J = 6.93, 3.37 Hz, 1H), 2.69 (d, J = 4.64 Hz, 3H), 7.50 (dd, J = 10.67, 8.66 Hz, 1H), 7.69-7.80 (m, 4H), 7.90-8.01 (m, 1H), 8.09 (d, J = 6.78 Hz, 2H), 8.27 (dd, J = 6.71, 2.45 Hz, 1H); ESI m/z 404 [M + 1]$^+$. | 29% |
| 9 | 3-(5-(3-acetyl-5-fluorophenyl)-2-phenyl-1H-imidazol-4-yl)-4-cyclopropyl-1H-1,2,4-triazol-5(4H)-one hydrochloride | 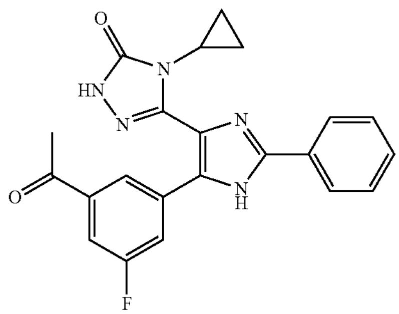 [SMILES: CC(=O)c1cc(F)cc(-c2[nH]c(-c3ccccc3)nc2-c2n[nH]c(=O)n2C2CC2)c1] | A | $^1$H NMR (400 MHz, DMSO-d$_6$) δ 0.61-0.73 (m, 4H) 2.62 (s, 3H) 2.81 (dt, J = 7.15, 3.33 Hz, 1H) 7.45-7.59 (m, 3H) 7.73 (dt, J = 9.25, 1.90 Hz, 1H) 7.86-7.91 (m, 1H) 8.11-8.19 (m, 3H) 11.98-12.10 (m, 1H); ESI m/z 404.1 [M + 1]$^+$ | 13% |
| 10 | 4-cyclopropyl-3-(5-(1-methyl-1H-indazol-5-yl)-2-phenyl-1H-imidazol-4-yl)-1H-1,2,4-triazol-5(4H)-one hydrochloride | 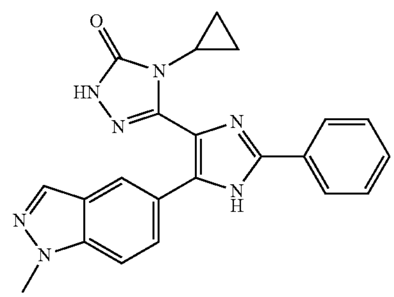 [SMILES: Cn1ncc2cc(-c3[nH]c(-c4ccccc4)nc3-c3n[nH]c(=O)n3C3CC3)ccc21] | A | $^1$H NMR (400 MHz, CD$_3$OD) δ 0.63-0.76 (m, 4H) 2.03-2.16 (m, 1H) 4.15 (s, 3H) 7.67-7.86 (m, 5H) 8.08-8.15 (m, 2H) 8.19 (s, 2H); ESI m/z 398.0 [M + 1]$^+$ | 54% |
| 11 | 3-(5-(5-acetyl-2-methylphenyl)-2-phenyl-1H-imidazol-4-yl)-4-cyclopropyl-1H-1,2,4-triazol-5(4H)-one hydrochloride | 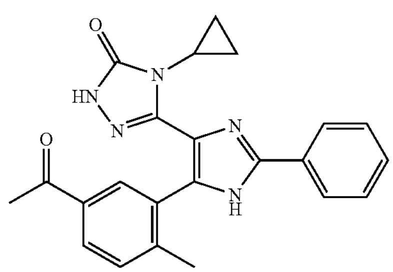 [SMILES: CC(=O)c1ccc(C)c(-c2[nH]c(-c3ccccc3)nc2-c2n[nH]c(=O)n2C2CC2)c1] | A | $^1$HNMR (400 MHz, DMSO-d$_6$) δ 0.64-0.84 (m, 4H) 2.28 (s, 3 H) 2.58 (s, 3 H) 7.45-7.61 (m, 4 H) 7.90-8.00 (m, 2 H) 8.11 (d, J = 7.28 Hz, 2 H) 11.73 (br. s., 1 H) ESI m/z 400.0 [M + 1]$^+$ | 43% |
| 12 | 3-(5-(5-acetylpyridin-3-yl)-2-phenyl-1H-imidazol-4-yl)-4-cyclopropyl-1H-1,2,4-triazol-5(4H)-one formate | 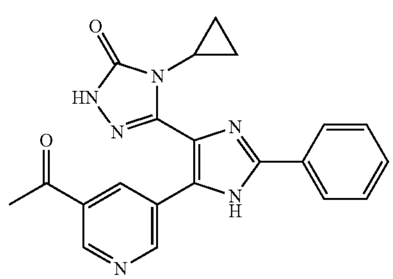 [SMILES: CC(=O)c1cncc(-c2[nH]c(-c3ccccc3)nc2-c2n[nH]c(=O)n2C2CC2)c1] | A | $^1$H NMR (300 MHz, DMSO-d$_6$) δ 0.61-0.77 (m, 1H) 2.67 (s, 3 H) 2.79-2.96 (m, 1 H) 7.41-7.59 (m, 3 H) 8.11 (d, J = 7.16 Hz, 2 H) 8.37 (br. s., 1 H) 8.62 (s, 1 H) 8.96-9.16 (m, 2 H) 11.89 (br. s., 1 H); ESI m/z 387.0 [M + 1]$^+$ | 22% |

TABLE 2-continued

Example Compounds

| Example | Chemical Name | Structure | General Procedure | Characterization | Yield |
|---|---|---|---|---|---|
| 13 | 4-cyclopropyl-3-(5-(3-methyl-1H-indazol-5-yl)-2-phenyl-1H-imidazol-4-yl)-1H-1,2,4-triazol-5(4H)-one hydrochloride | 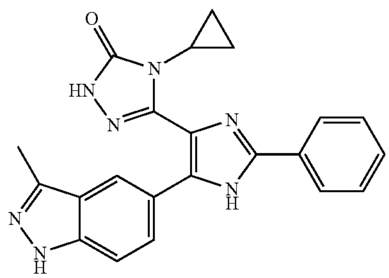 [SMILES: Cc1n[nH]c2ccc(-c3[nH]c(-c4ccccc4)nc3-c3n[nH]c(=O)n3C3CC3)cc12] | A | ¹HNMR (400 MHz, DMSO-d₆) δ 0.63 (d, J = 4.52 Hz, 4H) 2.60-2.66 (m, 1H) 7.45-7.59 (m, 5H) 8.15 (s, 1H) 8.22 (d, J = 7.40 Hz, 2H) 11.94 (br. s., 1H) 12.87 (br. s., 1H); ESI m/z 398.4 [M + 1]⁺ | 35% |
| 14 | 4-cyclopropyl-3-(5-(1-methyl-1H-benzo[d][1,2,3]triazol-6-yl)-2-phenyl-1H-imidazol-4-yl)-1H-1,2,4-triazol-5(4H)-one hydrochloride | 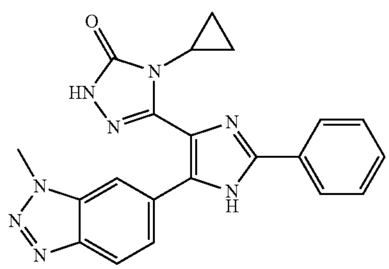 [SMILES: Cn1nnc2ccc(-c3[nH]c(-c4ccccc4)nc3-c3n[nH]c(=O)n3C3CC3)cc21] | A | ¹H-NMR (DMSO-d₆, 300 MHz): δ 11.90-12.05 (m, 1H), 8.22-8.33 (m, 1H), 8.11-8.21 (m, 2H), 7.99-8.11 (m, 1H), 7.56 (t, J = 7.4 Hz, 4H), 4.34 (br. s., 3H), 2.63-2.68 (m, 1H), 0.64 ppm (br. s., 4H); ESI m/z 399.1 [M + 1]⁺ | 31% |
| 15 | 4-cyclopropyl-3-(5-(1,3-dimethyl-1H-indazol-5-yl)-2-phenyl-1H-imidazol-4-yl)-1H-1,2,4-triazol-5(4H)-one hydrochloride | 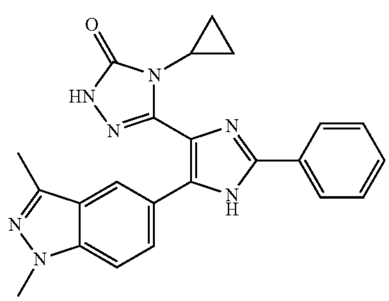 [SMILES: Cc1nn(C)c2ccc(-c3[nH]c(-c4ccccc4)nc3-c3n[nH]c(=O)n3C3CC3)cc12] | A | ¹H NMR (400 MHz, CD₃OD): δ 8.16-8.23 (m, 1H), 8.08-8.15 (m, 2H), 7.70-7.81 (m, 3H), 7.61-7.70 (m, 2H), 4.05 (s, 3H), 2.60 (s, 3H), 2.09-2.20 (m, 1H), 0.62-0.75 (m, 4H); ESI m/z 412.0 [M + 1]⁺ | 13% |
| 16 | 4-cyclopropyl-3-(5-(3-methylbenzo[d]isoxazol-5-yl)-2-phenyl-1H-imidazol-4-yl)-1H-1,2,4-triazol-5(4H)-one | 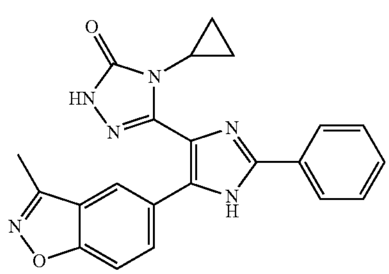 [SMILES: Cc1noc2ccc(-c3[nH]c(-c4ccccc4)nc3-c3n[nH]c(=O)n3C3CC3)cc12] | A | ¹H NMR (400 MHz, CDCl₃) δ 8.10-8.15 (m, 1H), 8.00-8.07 (m, 2H), 7.81-7.86 (m, 1H), 7.63-7.70 (m, 1H), 7.44-7.58 (m, 3H), 2.61 (s, 4H), 0.62-0.80 (m, 4H); ESI m/z 399.1 [M + 1]⁺ | 2% |
| 17 | 4-(cyclopropylmethyl)-3-(5-(1-methyl-1H-indazol-6-yl)-2-phenyl-1H-imidazol-4-yl)-1H-1,2,4-triazol-5(4H)-one | 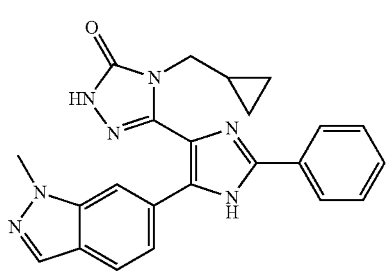 [SMILES: Cn1ncc2ccc(-c3[nH]c(-c4ccccc4)nc3-c3n[nH]c(=O)n3CC3CC3)cc21] | B | ¹H NMR (400 MHz, DMSO-d₆) δ 0.08-0.41 (m, 4H) 3.67 (br. s., 2H) 4.08 (s, 3H) 7.33-7.49 (m, 2H) 7.51-7.57 (m, 2H) 7.80 (d, J = 8.41 Hz, 1H) 8.03-8.09 (m, 2H) 8.10-8.14 (m, 2H) 11.79 (br. s., 1H); ESI m/z 412.1 [M + 1]⁺ | 68% |

TABLE 2-continued

Example Compounds

| Example | Chemical Name | Structure | General Procedure | Characterization | Yield |
|---|---|---|---|---|---|
| 18 | 4-isobutyl-3-(5-(1-methyl-1H-indazol-6-yl)-2-phenyl-1H-imidazol-4-yl)-1H-1,2,4-triazol-5(4H)-one | 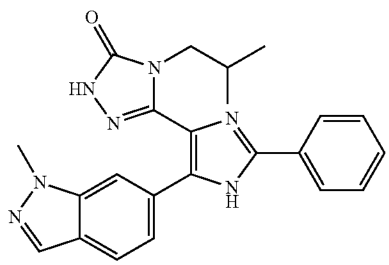 [SMILES: CC(C)Cn1c(-c2nc(-c3ccccc3)[nH]c2-c2ccc3cnn(C)c3c2)n[nH]c1=O] | B | $^1$H NMR (400 MHz, DMSO-d$_6$) δ 0.71 (d, J = 6.65 Hz, 6H) 1.87-2.07 (m, 1H) 3.66 (br. s., 2H) 4.00 (s, 3 H) 7.12 (br. s., 1H) 7.31 (br, s., 2H) 7.48-7.70 (m, 2H) 7.90 (br. s., 1H) 8.02-8.11 (m, 3H) 11.26-11.47 (m, 1H); ESI m/z 414.2 [M + 1]$^+$ | 44% |
| 19 | 4-cyclobutyl-3-(5-(1-methyl-1H-indazol-6-yl)-2-phenyl-1H-imidazol-4-yl)-1H-1,2,4-triazol-5(4H)-one | 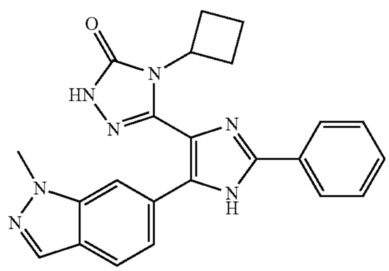 [SMILES: Cn1ncc2ccc(-c3[nH]c(-c4ccccc4)nc3-c3n[nH]c(=O)n3C3CCC3)cc21] | B | $^1$H NMR (400 MHz, DMSO-d$_6$) δ 1.40-1.62 (m, 2H) 1.83 (br. s., 2H) 2.79 (br. s., 2H) 4.03 (s, 3H) 4.51 (br. s., 1H) 7.19-7.53 (m, 4H) 7.67 (d, J = 8.16 Hz, 1H) 7.88-8.04 (m, 2H) 8.10 (d, J = 7.40 Hz, 2H) 11.67 (br. s., 1H) 13.21 (s, 1H); ESI m/z 412.2 [M + H]$^+$ | 50% |
| 20 | 3-(5-(1-methyl-1H-indazol-6-yl)-2-phenyl-1H-imidazol-4-yl)-4-neopentyl-1H-1,2,4-triazol-5(4H)-one | 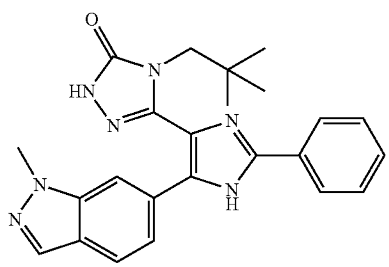 [SMILES: Cn1ncc2ccc(-c3[nH]c(-c4ccccc4)nc3-c3n[nH]c(=O)n3CC(C)(C)C)cc21] | B | $^1$H NMR (400 MHz, CD$_3$OD) δ 0.72 (s, 9H) 3.62 (br. s., 2H) 4.13 (s, 3H) 7.42 (dd, J = 8.47, 1.19 Hz, 1H) 7.50 (d, J = 7.15 Hz, 1H) 7.52-7.58 (m, 2H) 7.83 (d, J = 8.53 Hz, 1H) 8.01 (s, 1H) 8.04-8.09 (m, 3H); ESI m/z 428.3 [M + 1]$^+$ | 17% |
| 21 | 4-cyclopentyl-3-(5-(1-methyl-1H-indazol-6-yl)-2-phenyl-1H-imidazol-4-yl)-1H-1,2,4-triazol-5(4H)-one | 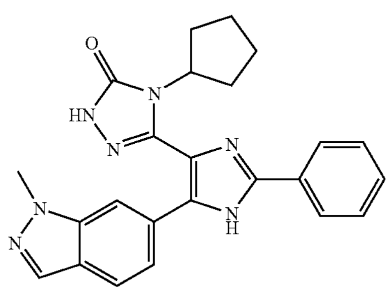 [SMILES: Cn1ncc2ccc(-c3[nH]c(-c4ccccc4)nc3-c3n[nH]c(=O)n3C3CCCC3)cc21] | B | $^1$H NMR (400 MHz, CD$_3$OD) δ 1.37-1.50 (m, 2H) 1.61 (br. s., 2H) 1.72 (br. s., 2H) 2.03 (dd, J = 12.86, 8.22 Hz, 2H) 4.11 (s, 3H) 4.24 (t, J = 8.78 Hz, 1H) 7.32 (d, J = 8.41 Hz, 1H) 7.47-7.59 (m, 3H) 7.80-7.89 (m, 2H) 8.03-8.10 (m, 3H); ESI m/z 426 [M + 1]$^+$ | 7% |
| 22 | 4-isopropyl-3-(5-(1-methyl-1H-indazol-6-yl)-2-phenyl-1H-imidazol-4-yl)-1H-1,2,4-triazol-5(4H)-one | 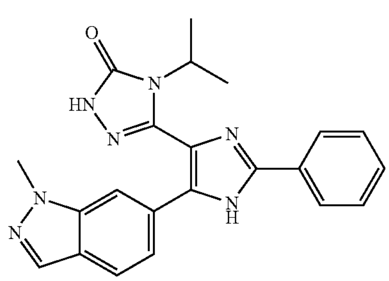 [SMILES: CC(C)n1c(-c2nc(-c3ccccc3)[nH]c2-c2ccc3cnn(C)c3c2)n[nH]c1=O] | B | $^1$H NMR (400 MHz, CD$_3$OD) δ 1.28 (d, J = 6.78 Hz, 6H) 4.12 (s, 3H) 4.14-4.19 (m, 1H) 7.34 (dd, J = 8.41, 1.38 Hz, 1H) 7.47-7.58 (m, 3H) 7.83 (d, J = 8.78 Hz, 1H) 7.91 (s, 1H) 8.02-8.10 (m, 3 H); ESI m/z 400.3 [M + 1]$^+$ | 10% |

TABLE 2-continued

Example Compounds

| Example | Chemical Name | Structure | General Procedure | Characterization | Yield |
|---|---|---|---|---|---|
| 23 | 4-cyclopropyl-3-(5-(1-methyl-1H-indazol-6-yl)-2-(pyridin-4-yl)-1H-imidazol-4-yl)-1H-1,2,4-triazol-5(4H)-one dihydrochloride | 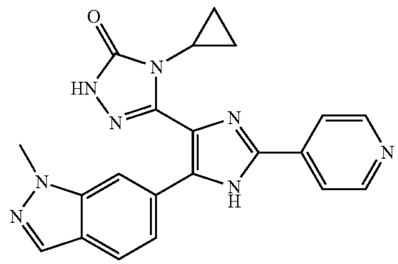 [SMILES: Cn1ncc2ccc(-c3[nH]c(-c4ccncc4)nc3-c3n[nH]c(=O)n3C3CC3)cc21] | C | $^1$H NMR (300 MHz, DMSO-$d_6$) δ 0.59-0.74 (m, 4H) 4.09 (s, 3H) 7.34 (d, J = 8.67 Hz, 1H) 7.44-7.68 (m, 1H) 7.84 (d, J = 8.48 Hz, 1H) 8.04-8.21 (m, 2H) 8.54 (d, J = 5.46 Hz, 2H) 8.94 (d, J = 6.40 Hz, 2H) 11.94 (br. s., 1H); ESI m/z 399.1 [M + 1]$^+$ | 48% |
| 24 | 4-cyclopropyl-3-(5-(1-methyl-1H-indazol-6-yl)-2-(pyridin-3-yl)-1H-imidazol-4-yl)-1H-1,2,4-triazol-5(4H)-one dihydrochloride | 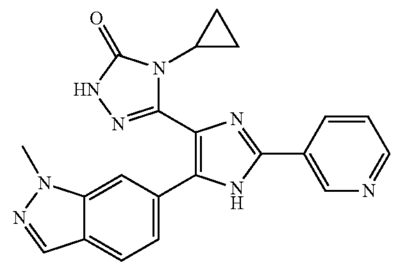 [SMILES: Cn1ncc2ccc(-c3[nH]c(-c4cccnc4)nc3-c3n[nH]c(=O)n3C3CC3)cc21] | C | $^1$H NMR (400 MHz, CD$_3$OD) δ 0.64-0.79 (m, 4H) 2.36-2.54 (m, 1H) 4.16 (s, 3H) 7.42 (dd, J = 8.41, 1.25 Hz, 1H) 7.91 (d, J = 8.28 Hz, 1H) 8.10 (s, 1H) 8.13 (s, 1H) 8.31 (dd, J = 8.22, 5.83 Hz, 1H) 9.00 (d, J = 5.27 Hz, 1H) 9.28 (d, J = 8.28 Hz, 1H) 9.61 (s, 1H); ESI m/z 399.2 [M + 1]$^+$ | 42% |
| 25 | 4-cyclopropyl-3-(5-(1-methyl-1H-indazol-6-yl)-2-(1-methyl-1H-pyrazol-4-yl)-1H-imidazol-4-yl)-1H-1,2,4-triazol-5(4H)-one hydrochloride | 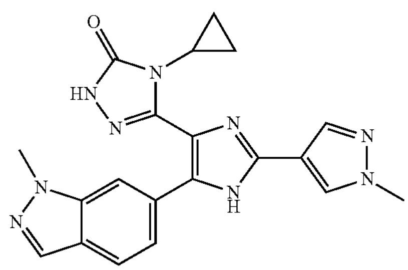 [SMILES: Cn1cc(-c2nc(-c3n[nH]c(=O)n3C3CC3)c(-c3ccc4cnn(C)c4c3)[nH]2)cn1] | C | $^1$H NMR (400 MHz, CD$_3$OD) δ 0.63-0.73 (m, 4H) 2.08-2.24 (m, 1H) 4.09 (s, 3H) 4.16 (s, 3H) 7.36 (d, J = 8.41 Hz, 1H) 7.96 (d, J = 8.41 Hz, 1H) 8.05 (s, 1H) 8.13 (s, 1H) 8.27 (s, 1H) 8.54 (s, 1H); ESI m/z 402.2 [M + 1]$^+$ | 38% |
| 26 | 4-cyclopropyl-3-(5-(1-methyl-1H-indazol-6-yl)-2-(1H-pyrazol-4-yl)-1H-imidazol-4-yl)-1H-1,2,4-triazol-5(4H)-one hydrochloride | 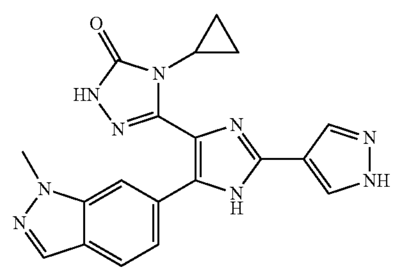 [SMILES: Cn1ncc2ccc(-c3[nH]c(-c4cn[nH]c4)nc3-c3n[nH]c(=O)n3C3CC3)cc21] | C | $^1$H NMR (400 MHz, CD$_3$OD) δ 0.60-0.76 (m, 4H) 2.07-2.18 (m, 1H) 4.16 (s, 3H) 7.34-7.40 (m, 1H) 7.97 (d, J = 8.41 Hz, 1H) 8.02 (s, 1H) 8.14 (d, J = 0.75 Hz, 1H) 8.47 (s, 2H); ESI m/z 388.0 [M + 1]$^+$ | 36% |
| 27 | 4-cyclopropyl-1-methyl-3-(5-(1-methyl-1H-indazol-6-yl)-2-phenyl-1H-imidazol-4-yl)-1H-1,2,4-triazol-5(4H)-one hydrochloride | 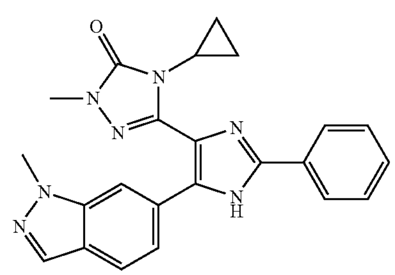 [SMILES: Cn1nc(-c2nc(-c3ccccc3)[nH]c2-c2ccc3cnn(C)c3c2)n(C2CC2)c1=O] | D | $^1$H-NMR(DMSO-$d_6$, 300 MHz): δ 8.17 (d, J = 7.3 Hz, 2H), 8.09 (d, J = 9.2 Hz, 2H), 7.77-7.85 (m, 1H), 7.44-7.62 (m, 3H), 7.27-7.34 (m, 1H), 4.08 (s, 3H), 3.39 (s, 3H), 1.12-1.27 (m, 1H), 0.63 ppm (d, J = 4.5 Hz, 4H); ESI m/z 412.0 [M + 1]$^+$ | 20% |

Example 28: Inhibition of Tetra-Acetylated histoneH4 Binding Individual BET Bromodomains Proteins were cloned and overexpressed with a N-terminal 6×His tag, then purified by nickel affinity followed by size exclusion chromatography. Briefly, E. coli BL21(DE3) cells were transformed with a recombinant expression vector encoding N-terminally Nickel affinity tagged bromodomains from Brd2, Brd3, Brd4. Cell cultures were incubated at 37° C. with shaking to the appropriate density and induced overnight with IPTG. The supernatant of lysed cells was loaded onto Ni-IDA column for purification. Eluted protein was pooled, concentrated and further purified by size exclusion chromatography. Fractions representing monomeric protein were pooled, concentrated, aliquoted, and frozen at −80° C. for use in subsequent experiments.

Binding of tetra-acetylated histone H4 peptide (Millipore) and BET bromodomains was confirmed by Amplified Luminescent Proximity Homogenous Assay (AlphaScreen). N-terminally His-tagged bromodomains (BRD4(1) at 20 nM and BRD4(2) at 100 nM) and biotinylated tetra-acetylated histone H4 (10-25 nM) were incubated in the presence of nickel chelate acceptor beads and streptavidin donor beads (PerkinAlmer, 6760000K) added to a final concentration of 2 μg/ml under green light in a white 96 well microtiter plate (Greiner). For inhibition assays, serially diluted compounds were added to the reaction mixtures in a 0.1% final concentrations of DMSO. Final buffer concentrations were 50 mM HEPES, 100 mM NaCl and 0.1% BSA buffer, pH 7.4 and optimized to 30 min incubation time. Assay plates were read at 570 nM on a Synergy H4 Plate Reader (Biotek). $IC_{50}$ values were determined from a dose response curve.

Compounds with an $IC_{50}$ value less than or equal to 0.3 μM were deemed to be highly active (+++); compounds with an $IC_{50}$ value between 0.3 and 3 μM were deemed to be very active (++); compounds with an $IC_{50}$ value between 3 and 30 μM were deemed to be active (+).

TABLE 3

Inhibition of Tetra-acetylated Histone H4 Binding to Brd4 bromodomain 1 (BRD4(1)) and Brd 4 bromodomain 2 (BRD4(2))

| Example Number | Alpha Screen BRD4(1) | Alpha Screen BRD4(2) | Example Number | Alpha Screen BRD4(1) | Alpha Screen BRD4(2) | Example Number | Alpha Screen BRD4(1) | Alpha Screen BRD4(2) |
|---|---|---|---|---|---|---|---|---|
| 1 | +++ | + | 2 | + | + | 3 | + | + |
| 4 | + | Not Active | 5 | Not Active | Not Active | 6 | ++ | + |
| 7 | +++ | Not Active | 8 | +++ | Not Active | 9 | ++ | Not Active |
| 10 | + | ++ | 11 | + | Not Active | 12 | + | ++ |
| 13 | ++ | ++ | 14 | +++ | +++ | 15 | ++ | + |
| 16 | +++ | ++ | 17 | Not Active | Not Active | 18 | ++ | + |
| 19 | ++ | + | 20 | ++ | + | 21 | + | Not Active |
| 22 | + | + | 23 | +++ | + | 24 | + | + |
| 25 | ++ | + | 26 | + | + | 27 | + | Not Active |

Example 29: Inhibition of cMYC Expression in Cancer Cell Lines

MV4-11 cells (CRL-9591) were plated at a density of 2.5×10⁴ cells per well in 96 well U-bottom plates and treated with increasing concentrations of test compound or DMSO (0.1%) in IMDM media containing 10% FBS and penicillin/streptomycin, and incubated for 3 h at 37° C. Triplicate wells were used for each concentration. Cells were pelleted by centrifugation and harvested using the mRNA Catcher PLUS kit according to manufacturer's instructions. The eluted mRNA isolated was then used in a one-step quantitative real-time PCR reaction, using components of the RNA UltraSense™ One-Step Kit (Life Technologies) together with Applied Biosystems TaqMan® primer-probes for cMYC and Cyclophilin. Real-time PCR plates were run on a ViiA™7 real time PCR machine (Applied Biosystems), data was analyzed, normalizing the Ct values for cMYC to an internal control, prior to determining the fold expression of each sample, relative to the control.

Compounds with an $IC_{50}$ value less than or equal to 0.3 μM were deemed to be highly active (+++); compounds with an $IC_{50}$ value between 0.3 and 3 μM were deemed to be very active (++); compounds with an $IC_{50}$ value between 3 and 30 μM were deemed to be active (+).

TABLE 4

Inhibition of c-myc Activity in Human AML MV4-11 cells

| Example Number | c-myc activity | Example Number | c-myc activity | Example Number | c-myc activity | Example Number | c-myc activity |
|---|---|---|---|---|---|---|---|
| 1 | + | 2 | Not Active | 4 | + | 6 | + |
| 7 | + | 8 | Not Active | 9 | + | 10 | Not Active |
| 13 | + | 14 | + | 18 | Not Active | 19 | + |

Example 30: Inhibition of Cell Proliferation in Cancer Cell Lines

MV4-11 cells (CRL-9591) were plated at a density of 5×10⁴ cells per well in 96 well flat bottom plates and treated with increasing concentrations of test compound or DMSO (0.1%) in IMDM media containing 10% FBS and penicillin/streptomycin. Triplicate wells were used for each concentration and a well containing only media was used as a control. Plates were incubated at 37° C., 5% $CO_2$ for 72 h before adding 20 μL of the Cell Titer Aqueous One Solution (Promega) to each well and incubated at 37° C., 5% $CO_2$ for an additional 3-4 h. The absorbance was read at 490 nm in a spectrophotometer and the percentage of cell titer relative to DMSO-treated cells was calculated after correcting for background by subtracting the blank well's signal. $IC_{50}$ values were calculated using the GraphPad Prism software.

Compounds with an $IC_{50}$ value less than or equal to 0.3 μM were deemed to be highly active (+++); compounds with an $IC_{50}$ value between 0.3 and 3 μM were deemed to be very active (++); compounds with an $IC_{50}$ value between 3 and 30 μM were deemed to be active (+).

TABLE 5

Inhibition of Cell Proliferation in Human AML MV-4-11 cells

| Example Number | Cell Proliferation activity | Example Number | Cell Proliferation activity | Example Number | Cell Proliferation activity | Example Number | Cell Proliferation activity |
|---|---|---|---|---|---|---|---|
| 1 | + | 2 | Not Active | 4 | + | 6 | + |
| 7 | + | 8 | Not Active | 9 | + | 10 | Not Active |
| 13 | + | 14 | + | — | — | — | — |

Example 31: Inhibition of hIL-6 mRNA Transcription

Human leukemic monocyte lymphoma U937 cells (CRL-1593.2) were plated at a density of 3.2×104 cells per well in a 96-well plate in 100 μL RPMI-1640 containing 10% FBS and penicillin/streptomycin, and differentiated into macrophages for 3 days in 60 ng/mL PMA (phorbol-13-myristate-12-acetate) at 37° C. in 5% $CO_2$ prior to the addition of compound. The cells were pretreated for 1 h with increasing concentrations of test compound in 0.1% DMSO prior to stimulation with 1 ug/mL lipopolysaccharide from *Escherichia coli*. Triplicate wells were used for each concentration. The cells were incubated at 37° C., 5% $CO_2$ for 3 h before the cells were harvested. At time of harvest, media was removed and cells were rinsed in 200 μL PBS. Cells were harvested using the mRNA Catcher PLUS kit according to manufacturer's instructions. The eluted mRNA was then used in a one-step quantitative real-time PCR reaction using components of the RNA UltraSense™ One-Step Kit (Life Technologies) together with Applied Biosystems TaqMan® primer-probes for hIL-6 and Cyclophilin. Real-time PCR plates were run on a ViiA™7 real time PCR machine (Applied Biosystems), data was analyzed, normalizing the Ct values for hIL-6 to an internal control, prior to determining the fold expression of each sample, relative to the control.

Compounds with an $IC_{50}$ value less than or equal to 0.3 μM were deemed to be highly active (+++); compounds with an $IC_{50}$ value between 0.3 and 3 μM were deemed to be very active (++); compounds with an $IC_{50}$ value between 3 and 30 μM were deemed to be active J+).

TABLE 6

Inhibition of hIL-6 mRNA Transcription

| Example Number | IL-6 activity | Example Number | IL-6 activity | Example Number | IL-6 activity | Example Number | IL-6 activity |
|---|---|---|---|---|---|---|---|
| 1 | + | 7 | + | 8 | + | 9 | + |
| 14 | + | — | — | — | — | — | — |

Examples 32: In Vivo Efficacy in Athymic Nude Mouse Strain of an Acute Myeloid Leukemia Xenograft Model Using MV4-11 Cells MV4-11 cells (ATCC) are grown under standard cell culture conditions and (NCr) nu/nu fisol strain of female mice age 6-7 weeks are injected with 5×10⁶ cells/animal in 100 μL PBS+100 μL Matrigel in the lower left abdominal flank. By approximately day 18-21 after MV4-11 cells injection, mice are randomized based on tumor volume (L×W×H)/2) of average ~100-300 mm³. Mice are dosed orally with compound at 5 to 120 mg/kg b.i.d and/or q.d. on a continuous dosing schedule and at 2.5 to 85 mg/kg q.d. on a 5 day on 2 day off, 100 mg/kg q.d. on a 4 day on and 3 day off, 135 mg/kg q.d. on a 3 day on and 4 day off, 180 mg/kg on a 2 day on and 5 day off and 240 mg/kg on a 1 day on and 6 days off dosing schedules in EA006 formulation at 10 mL/kg body weight dose volume. Tumor measurements are taken with electronic micro calipers and body weights measured on alternate days beginning from dosing period. The average tumor volumes, percent Tumor Growth Inhibition (TGI) and % change in body weights are compared relative to Vehicle control animals. The means, statistical analysis and the comparison between groups are calculated using Student's t-test in Excel.

Other embodiments of the present disclosure will be apparent to those skilled in the art from consideration of the specification and practice of the present disclosure disclosed herein. It is intended that the specification and examples be considered as exemplary only, with a true scope and spirit of the present disclosure being indicated by the following claims.

What is claimed is:

1. A compound of Formula I:

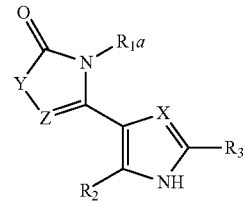

Formula I or a stereoisomer, tautomer, pharmaceutically acceptable salt, or hydrate thereof, wherein:

X is selected from CH and N;

Y is selected from —NH, —N—$R_{1b}$ and oxygen;

Z is selected from N, and —CH—;

$R_{1a}$ and $R_{1b}$ are independently selected from ($C_1$-$C_6$) alkyl, ($C_3$-$C_{10}$)carbocycle, and ($C_2$-$C_{10}$)heterocycle, each of which may be optionally substituted with 1 to 3 groups selected from $R_4$;

$R_2$ is selected from ($C_5$-$C_{10}$)aryl and ($C_5$-$C_{10}$)heteroaryl, each of which may be optionally substituted with 1 to 5 groups selected from $R_5$;

$R_3$ is selected from $(C_3\text{-}C_{10})$ carbocycle and $(C_2\text{-}C_{10})$ heterocycle, each of which may be optionally substituted with 1 to 5 groups selected from $R_5$;

each $R_4$ is independently selected from deuterium, $(C_1\text{-}C_6)$alkyl, $(C_3\text{-}C_8)$cycloalkyl, $(C_1\text{-}C_6)$alkoxy, amino, —NHC(O)NH—$(C_1\text{-}C_6)$alkyl, halogen, amide, —CF$_3$, —CN, —N$_3$, ketone, —S(O)—$(C_1\text{-}C_4)$alkyl, —SO$_2$—$(C_1\text{-}C_6)$alkyl, thio-$(C_1\text{-}C_6)$alkyl, —COOH, and ester, each of which may be optionally substituted with F, Cl, Br, —OH, —NH$_2$, —NHMe, —OMe, —SMe, oxo, and/or thio-oxo; and each $R_5$ is independently selected from deuterium, $(C_1\text{-}C_5)$alkyl, $(C_1\text{-}C_6)$alkoxy, amino, —NHC(O)NH—$(C_1\text{-}C_6)$alkyl, halogen, amide, —CF$_3$, —CN, —N$_3$, $(C_1\text{-}C_6)$ ketone, —S(O)—$(C_1\text{-}C_4)$alkyl, —SO$_2$—$(C_1\text{-}C_6)$alkyl, thio-$(C_1\text{-}C_6)$alkyl, —COOH, and ester, each of which may be optionally substituted with F, Cl, Br, —OH, —NH$_2$, —NHMe, —OMe, —SMe, oxo, and/or thio-oxo.

2. A compound according to claim 1, wherein the compound is a compound of Formula Ia:

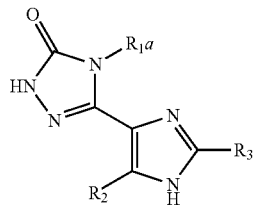

Formula Ia or a stereoisomer, tautomer, pharmaceutically acceptable salt, or hydrate thereof,
wherein:
$R_{1a}$ is selected from $(C_1\text{-}C_6)$alkyl, $(C_3\text{-}C_{10})$carbocycle, and $(C_2\text{-}C_{10})$heterocycle, each of which may be optionally substituted with 1 to 3 groups selected from $R_4$;

$R_2$ is selected from $(C_5\text{-}C_{10})$aryl and $(C_5\text{-}C_{10})$heteroaryl, each of which may be optionally substituted with 1 to 5 groups selected from $R_5$;

$R_3$ is selected from $(C_3\text{-}C_{10})$ carbocycle and $(C_2\text{-}C_{10})$ heterocycle, each of which may be optionally substituted with 1 to 5 groups selected from $R_5$;

each $R_4$ is independently selected from deuterium, $(C_1\text{-}C_6)$alkyl, $(C_3\text{-}C_8)$cycloalkyl, $(C_1\text{-}C_6)$alkoxy, amino, —NHC(O)NH—$(C_1\text{-}C_6)$alkyl, halogen, amide, —CF$_3$, —CN, —N$_3$, ketone, —S(O)—$(C_1\text{-}C_4)$alkyl, —SO$_2$—$(C_1\text{-}C_6)$alkyl, thio-$(C_1\text{-}C_6)$alkyl, —COOH, and ester, each of which may be optionally substituted with F, Cl, Br, —OH, —NH$_2$, —NHMe, —OMe, —SMe, oxo, and/or thio-oxo; and each $R_5$ is independently selected from deuterium, $(C_1\text{-}C_6)$alkyl, $(C_1\text{-}C_6)$alkoxy, amino, —NHC(O)NH—$(C_1\text{-}C_6)$alkyl, halogen, amide, —CF$_3$, —CN, —N$_3$, $(C_1\text{-}C_6)$ketone, —S(O)—$(C_1\text{-}C_4)$alkyl, —SO$_2$—$(C_1\text{-}C_6)$alkyl, thio-$(C_1\text{-}C_6)$alkyl, —COOH, and ester, each of which may be optionally substituted with F, Cl, Br, —OH, —NH$_2$, —NHMe, —OMe, —SMe, oxo, and/or thio-oxo.

3. The compound according to claim 1, wherein Y is —NR$_{1b}$.

4. The compound according to claim 2, wherein $R_{1a}$ is selected from the following structures,

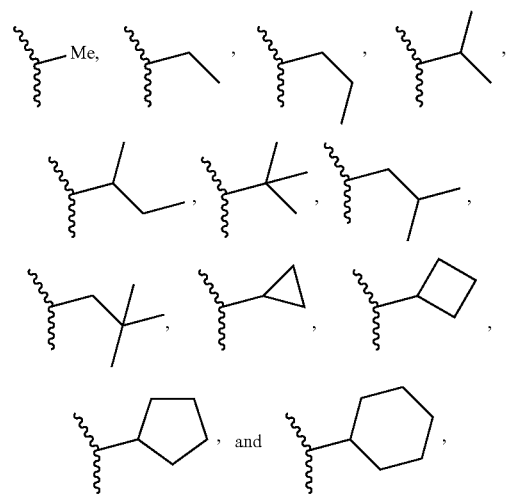

each of which may be optionally substituted with 1 to 3 groups selected from $R_4$, and

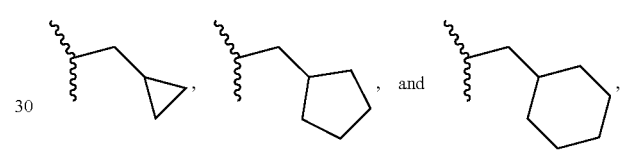

each of which may be optionally substituted with F, Cl, Br, —OH, —NH$_2$, —NHMe, —OMe, —SMe, oxo, and/or thio-oxo.

5. The compound according to claim 4, wherein $R_{1a}$ is selected from the following structures:

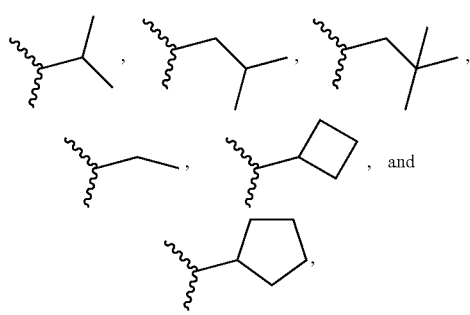

each of which may be optionally substituted with 1 to 3 groups selected from $R_4$, and

which may be optionally substituted with F, Cl, Br, —OH, —NH$_2$, —NHMe, —OMe, —SMe, oxo, and/or thio-oxo.

6. The compound according to claim 5, wherein R$_{1a}$ is

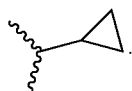 [SMILES: *C1CC1]

7. The compound according to claim 2, wherein R$_{1a}$ is selected from the following structures, which may be optionally substituted with 1 to 3 groups selected from R$_4$:

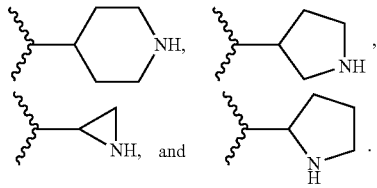

8. The compound according to claim 3, wherein R$_{1b}$ is (C$_1$-C$_6$)alkyl.

9. The compound according to claim 8, wherein R$_{1b}$ is selected from methyl and ethyl.

10. The compound according to claim 2, wherein R$_2$ is selected from bicyclic (C$_5$-C$_{10}$)aryl and bicyclic (C$_5$-C$_{10}$) heteroaryl groups optionally substituted with 1 to 5 R$_5$ groups.

11. The compound according to claim 2, wherein R$_2$ is selected from the following:

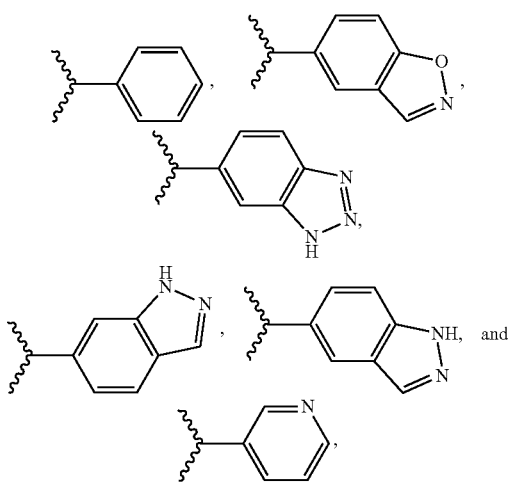

each of which may be optionally substituted with 1 to 2 groups selected from (C$_1$-C$_6$)alkyl, halogen, ketone, amide, and ester, and

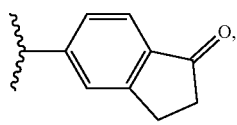 [SMILES: *c1ccc2c(c1)CCC2=O]

which may be optionally substituted with F, Cl, Br, —OH, —NH$_2$, —NHMe, —OMe, —SMe, oxo, and/or thiooxo.

12. The compound according to claim 11, wherein R$_2$ is

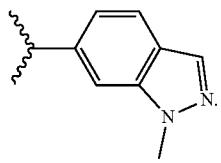 [SMILES: *c1ccc2cnn(C)c2c1]

13. The compound according to claim 2, wherein R$_3$ is selected from the following structures:

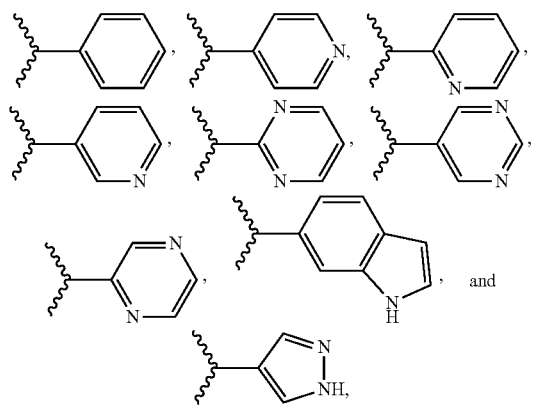

each of which may be optionally substituted with 1 to 5 groups selected from R$_5$.

14. The compound according to claim 13, wherein R$_3$ is selected from the following structures:

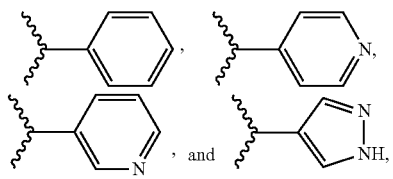

each of which may be optionally substituted with 1 to 5 groups selected from R$_5$.

15. The compound according to claim 14, wherein R$_3$ is an unsubstituted phenyl group.

16. A compound selected from:
3-(5-(3-Acetylphenyl)-2-phenyl-1H-imidazol-4-yl)-4-cyclopropyl-1H-1,2,4-triazol-5(4H)-one;
Methyl 3-(4-(4-cyclopropyl-5-oxo-4,5-dihydro-1H-1,2,4-triazol-3-yl)-2-phenyl-1H-imidazol-5-yl)-4-methylbenzoate;
3-(4-(4-Cyclopropyl-5-oxo-4,5-dihydro-1H-1,2,4-triazol-3-yl)-2-phenyl-1H-imidazol-5-yl)-N-methylbenzamide;
3-(4-(4-Cyclopropyl-5-oxo-4,5-dihydro-1H-1,2,4-triazol-3-yl)-2-phenyl-1H-imidazol-5-yl)benzamide;
4-Cyclopropyl-3-(5-(3-oxo-2,3-dihydro-1H-inden-5-yl)-2-phenyl-1H-imidazol-4-yl)-1H-1,2,4-triazol-5(4H)-one;
4-Cyclopropyl-3-(2-phenyl-5-(3-propionylphenyl)-1H-imidazol-4-yl)-1H-1,2,4-triazol-5(4H)-one;
4-Cyclopropyl-3-(5-(1-methyl-1H-indazol-6-yl)-2-phenyl-1H-imidazol-4-yl)-1H-1,2,4-triazol-5(4H)-one;

3-(5-(3-Acetyl-4-fluorophenyl)-2-phenyl-1H-imidazol-4-yl)-4-cyclopropyl-1H-1,2,4-triazol-5(4H)-one;
3-(5-(3-Acetyl-5-fluorophenyl)-2-phenyl-1H-imidazol-4-yl)-4-cyclopropyl-1H-1,2,4-triazol-5(4H)-one;
4-cyclopropyl-3-(5-(1-methyl-1H-indazol-5-yl)-2-phenyl-1H-imidazol-4-yl)-1H-1,2,4-triazol-5(4H)-one;
3-(5-(5-acetyl-2-methylphenyl)-2-phenyl-1H-imidazol-4-yl)-4-cyclopropyl-1H-1,2,4-triazol-5(4H)-one;
3-(5-(5-acetylpyridin-3-yl)-2-phenyl-1H-imidazol-4-yl)-4-cyclopropyl-1H-1,2,4-triazol-5(4H)-one formate;
4-cyclopropyl-3-(5-(1,3-dimethyl-1H-indazol-5-yl)-2-phenyl-1H-imidazol-4-yl)-1H-1,2,4-triazol-5(4H)-one;
4-(Cyclopropylmethyl)-3-(5-(1-methyl-1H-indazol-6-yl)-2-phenyl-1H-imidazol-4-yl)-1H-1,2,4-triazol-5(4H)-one;
4-Isopropyl-3-(5-(1-methyl-1H-indazol-6-yl)-2-phenyl-1H-imidazol-4-yl)-1H-1,2,4-triazol-5(4H)-one;
4-(tert-Butyl)-3-(5-(1-methyl-1H-indazol-6-yl)-2-phenyl-1H-imidazol-4-yl)-1H-1,2,4-triazol-5(4H)-one;
4-Cyclopentyl-3-(5-(1-methyl-1H-indazol-6-yl)-2-phenyl-1H-imidazol-4-yl)-1H-1,2,4-triazol-5(4H)-one;
4-Cyclobutyl-3-(5-(1-methyl-1H-indazol-6-yl)-2-phenyl-1H-imidazol-4-yl)-1H-1,2,4-triazol-5(4H)-one;
4-Cyclohexyl-3-(5-(1-methyl-1H-indazol-6-yl)-2-phenyl-1H-imidazol-4-yl)-1H-1,2,4-triazol-5(4H)-one;
4-Isobutyl-3-(5-(1-methyl-1H-indazol-6-yl)-2-phenyl-1H-imidazol-4-yl)-1H-1,2,4-triazol-5(4H)-one;
3-(5-(1-Methyl-1H-indazol-6-yl)-2-phenyl-1H-imidazol-4-yl)-4-neopentyl-1H-1,2,4-triazol-5(4H)-one;
4-Cyclopropyl-1-methyl-3-(5-(1-methyl-1H-indazol-6-yl)-2-phenyl-1H-imidazol-4-yl)-1H-1,2,4-triazol-5(4H)-one;
4-Cyclopropyl-1-ethyl-3-(5-(1-methyl-1H-indazol-6-yl)-2-phenyl-1H-imidazol-4-yl)-1H-1,2,4-triazol-5(4H)-one;
4-Cyclopropyl-1-(cyclopropylmethyl)-3-(5-(1-methyl-1H-indazol-6-yl)-2-phenyl-1H-imidazol-4-yl)-1H-1,2,4-triazol-5(4H)-one;
4-Cyclopropyl-1-(2-methoxyethyl)-3-(5-(1-methyl-1H-indazol-6-yl)-2-phenyl-1H-imidazol-4-yl)-1H-1,2,4-triazol-5(4H)-one;
4-Cyclopropyl-3-(5-(3-methylbenzo[d]isoxazol-5-yl)-2-phenyl-1H-imidazol-4-yl)-1H-1,2,4-triazol-5(4H)-one;
4-Cyclopropyl-3-(5-(1-methyl-1H-benzo[d][1,2,3]triazol-6-yl)-2-phenyl-1H-imidazol-4-yl)-1H-1,2,4-triazol-5(4H)-one; 4-Cyclopropyl-3-(5-(3-methyl-1H-indazol-5-yl)-2-phenyl-1H-imidazol-4-yl)-1H-1,2,4-triazol-5(4H)-one;
4-Cyclopropyl-3-(5-(1-methyl-1H-indazol-6-yl)-2-(pyridin-4-yl)-1H-imidazol-4-yl)-1H-1,2,4-triazol-5(4H)-one;
4-Cyclopropyl-3-(5-(1-methyl-1H-indazol-6-yl)-2-(pyridin-3-yl)-1H-imidazol-4-yl)-1H-1,2,4-triazol-5(4H)-one;
3-(2-(1H-Indol-6-yl)-5-(1-methyl-1H-indazol-6-yl)-1H-imidazol-4-yl)-4-cyclopropyl-1H-1,2,4-triazol-5(4H)-one;
4-Cyclopropyl-3-(5-(1-methyl-1H-indazol-6-yl)-2-(1H-pyrazol-4-yl)-1H-1,2,4-triazol-5(4H)-one;
4-Cyclopropyl-3-(5-(1-methyl-1H-indazol-6-yl)-2-(1-methyl-1H-pyrazol-4-yl)-1H-imidazol-4-yl)-1H-1,2,4-triazol-5(4H)-one;
and stereoisomers, tautomers, pharmaceutically acceptable salts, and hydrates thereof.

17. A compound is selected from:
3-(5-(3-acetylphenyl)-2-phenyl-1H-imidazol-4-yl)-4-cyclopropyl-1H-1,2,4-triazol-5(4H)-one hydrochloride;
methyl 3-(4-(4-cyclopropyl-5-oxo-4,5-dihydro-1H-1,2,4-triazol-3-yl)-2-phenyl-1H-imidazol-5-yl)-4-methyl benzoate hydrochloride;
3-(4-(4-cyclopropyl-5-oxo-4,5-dihydro-1H-1,2,4-triazol-3-yl)-2-phenyl-1H-imidazol-5-yl)-N-methyl benzamide hydrochloride;
3-(4-(4-cyclopropyl-5-oxo-4,5-dihydro-1H-1,2,4-triazol-3-yl)-2-phenyl-1H-imidazol-5-yl)benzamide hydrochloride;
4-cyclopropyl-3-(5-(3-oxo-2,3-dihydro-1H-inden-5-yl)-2-phenyl-1H-imidazol-4-yl)-1H-1,2,4-triazol-5(4H)-one hydrochloride;
4-cyclopropyl-3-(2-phenyl-5-(3-propionylphenyl)-1H-imidazol-4-yl)-1H-1,2,4-triazol-5(4H)-one hydrochloride;
4-cyclopropyl-3-(5-(1-methyl-1H-indazol-6-yl)-2-phenyl-1H-imidazol-4-yl)-1H-1,2,4-triazol-5(4H)-one hydrochloride;
3-(5-(3-acetyl-4-fluorophenyl)-2-phenyl-1H-imidazol-4-yl)-4-cyclopropyl-1H-1,2,4-triazol-5(4H)-one hydrochloride;
3-(5-(3-acetyl-5-fluorophenyl)-2-phenyl-1H-imidazol-4-yl)-4-cyclopropyl-1H-1,2,4-triazol-5(4H)-one hydrochloride;
4-cyclopropyl-3-(5-(1-methyl-1H-indazol-5-yl)-2-phenyl-1H-imidazol-4-yl)-1H-1,2,4-triazol-5(4H)-one hydrochloride;
3-(5-(5-acetyl-2-methylphenyl)-2-phenyl-1H-imidazol-4-yl)-4-cyclopropyl-1H-1,2,4-triazol-5(4H)-one hydrochloride;
4-cyclopropyl-3-(5-(3-methyl-1H-indazol-5-yl)-2-phenyl-1H-imidazol-4-yl)-1H-1,2,4-triazol-5(4H)-one hydrochloride;
4-cyclopropyl-3-(5-(1-methyl-1H-benzo[d][1,2,3]triazol-6-yl)-2-phenyl-1H-imidazol-4-yl)-1H-1,2,4-triazol-5(4H)-one hydrochloride;
4-cyclopropyl-3-(5-(1,3-dimethyl-1H-indazol-5-yl)-2-phenyl-1H-imidazol-4-yl)-1H-1,2,4-triazol-5(4H)-one hydrochloride;
4-cyclopropyl-3-(5-(1-methyl-1H-indazol-6-yl)-2-(pyridin-4-yl)-1H-imidazol-4-yl)-1H-1,2,4-triazol-5(4H)-one dihydrochloride;
4-cyclopropyl-3-(5-(1-methyl-1H-indazol-6-yl)-2-(pyridin-3-yl)-1H-imidazol-4-yl)-1H-1,2,4-triazol-5(4H)-one dihydrochloride;
4-cyclopropyl-3-(5-(1-methyl-1H-indazol-6-yl)-2-(1-methyl-1H-pyrazol-4-yl)-1H-imidazol-4-yl)-1H-1,2,4-triazol-5(4H)-one hydrochloride;
4-cyclopropyl-3-(5-(1-methyl-1H-indazol-6-yl)-2-(1H-pyrazol-4-yl)-1H-imidazol-4-yl)-1H-1,2,4-triazol-5(4H)-one 6hydrochloride;
4-cyclopropyl-1-methyl-3-(5-(1-methyl-1H-indazol-6-yl)-2-phenyl-1H-imidazol-4-yl)-1H-1,2,4-triazol-5(4H)-one hydrochloride;
and stereoisomers, tautomers, and hydrates thereof.

18. A pharmaceutical composition comprising the compound of claim 1, and a pharmaceutically acceptable carrier.

19. A method for inhibition of BET protein function comprising administering a therapeutically effective amount of the compound of claim 1 to a mammal in need thereof.

20. A method of treating a disease or disorder comprising administering a therapeutically effective amount of the compound according to claim 1 to a mammal in need thereof slam-96, wherein the disease or disorder
is selected from Acute Disseminated Encephalomyelitis, Agammaglobulinemia, Allergic Disease, Ankylosing spondylitis, Anti-GBM/Anti-TBM nephritis, Anti-phospholipid syndrome, Autoimmune aplastic anemia, Autoimmune hepatitis, Autoimmune inner ear disease, Autoimmune myocarditis, Autoimmune pancreatitis, Autoimmune retinopathy, Autoimmune thrombocytopenic purpura, Behcet's Disease, Bullous pemphigoid, Castleman's Disease, Celiac Disease, Churg-Strauss syndrome, Crohn's Disease, Cogan's syndrome, Dry eye syndrome, Essential mixed cryoglobulinemia, Dermatomyositis, Devic's Disease, Encephalitis, Eosinophlic esophagitis, Eosinophilic fasciitis, Erythema nodosum, Giant cell arteritis, Glomerulonephritis, Goodpasture's syndrome, Granulomatosis with Polyangiitis (Wegener's), Graves' Disease, Guillain-Barre syndrome, Hashimoto's thyroiditis, Hemolytic anemia, Henoch-Schonlein purpura, idiopathic pulmonary fibrosis, IgA nephropathy; Inclusion body myositis, Type I diabetes, Interstitial cystitis, Kawasaki's Disease, Leukocytoclastic vasculitis, Lichen planus, Lupus (SLE), Microscopic polyangitis, Multiple sclerosis, Myasthenia gravis, myositis, Optic neuritis, Pemphigus, POEMS syndrome, Polyarteritis nodosa, Primary biliary cirrhosis, Psoriasis, Psoriatic arthritis, Pyoderma gangrenosum, Relapsing polychondritis, Rheumatoid arthritis, Sarcoidosis, Scleroderma, Sjogren's syndrome, Takayasu's arteritis, Transverse myelitis, Ulcerative colitis, Uveitis, Vitiligo, sinusitis, pneumonitis, osteomyelitis, gastritis, enteritis, gingivitis, appendicitis, irritable bowel syndrome, tissue graft rejection, chronic obstructive pulmonary disease (COPD), septic shock, osteoarthritis, acute gout, acute lung injury, acute renal failure, burns, Herxheimer reaction, and SIRS associated with viral infections, comprising administering a therapeutically effective amount of the compound according to claim 1 to a mammal in need thereof.

21. A method of treating cancer comprising administering a therapeutically effective amount of the compound according to claim 1 to a mammal in need thereof, wherein the cancer is selected from Burkitt's lymphoma, Hodgkin's lymphoma, non-Hodgkin's lymphoma, diffuse large B-cell lymphoma, follicular lymphoma, multiple myeloma, bladder cancer, breast cancer, colon cancer, melanoma, ovarian cancer, prostate cancer, small cell lung carcinoma, non-small cell lung cancer, NUT midline carcinoma, acute B-cell lymphoma, and head and neck squamous cell carcinoma.

22. A method of treating cancer comprising administering a therapeutically effective amount of the compound according to claim 1 to a mammal in need thereof, wherein said cancer:

is associated with overexpression, translocation, amplification, or rearrangement of a myc family oncoprotein and is selected from B-acute lymphocytic leukemia, Burkitt's lymphoma, Diffuse large B-cell lymphoma, Multiple myeloma, Primary plasma cell leukemia, Atypical carcinoid lung cancer, Bladder cancer, Breast cancer, Cervix cancer, Colon cancer, Gastric cancer, Glioblastoma, Hepatocellular carcinoma, Large cell neuroendocrine carcinoma, Medulloblastoma, Melanoma, nodular, Melanoma, superficial spreading, Neuroblastoma, esophageal squamous cell carcinoma, Osteosarcoma, Ovarian cancer, Prostate cancer, Renal clear cell carcinoma, Retinoblastoma, Rhabdomyosarcoma, and Small cell lung carcinoma;

is associated with overexpression, translocation, amplification, or rearrangement of BET proteins and is selected from NUT midline carcinoma, B-cell lymphoma, non-small cell lung cancer, esophageal cancer, head and neck squamous cell carcinoma, breast cancer, prostate cancer, and colon cancer;

that relies on pTEFb (Cdk9/cyclin T) and BET proteins to regulate oncogenes and is selected from chronic lymphocytic leukemia, multiple myeloma, follicular lymphoma, diffuse large B-cell lymphoma, Burkitt's lymphoma, Hodgkin's lymphoma, anaplastic large cell lymphoma, neuroblastoma and primary neuroectodermal tumor, rhabdomyosarcoma, prostate cancer, and breast cancer;

is associated with upregulation of BET responsive genes CDK6, Bcl2, TYRO3, MYB, and hTERT is selected from pancreatic cancer, breast cancer, colon cancer, glioblastoma, adenoid cystic carcinoma, T-cell prolymphocytic leukemia, malignant glioma, bladder cancer, medulloblastoma, thyroid cancer, melanoma, multiple myeloma, Barret's adenocarcinoma, hepatoma, prostate cancer, pro-myelocytic leukemia, chronic lymphocytic leukemia, mantle cell lymphoma, diffuse large B-cell lymphoma, small cell lung cancer, and renal carcinoma;

is sensitive to effects of BET inhibition is selected from NUT-midline carcinoma (NMV), acute myeloid leukemia (AML), acute B lymphoblastic leukemia (B-ALL), Burkitt's Lymphoma, acute B-cell Lymphoma, Melanoma, mixed lineage leukemia, multiple myeloma, pro-myelocytic leukemia (PML), non-Hodgkin's lymphoma, Neuroblastoma, Medulloblastoma, lung carcinoma (NSCLC, SCLC), breast cancer, prostate cancer, and colon carcinoma; and/or is associated with a virus selected from Epstein-Barr Virus (EBV), hepatitis B virus (HBV), hepatitis C virus (HCV), Kaposi's sarcoma associated virus (KSHV), human papilloma virus (HPV), Merkel cell polyomavirus, and human cytomegalovirus (CMV).

23. A method of treating cancer comprising administering a therapeutically effective amount of the compound according to claim 1 to a mammal in need thereof, wherein said cancer is associated with the MYC oncogene.

24. The method of claim 21, wherein the cancer is resistant to treatment with immunotherapy, hormone-deprivation therapy, and/or chemotherapy.

25. The method of claim 21, wherein administration of a therapeutically effective amount of said compound:

restores sensitivity to immunotherapy, hormone-deprivation therapy, and/or chemotherapy; and/or inhibits proliferation of cancer cells, and/or induces cancer cell death or senescence.

26. The method of claim 21, wherein said compound is combined with other therapies, chemotherapeutic agents, or antiproliferative agents.

27. A method of treating a benign proliferative or fibrotic disorder selected from benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, juvenile polyposis syndrome, idiopathic pulmonary fibrosis, renal fibrosis, post-operative stricture, keloid formation, scleroderma, and cardiac fibrosis, comprising administering a therapeutically effective amount of the compound of claim 1 to a mammal in need thereof.

28. A method of treating a disease or disorder comprising administering a therapeutically effective amount of the compound according to claim 1 to a mammal in need thereof, wherein said disease or disorder is selected from:

cardiovascular disease, dyslipidemia, atherosclerosis, hypercholesterolemia, metabolic syndrome, Alzheimer's disease, obesity-associated inflammation, type II diabetes, insulin resistance, Alzheimer's disease, Parkinson's disease, Huntington disease, bipolar disorder, schizophrenia, Rubinstein-Taybi syndrome, and epilepsy.

29. A pharmaceutical composition comprising the compound of claim 16, and a pharmaceutically acceptable carrier.

30. A pharmaceutical composition comprising the compound of claim 17, and a pharmaceutically acceptable carrier.

* * * * *

UNITED STATES PATENT AND TRADEMARK OFFICE
CERTIFICATE OF CORRECTION

PATENT NO. : 10,292,968 B2  
APPLICATION NO. : 15/534105  
DATED : May 21, 2019  
INVENTOR(S) : Samuel David Brown et al.

Page 1 of 2

It is certified that error appears in the above-identified patent and that said Letters Patent is hereby corrected as shown below:

On the Title Page

Abstract, Item (57), Lines 1-2:  
"heterocycles compound"  
Should read:  
--heterocyclic compounds--.

In the Claims

Claim 1, Column 84, Line 58:  
"from -NH, -N-R$_{1b}$ and"  
Should read:  
--from NH, NR$_{1b}$ and--.

Claim 1, Column 84, Line 59:  
"from N, and -CH-;"  
Should read:  
--from N and CH;--.

Claim 3, Column 85, Line 65:  
"-NR$_{1b}$."  
Should read:  
--NR$_{1b}$.--.

Claim 16, Column 89, Lines 58-59:  
"4-Cyclopropyl-3-(5-(1-methyl-1H-indazol-6-yl)-2-(1H-pyrazol-4-yl)-1H-1,2,4-triazol-5(4H)-one;"  
Should read:  
--4-Cyclopropyl-3-(5-(1-methyl-1H-indazol-6-yl)-2-(1H-pyrazol-4-yl)-1H-imidazol-4-yl)-1H-1,2,4-triazol-5(4H)-one;--.

Signed and Sealed this  
Thirteenth Day of August, 2019

Andrei Iancu  
*Director of the United States Patent and Trademark Office*

CERTIFICATE OF CORRECTION (continued)
U.S. Pat. No. 10,292,968 B2

Claim 17, Column 89, Line 65:
"A compound is selected from:"
Should read:
--A compound selected from:--.

Claim 17, Column 90, Line 51:
"6hydrochloride;"
Should read:
--hydrochloride;--.

Claim 20, Column 90, Line 64:
Delete "slam-96".

Claim 20, Column 91, Lines 33-35:
Delete ", comprising administering a therapeutically effective amount of the compound according to claim 1 to a mammal in need thereof".